United States Patent
Yamaya et al.

(10) Patent No.: US 6,824,509 B2
(45) Date of Patent: Nov. 30, 2004

(54) ENDOSCOPE

(75) Inventors: Koji Yamaya, Hachioji (JP); Koji Nakamoto, Hachioji (JP); Hisao Yabe, Hachioji (JP)

(73) Assignee: Olympus Corporation, Tokyo (JP)

( * ) Notice: Subject to any disclaimer, the term of this patent is extended or adjusted under 35 U.S.C. 154(b) by 175 days.

(21) Appl. No.: 10/200,631

(22) Filed: Jul. 22, 2002

(65) Prior Publication Data

US 2003/0040657 A1 Feb. 27, 2003

(30) Foreign Application Priority Data

| Jul. 23, 2001 | (JP) | 2001/221909 |
| Jul. 23, 2001 | (JP) | 2001/221910 |
| Aug. 7, 2001 | (JP) | 2001/239755 |
| Aug. 13, 2001 | (JP) | 2001/245606 |
| Jan. 15, 2002 | (JP) | 2002/006479 |
| Jan. 21, 2002 | (JP) | 2002/012097 |
| Apr. 26, 2002 | (JP) | 2002/126727 |
| May 24, 2002 | (JP) | 2002/151375 |

(51) Int. Cl.[7] ............................... A61B 1/00
(52) U.S. Cl. .................. 600/106; 600/104; 600/107
(58) Field of Search ........................ 600/104, 105, 600/106, 107, 129, 153

(56) References Cited

U.S. PATENT DOCUMENTS 6,458,074 B1 * 10/2002 Matsui et al. ............... 600/106

FOREIGN PATENT DOCUMENTS

| JP | S52-17679 | 12/1972 |
| JP | 2000-037348 | 2/2000 |
| JP | 2001-212078 | 8/2001 |

* cited by examiner

Primary Examiner—Beverly M. Flanagan
(74) Attorney, Agent, or Firm—Scully, Scott, Murphy & Presser

(57) ABSTRACT

A treatment instrument passage channel through which a treatment instrument can be passed lies through an elongated insertion unit that is inserted into a body cavity or the like. The distal opening of the treatment instrument passage channel opens onto the distal part of the insertion unit. A treatment instrument swing stand having a hole, through which the distal part of a treatment instrument led out of the distal opening is passed, bored therein is disposed near the distal opening so that the treatment instrument swing stand can swing freely. The treatment instrument swing stand is manipulated by proximally pulling angling wires. Thus, the distal part of the treatment instrument is swung from a position near the center of a field of view in both the rightward and leftward directions of an endoscope. Thus, the mucosa of a lesion can be resected easily while being caught in the field of view.

33 Claims, 52 Drawing Sheets

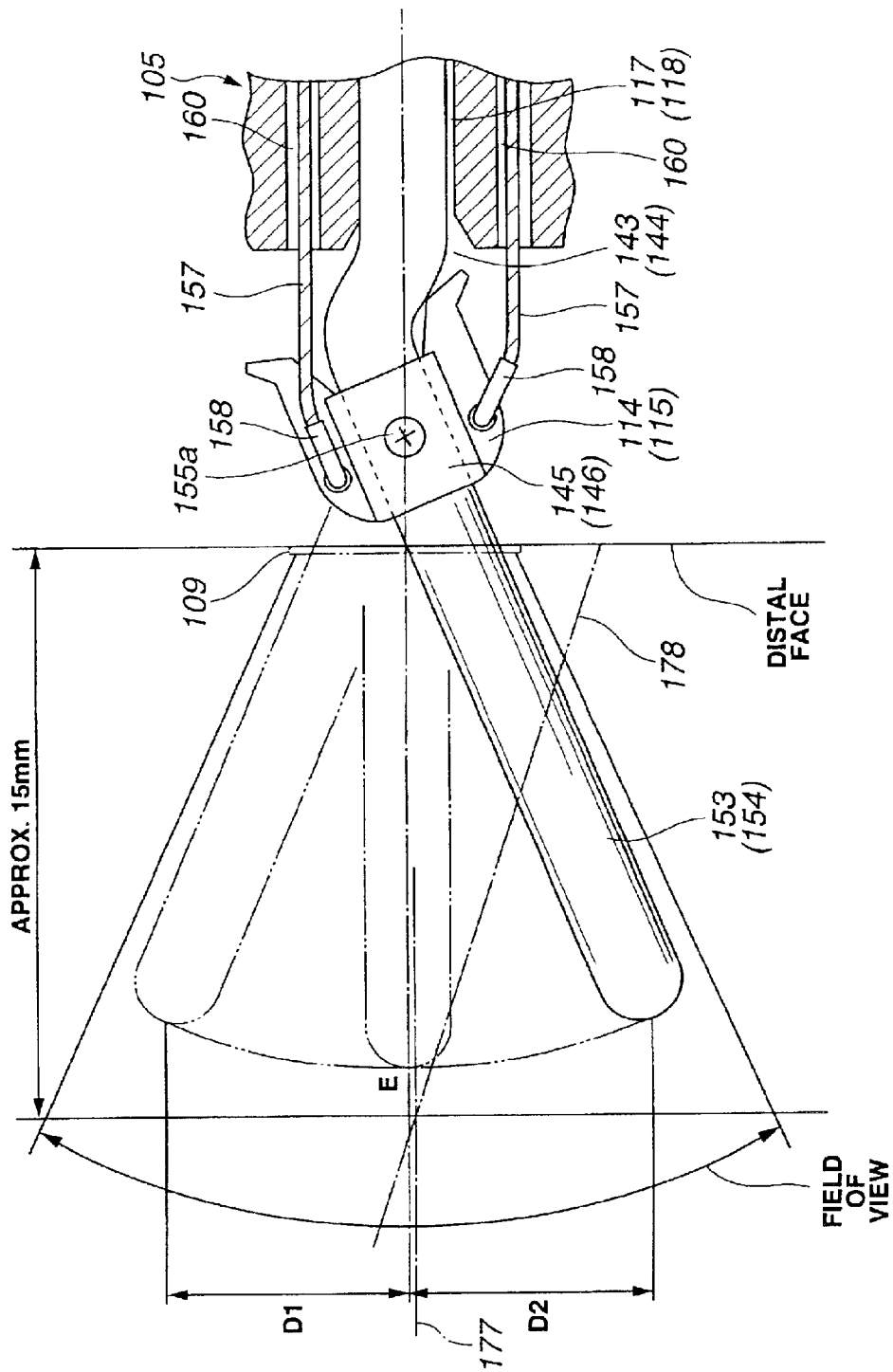

ENDOSCOPE

This application claims the benefit of Japanese Application Nos. 2001-221909 filed on Jul. 23, 2001, 2001-221910 filed on Jul. 23, 2001, 2001-239755 filed on Aug. 7, 2001, 2001-245606 filed on Aug. 13, 2001, 2002-6479 filed on Jan. 15, 2002, 2002-12097 filed on Jan. 21, 2002, 2002-126727 filed on Apr. 26, 2002, and 2002-151375 filed on May 24, 2002 respectively, the contents of which are incorporated by reference.

BACKGROUND OF THE INVENTION
Field of the Invention and Description of the Related Art The present invention relates to an endoscope having a treatment instrument passage channel and capable of performing various kinds of treatments by swinging a treatment instrument that is projected through an opening of the treatment instrument passage channel.

Endoscopes for medical use have been widely adopted in the past. An elongated insertion unit of such an endoscope is inserted into a body cavity in order to observe an organ within the body cavity or in order to, if necessary, perform various cures or treatments using a treatment instrument passed through a treatment instrument channel.

In recent years, such a procedure has been widely appreciated that resects a lesion in a body cavity using an endoscope that includes a plurality of treatment instrument passage channels and that has different treatment instruments passed through the treatment instrument passage channels.

For example, Japanese Unexamined Patent Application Publication No. 2000-37348 describes an endoscope for therapeutic use that is designed to include two treatment instrument passage channels and to have various treatment instruments passed through the treatment instrument passage channels.

In the above endoscope for therapeutic use, a forceps raising device is included in a distal opening portion of one treatment instrument passage channel. The forceps raising device moves away from the distal opening portion of the other treatment instrument passage channel. A clamping treatment instrument (hereinafter referred to as clamp forceps) and an incising treatment instrument (hereinafter referred to as a cutting instrument) such as a cautery knife needle are used in combination for treatment. Herein, the clamping treatment instrument is passed through the treatment instrument passage channel including the forceps raising device, while the incising treatment instrument is passed through the other treatment instrument passage channel.

To be more specific, after the mucosa of a lesion or a nearby region is clamped using the clamp forceps, the clamp forceps are moved away from the treatment instrument passage channel through which the cutting instrument is passed. The pulled mucosa is then resected using the cutting instrument.

However, as far as the endoscope for therapeutic use described in the above publication is concerned, a guiding means for resecting the mucosa, which is pulled using the clamp forceps, sideways with the cutting edge of the cutting instrument has not been described at all. With the features of the endoscope for therapeutic use, the cutting edge of the cutting instrument must be guided by angling the endoscope. This poses a problem in that the clamp forceps and a field of view offered by the endoscope move along with the angling.

Moreover, it is hard to delicately manipulate the cutting edge of the cutting instrument by angling the endoscope. Incising work becomes very hard to do. Besides, A range resectable with one manipulation is limited.

OBJECTS AND SUMMARY OF THE INVENTION

An object of the present invention is to provide an endoscope that proves excellent in performing endoscopic treatment with a treatment instrument projected through a distal opening of a treatment instrument passage channel.

Another object of the present invention is to provide an endoscope permitting an operator to easily maintain a state in which an object region to be treated and the distal part of a treatment instrument are caught in a field of view, and to easily perform treatment using the treatment instrument.

According to the present invention, an endoscope has an objective optical system that picks up an endoscopic image, and a treatment instrument passage channel, which introduces a treatment instrument to a body cavity, disposed in a distal part of an insertion unit thereof.

A treatment instrument swing stand permitting the distal part of a treatment instrument to move in both the rightward and leftward directions of the endoscope with a centerline, which bisects a field of view in the rightward and leftward directions, as a border is disposed near a distal opening portion of the treatment instrument passage channel. Thus, the distal part of the treatment instrument can be moved in the rightward and leftward directions of the endoscope over a wide range while being caught in the field of view.

BRIEF DESCRIPTION OF THE DRAWINGS

FIG. 1 is a longitudinal sectional view for explaining the structure of the distal part of an insertion unit of an endoscope;

FIG. 2 is a front view of the distal part;

FIG. 3 shows a first treatment instrument swing stand seen from an arrow P in FIG. 1;

FIG. 4 is an A–B sectional view of the distal part shown in FIG. 1;

FIG. 5 is an explanatory diagram showing the appearance of the first treatment instrument swing stand;

FIG. 6 is an explanatory diagram concerning the relationship between the position of a treatment instrument that is swung by the first treatment instrument swing stand and a field of view for observation;

FIG. 7 is an explanatory diagram showing an image of a treatment instrument displayed on a TV monitor;

FIG. 8 explains an operation to be exerted by the first treatment instrument swing stand;

FIG. 9 explains an operation to be exerted by the first and second treatment instrument swing stands;

FIG. 10 explains an operation to be exerted by the first and second treatment instrument swing stands;

FIG. 11 is an explanatory diagram showing another first treatment instrument swing stand that has another structure;

FIG. 12 is a sectional view showing part of the structure of the distal part including the first treatment instrument swing stand shown in FIG. 11;

FIG. 13 is an explanatory diagram showing an image of a treatment instrument displayed on a TV monitor;

FIG. 14 is an explanatory diagram showing another first treatment instrument swing stand that has another structure;

FIG. 15 is an explanatory diagram showing an image of a treatment instrument displayed on a TV monitor;

FIG. 16 is a longitudinal sectional view for explaining another distal part of an insertion unit of an endoscope that has another structure;

FIG. 17 is an explanatory diagram showing an image of a treatment instrument displayed on a TV monitor;

FIG. 18 is an explanatory diagram showing an image of a treatment instrument displayed on a TV monitor included in the second embodiment;

FIG. 19 is an explanatory diagram showing an image of a treatment instrument displayed on a TV monitor included in a variant of the second embodiment;

FIG. 20 is an explanatory diagram concerning the positional relationship between a treatment instrument that is swung by a first treatment instrument swing stand included in the third embodiment and an opening;

FIG. 21 is an explanatory diagram showing an image of a treatment instrument displayed on a TV monitor;

FIG. 22 is a front view of the distal part of an endoscope in accordance with the fourth embodiment;

FIG. 23 is a longitudinal sectional view of the distal part of the endoscope;

FIG. 24 is an explanatory diagram concerning an opening of a treatment instrument passage hole and the swing of a treatment instrument that projects through the opening;

FIG. 25 is an explanatory diagram showing an image of a treatment instrument displayed on a TV monitor;

FIG. 26 is an explanatory diagram concerning the swingable range offered by a first treatment instrument swing stand and discerned in an endoscopic image;

FIG. 27 shows the position of the first treatment instrument swing stand relative to an observation window;

FIG. 28 is an explanatory diagram showing an image of a treatment instrument displayed on a TV monitor when the first treatment instrument swing stand shown in FIG. 27 is swung;

FIG. 29 is an explanatory diagram concerning an opening of a treatment instrument passage hole and the swing of a treatment instrument that is projected through the opening;

FIG. 30 is an explanatory diagram showing an image of the treatment instrument displayed on the TV monitor when the first treatment instrument swing stand shown in FIG. 29 is swung;

FIG. 31 is an explanatory diagram showing a direct-vision endoscope having first and second treatment instrument swing stands;

FIG. 32 is an explanatory diagram showing an image of a treatment instrument displayed on a TV monitor included in the fifth embodiment;

FIG. 33 is an explanatory diagram showing an example of the arrangement of components in a distal face of a first variant;

FIG. 34 is an explanatory diagram showing an example of the arrangement of components in a distal face of a second variant;

FIG. 35 is an explanatory diagram showing the components of an endoscope;

FIG. 36 is a front view of a distal part for explaining the arrangement of components in the distal face of the distal part;

FIG. 37 is a sectional view for explaining a major portion of an insertion unit rotator;

FIG. 38 is an explanatory diagram concerning the relationship between a slit and a lock pin;

FIG. 39 is an explanatory diagram showing a rotation stopper structure;

FIG. 40 is a sectional view for explaining the rotation stopper structure;

FIG. 41 is an explanatory diagram concerning the positional relationship between a treatment instrument inlet and a treatment instrument swing stand manipulation knob;

FIG. 42 is a perspective view for explaining a first treatment instrument swing stand;

FIG. 43 is an explanatory diagram concerning the swing of a first treatment instrument, which is led out of the first treatment instrument swing stand, within a field of view for observation;

FIG. 44 is an explanatory diagram showing an image of the first treatment instrument that swings while being contained in an endoscopic image;

FIG. 45 shows a scene where two treatment instruments are used to treat a lesion;

FIG. 46 shows an endoscopic image rendering the scene shown in FIG. 45;

FIG. 47 shows an endoscopic image displayed with an insertion unit rotator rotated 90° leftwards;

FIG. 48 shows an endoscopic image rotated using an image rotation facility;

FIG. 49 is an explanatory diagram showing a circular endoscopic image;

FIG. 50 is an explanatory diagram concerning another swing of a first treatment instrument or the like, which is led out of the first treatment instrument swing stand, within a field of view for observation;

FIG. 51 is an explanatory diagram concerning another swing of the first treatment instrument or the like, which is led out of the first treatment instrument swing stand, within a field of view for observation;

FIG. 52 to FIG. 59 are concerned with a seventh embodiment of the present invention;

FIG. 52 is a perspective view showing the overall configuration of an endoscope in accordance with the seventh embodiment;

FIG. 53 is a front view showing the distal part of an insertion unit;

FIG. 54 is an explanatory diagram showing the movement of a swing stand;

FIG. 55 is a perspective view showing the structure of a first treatment instrument swing stand;

FIG. 56 is a perspective view showing the structure of a second swing stand;

FIG. 57 is an explanatory diagram concerning treatment to be performed on a lesion using a first treatment instrument;

FIG. 58 is an explanatory diagram showing a view image displayed on a monitor and a manipulable range of a treatment instrument;

FIG. 59 is an explanatory diagram concerning treatment to be performed using first and second treatment instruments;

FIG. 60 is a perspective view showing the overall configuration of an endoscope in accordance with the eighth embodiment;

FIG. 61 is an explanatory diagram showing an electric switch unit;

FIG. 62 is an explanatory diagram concerning a tip movement predicted line along which the tip of a large-diameter treatment instrument is predicted to move;

FIG. 63 is an explanatory diagram concerning a tip movement predicted line along which the tip of a small-diameter treatment instrument is predicted to move;

FIG. 66 is a perspective view showing an endoscope in accordance with the eleventh embodiment;

FIG. 67 is a side view showing an external swing stand manipulation knob;

FIG. 68 is a front view showing the distal face of the distal part of the external swing stand;

FIG. 69 is a front view showing the distal face of an insertion unit included in a direct-vision endoscope in accordance with the twelfth embodiment;

FIG. 70 is a side view schematically showing a distal opening portion of a treatment instrument passage channel, which is formed in the distal part of an insertion unit, and its surroundings;

FIG. 71 is an explanatory diagram concerning the work of incising the tunica mucosa of a body cavity;

FIG. 72 shows an example of a view image;

FIG. 73A is a front view showing the distal face of an insertion unit of an oblique-vision endoscope in accordance with the thirteenth embodiment;

FIG. 73B is a side view schematically showing a distal opening portion of a treatment instrument passage channel, which is formed in the distal part of the insertion unit, and its surroundings;

FIG. 74 to FIG. 85E are concerned with a fourteenth embodiment of the present invention;

FIG. 74 is an oblique view showing the overall configuration of an endoscope in accordance with the fourteenth embodiment;

FIG. 75 is a sectional view showing a swing stand manipulator;

FIG. 76 is a sectional view showing the swing stand manipulator shown in FIG. 75 and seen from the direction of arrow F in FIG. 75;

FIG. 77 is a sectional view showing the swing stand manipulator shown in FIG. 75 and seen from the direction of arrow G in FIG. 75;

FIG. 78 is a sectional view showing in enlargement portion J of the swing stand manipulator shown in FIG. 75;

FIG. 80 is a perspective view showing an endoscope being operated;

FIG. 81 is a perspective view showing an endoscope in accordance with a first variant;

FIG. 83 is a perspective view showing an endoscope in accordance with a fourth variant;

FIG. 84 shows a scene where the endoscope in accordance with the third variant is used to arrest bleeding;

FIG. 85A to FIG. 85E show images displayed on a monitor; and

DESCRIPTION OF THE PREFERRED EMBODIMENTS

Referring to FIG. 1 to FIG. 10, a first embodiment of the present invention will be described below.

An endoscope of the first embodiment is of a type that displays a view image on the screen of a display device. An insertion unit 40 of the endoscope has, similarly to that of an ordinary endoscope, a distal part 1, a bending section, and a flexible tube joined in that order from the distal end thereof. The insertion unit 40 is made soft as a whole.

Incidentally, the overall configuration of the endoscope of the present embodiment is nearly identical to endoscopes of other embodiments to be described later, for example, an endoscope 101 shown in FIG. 35 except the structure of a distal part 105.

Figure 1:
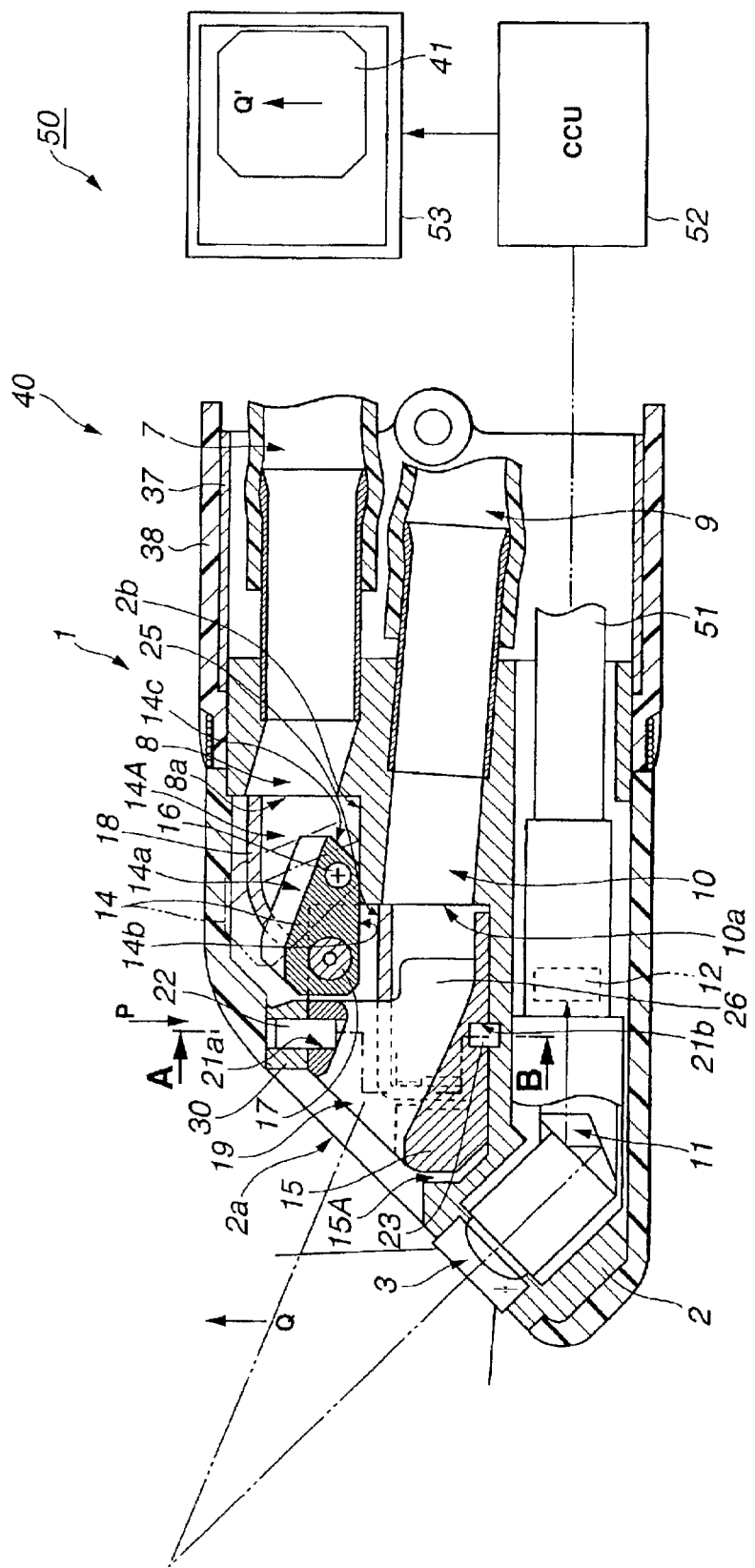
FIG. 1 to FIG. 10 are concerned with a first embodiment of the present invention.
Figure 2:
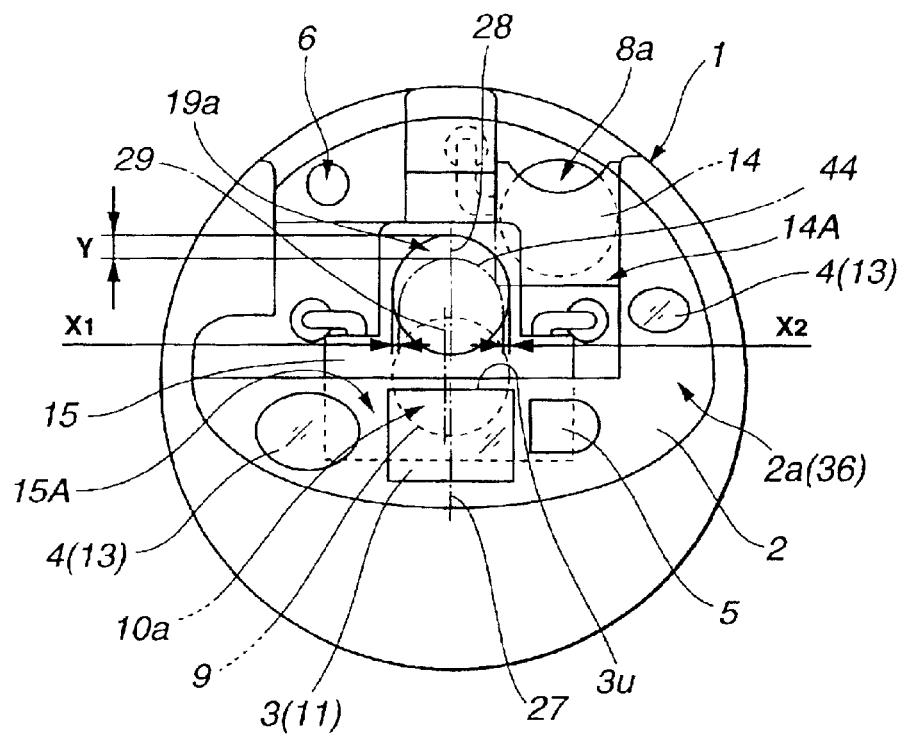

As shown in FIG. 1 and FIG. 2, the distal part 1 has a distal hard member 2 that is hard and that has an inclined face 2a serving as the distal face of the endoscope. The inclined face 2a of the distal hard member 2 contains: an observation window 3 abutted on an observation optical system (or an objective optical system); for example, two illumination windows 4 abutted on illumination optical systems 13; an air/water supply nozzle 5 whose opening is opposed to the observation window 3; a forward water outlet 6, a second channel opening 8a of a second channel opening portion 8 that communicates with a second treatment instrument passage channel 7; and a first channel opening 10a of a first channel opening portion 10 that communicates with a first treatment instrument passage channel 9. Thus, the endoscope of the present embodiment is an oblique-vision endoscope.

A second treatment instrument swing stand placement member 14A on which a second treatment instrument swing stand 14a is placed is disposed near the second channel opening portion 8 of the distal hard member 2. The second treatment instrument swing stand 14 has a treatment instrument mount plane 14a that adjusts the direction of projection of a treatment instrument in which the treatment instrument that is not shown and led out through the second channel opening 8a can be projected into a body cavity. The second treatment instrument swing stand 14 is shaped substantially like a flat plate, and swings vertically in the drawing.

Moreover, a first treatment instrument swing stand placement member 15A on which a first treatment instrument swing stand 15 is placed is disposed near the first channel opening portion 10. The first treatment instrument swing stand 15 has a treatment instrument passage hole 19 through which the direction of projection of a treatment instrument in which the treatment instrument that is not shown and led out through the first channel opening 10a can be projected into a body cavity is adjusted. The first treatment instrument swing stand 15 is shaped substantially like a block, and swings laterally in the drawing.

The position of the second treatment instrument swing stand 14 is set proximally to the position of the first treatment instrument swing stand 15 and above the position thereof. The positions of the second treatment instrument swing stand 14 and first treatment instrument swing stand 15 are set above the upper side 3u of the observation window 3. According to the present embodiment, the endoscope is of an oblique-vision type. Therefore, the observation window 3, first treatment instrument swing stand 15, and second treatment instrument swing stand 14 are arranged in the axial direction of the endoscope in that order from the distal edge of the inclined face 2a.

The first treatment instrument swing stand placement member 15A is disposed near the largest-diameter portion of the distal part 1 so that a swingable range within which the first treatment instrument swing stand 15 can swing can be widened without the necessity of increasing the outer diameter of the distal part of the endoscope.

The observation optical system 11 is not limited to an oblique-vision type but may be of a direct-vision or side-vision type. The observation window 3 may be circular but not have sides. Moreover, an imaging device 12 is disposed at the position of the image plane of the observation optical system 11. Furthermore, the distal ends of light guide fiber bundles that are not shown and that propagate illumination light open onto the proximal sides of the illumination windows 4.

A connector fixed to the terminal of a universal cord led out of an operation unit that is not shown and that is disposed proximally to the insertion unit 40 is coupled to a light source apparatus, whereby illumination light emanating from the light source apparatus is fed to the light guide fiber bundles. The light is propagated over the light guide fiber bundles, and emitted via the illumination optical systems 13 opposed to the distal ends of the light guide fiber bundles. Consequently, an object such as the mucosa of a lesion in a body cavity is illuminated.

An optical image of the illuminated object is picked up by the observation optical system 11 abutted on the observation window 3, and converged on the imaging surface of the imaging device 12. The imaging device 12 photoelectrically converts the optical image. The imaging device 12 is coupled to the tip of a cable 51. The tail of the cable 51 is routed to a video processor or a camera control unit (hereinafter CCU) 52 by way of a scope cable that is spliced to the connector fixed to the terminal of the universal cord.

The CCU 52 includes a drive circuit that produces a driving signal with which the imaging device 12 is driven, and a signal processing circuit that processes an image signal resulting from photoelectric conversion performed by the imaging device 12, and produces a video signal.

The video signal produced by the signal processing circuit is transferred to a TV monitor 53 that is a display device. An object image converged on the imaging surface of the imaging device 12 is displayed as a view image on a view image display screen 41 that is the display surface of the TV monitor 53.

The air/water supply nozzle 5 serves as a water supply nozzle through which a cleansing solution is sprayed to the face of the observation window 3 in order to cleanse the face, and also serves as a nozzle through which a gas such as air is supplied to a body cavity. Furthermore, a first bending piece 37 included in the bending section is coupled to the proximal end of the distal hard member 2. The first bending piece 37 is covered with a bending rubber 38.

The distal part of the bending rubber 38 is fixed to the distal hard member 2 by winding a thread about it or using an adhesive in order to keep the distal hard member 2 watertight. The bending section is bent by manipulating a manipulation knob that is not shown and that is formed on the operation unit proximal to the insertion unit 40. The distal hard member 2 can thus be angled in the upward, downward, rightward, or leftward direction of the endoscope.

Referring to FIG. 1 to FIG. 7, the structures of the second treatment instrument swing stand 14 and first treatment instrument swing stand 15 and the positional relationship between them will be described below. The direction of arrow Q in the distal part 1 of the endoscope shown in FIG. 1 corresponds to the upward direction Q' on the screen of the TV monitor 53 that is disposed outside the endoscope and seen by an operator.

First, referring to FIG. 1 to FIG. 3, the second treatment instrument swing stand 14 will be described below.

The second treatment instrument swing stand 14 can freely swing on a first shaft 16, which is located at the proximal end of the second treatment instrument swing stand 14, upwards and downwards relative to the distal hard member 2. Moreover, a first wire termination member 17 is included in the distal part of the second treatment instrument swing stand 14 so that the first wire termination member 17 can rotate freely. The distal part of a first angling wire 18 is fixed to the first wire termination member 17. The proximal part of the first angling wire 18 is passed through the insertion unit 40 and fixed to a second swing stand manipulating mechanism that is not shown.

When the second swing stand manipulating mechanism is used to advance the first angling wire 18, the second treatment instrument swing stand 14 swings on the first shaft 16 to move between an inverting position indicated with a solid line and a maximum raising position indicated with an alternative long two short dashes line.

The swing of the second treatment instrument swing stand 14 is restricted by an abutment surface 2b formed on the distal hard member 2, an inverting surface 14b of the second treatment instrument swing stand 14, and a raising surface 14c thereof. Specifically, when the second treatment instrument swing stand 14 is moved to the inverting position, the inverting surface 14b of the second treatment instrument swing stand 14 abuts against the abutment surface 2b of the distal hard member 2. When the second treatment instrument swing stand 14 is moved to the maximum raising position, the raising surface 14c of the second treatment instrument swing stand 14 abuts against the abutment surface 2b of the distal hard member 2.

Incidentally, the endoscope whose insertion unit 40 is as shown in FIG. 1, the CCU 52, the TV monitor 53, and a light source apparatus that is not shown constitute an endoscope system 50 for performing endoscopic examination or treating a lesion using, if necessary, a treatment instrument. Herein, the CCU 52 serves as a signal processing unit and is electrically connected to the imaging device 12 included in the endoscope. A view image resulting from photoelectric conversion performed by the imaging device 12 is displayed as an endoscopic image on the TV monitor 53 according to a video signal received from the CCU 52.

Next, referring to FIG. 1 to FIG. 7, the structure and position of the first treatment instrument swing stand 15 will be described below.

Figure 4:
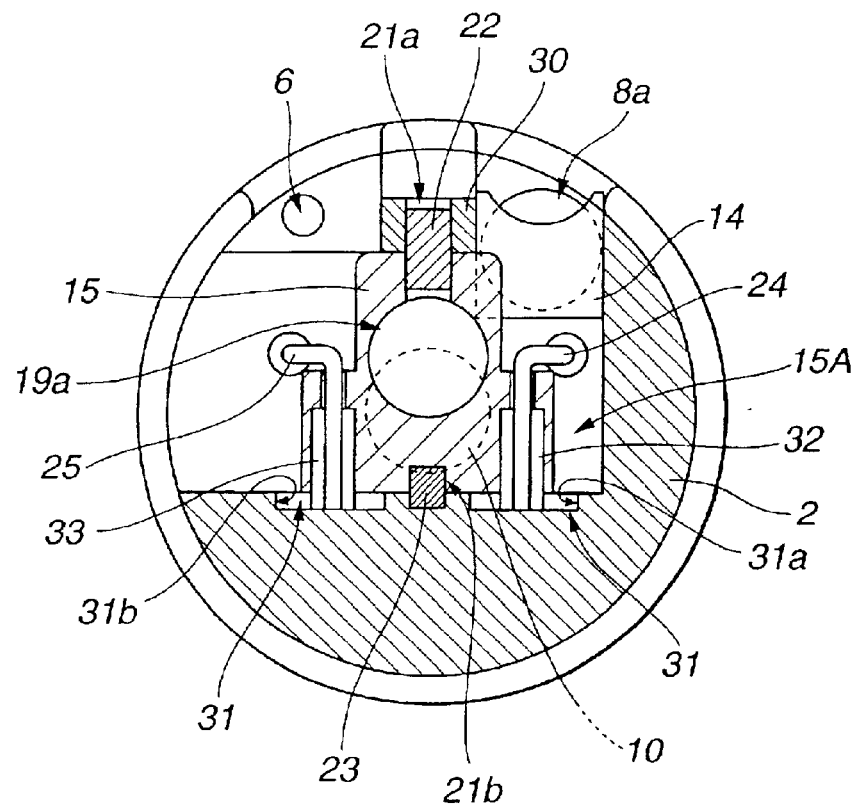

The first treatment instrument swing stand 15 can freely swing on two shafts 22 and 23 in the rightward and leftward directions of the distal hard member 2. The second shaft 22 and third shaft 23 are, as shown in FIG. 1 and FIG. 4, projected from the first treatment instrument swing stand 15 and disposed in an extended portion 30 of the distal hard member 2 and at a predetermined position in the distal hard member 2 respectively.

The first treatment instrument swing stand 15 consists of a stand body 20, a pair of treatment instrument guide walls 26, and a pair of convex parts 20b and 20c. The stand body 20 has an inclined face 20a that contains an opening 19a of a treatment instrument passage hole 19. The pair of treatment instrument guide walls 26 introduces the first treatment instrument, which is passed through the first treatment instrument passage channel 9, to the treatment instrument passage hole 19. The pair of convex parts 20b and 20c to which angling wires 24 and 25 used to swing the first treatment instrument swing stand 15 in the rightward and leftward directions of the endoscope are coupled projects from both sides of the inclined face 20a.

A first rotation shaft placement hole 21a in which the second shaft 22 is fitted is bored in the center of the top of the stand body 20. A second rotation shaft placement hole 21b in which the third shaft 23 is fitted is bored in the center of the bottom of the stand body 20 so that the second rotation shaft placement hole 21b will be coaxial to the first rotation shaft placement hole 21a.

The distal end of the second angling wire 24 is fixed to a wire termination member 32 that is included in the convex part 20b while being permitted to rotate freely. The distal end of the third angling wire 25 is fixed to a wire termination member 33 that is included in the convex part 20c while being permitted to rotate freely. The proximal ends of the second angling wire 24 and third angling wire 25 are passed through the insertion unit and fixed to a first swing stand manipulating mechanism that is not shown.

Consequently, when the first swing stand manipulating mechanism is used to advance or withdraw the angling wires 24 and 25, the first treatment instrument swing stand 15 swings on the second shaft 22 and third shaft 23 in the rightward and leftward directions of the endoscope.

As shown in FIG. 2, an opening centerline 28 bisects the opening 19a of the treatment instrument passage hole 19 in the rightward and leftward directions of the endoscope. A channel centerline 29 bisects the first channel opening portion 10 in the rightward and leftward directions. A field-of-view centerline 27 bisects the observation window 3 in the rightward and leftward directions. The opening centerline 28, channel centerline 29, and field-of-view centerline 27 are contained on substantially the same plane. Alternatively, the opening centerline 28, channel centerline 29, and field-of-view centerline 27 may be contained on substantially the same plane near a centerline bisecting the distal part in the rightward and leftward directions.

The swing of the first treatment instrument swing stand 15 is restricted by abutting the edges 31a and 31b of at least one or more stopper concave parts 31, which are shaped in conformity with the outline of the distal hard member 2, against the wire termination members 32 and 33. In other words, the edge 31a formed at a predetermined part of the stopper concave part 31 is abutted against the wire termination member 32, and the edge 31b formed at a predetermined part of the stopper concave part 31 is abutted against the wire termination member 33. Thus, a predetermined angle of rotation is defined.

Figure 6:
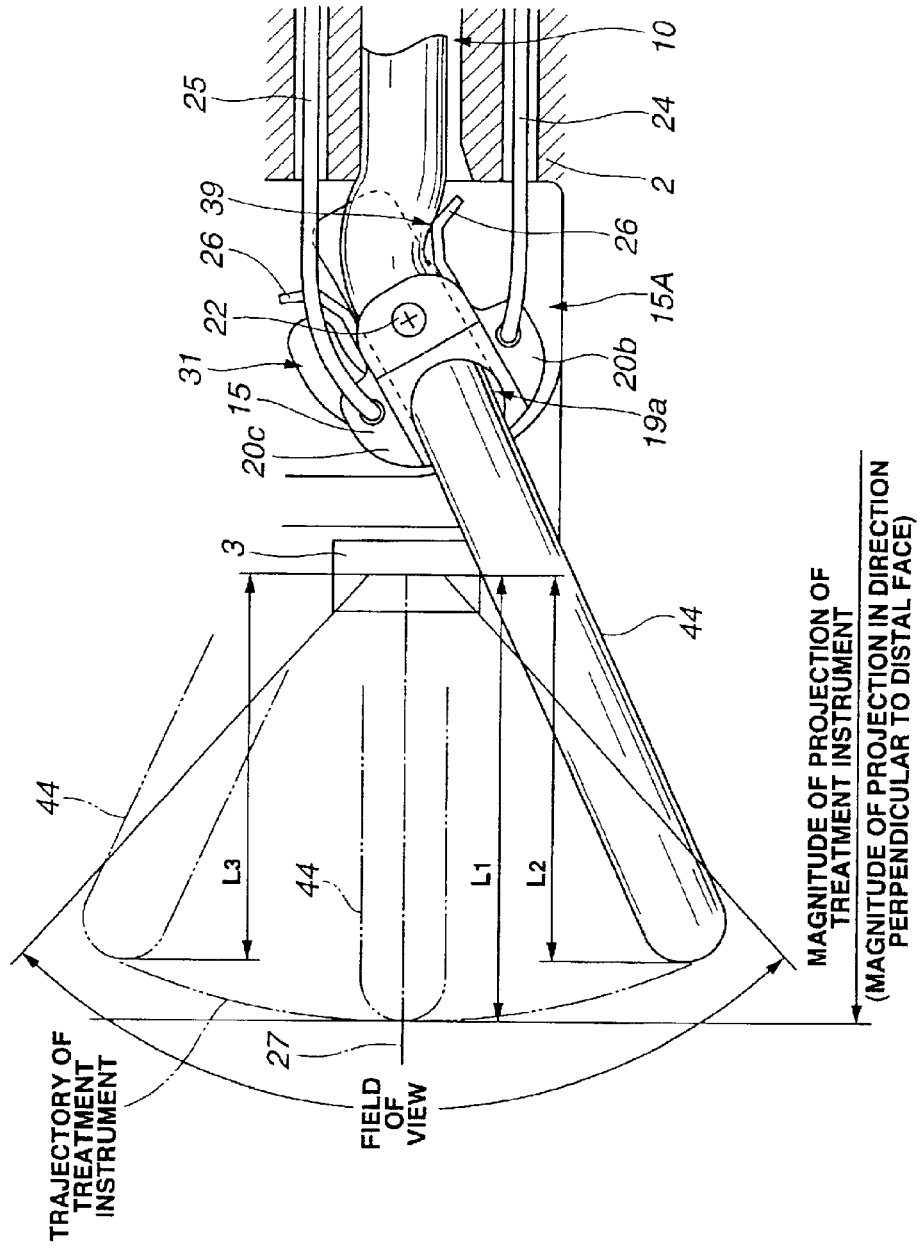

Since an angle of rotation is thus defined, after a treatment instrument 44 is, as shown in FIG. 6, projected by, for example, approximately 15 mm from the inclined face 2a that is the distal face of the distal hard member 2, the second angling wire 24 and third angling wire 25 are manipulated in order to swing the second treatment instrument swing stand 15. Consequently, the treatment instrument 44 traces a trajectory indicated with an alternate long and two short dashes line. At this time, the distal part of the treatment instrument 44 will not exceed the right and left edges of a field of view for observation which is offered by the observation window 3 (see FIG. 7). The distal part of the treatment instrument 44 swings by substantially the same distance in the rightward and leftward directions of the endoscope with respect to the field-of-view centerline 27.

Incidentally, when the treatment instrument 44 aligns with the field-of-view centerline 27, the tip of the treatment instrument 44 is located farthest from the inclined face 2a that is the distal face of the endoscope.

The trajectory of the tip of the treatment instrument 44 draws an upward curve as it goes to the right and left edges of a view image. This is because the distances L1, L2 and L3 from the observation window 3 shown in FIG. 6 have the relationship expressed below.

$$L2 \text{ (or } L3) < L1$$

Figure 7:
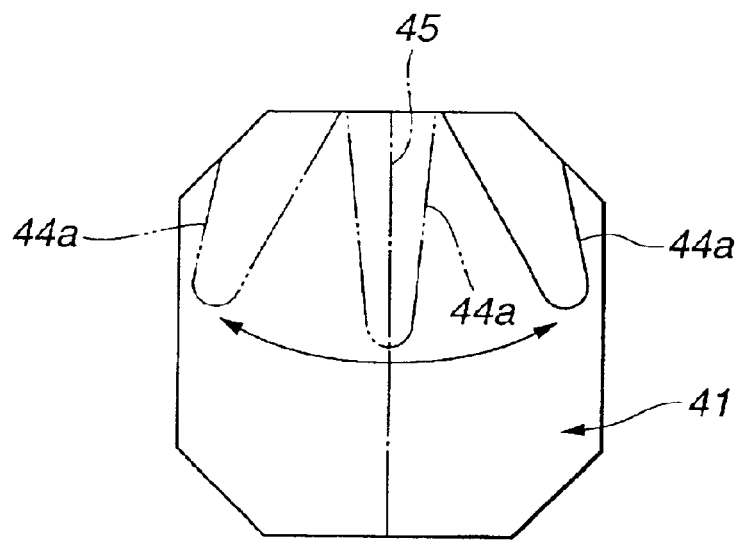

As shown in FIG. 7, an image 44a of the treatment instrument appears to project substantially from the upper margin of a view image display screen (which may be, simply, a screen) 41 of a display device, for example, the TV monitor 53.

At this time, since the opening centerline 28 of the opening 19a of the treatment instrument passage hole 19 and the field-of-view centerline 27 of the observation window 3 are defined as mentioned above, when the treatment instrument 44 is aligned with the field-of-view centerline 27, the image 44a of the treatment instrument is displayed on a screen centerline 45 that bisects the screen 41 right and left. A view image display area on the screen 41 nearly corresponds to the field of view for observation that is offered as a view by the observation optical system 11, imaged by the imaging device 12, and then observed.

Consequently, what has been described in relation to the screen 41 applies to the field of view for observation. In contrast, what has been described in relation to the field of view for observation applies to the screen 41 (the same applies to the subsequent embodiments).

Moreover, when the edge 31a or 31b of the stopper concave part 31 abuts against the wire termination member 32 or 33 respectively, the image 44a of the treatment instrument is displayed on the right or left margin of the screen. This helps an operator move the distal part of the treatment instrument in the rightward and leftward directions of the endoscope over a wide range including a position that corresponds to the center of an endoscopic image.

Incidentally, the image 44a of the treatment instrument appears to project substantially from the upper margin of the screen 41. This is because, as mentioned above, the position of the first treatment instrument swing stand 15 is set to a position above the upper side 3u of the observation window 3.

Moreover, a point of application or a ridge line of action 39 is formed on the internal surface of the treatment instrument guide wall 26. Herein, a pressure is applied to the treatment instrument 44 along the ridge line of action 39 so that when at least the first treatment instrument swing stand 15 is swung by the largest magnitude in the rightward and leftward directions of the endoscope, the treatment instrument 44 can move in a direction opposite to a direction of rotation. When the treatment instrument 44 is largely swung rightwards and leftwards, the treatment instrument 44 is supported at two points, that is, by the internal surface of the opening 19a and the ridge line of action 39. Work can be performed with the treatment instrument 44 held reliably.

Furthermore, the opening 19a of the treatment instrument passage hole 19 is shaped like an oval that is elongated in the upward and downward directions of the endoscope but not in the rightward and leftward directions thereof. As shown in FIG. 2, a clearance (Y) created in the upward direction between the treatment instrument 44 projected through the opening 19a of the treatment instrument passage hole 19 and the opening 19a is larger than or equal to a sum of clearances (X1+X2) created in the rightward and leftward directions, which are swingable directions, between them. In other words, the clearance Y and the clearances X1 and X2 have the relationship of $Y \geq X1+X2$. Thus, a magnitude of deflection of the treatment instrument 44 swung by the first treatment instrument swing stand 15 is minimized, and delicate work is enabled.

As shown in FIG. 4, the second angling wire 24 is passed immediately below the second treatment instrument swing stand 14 and routed to the insertion unit.

Figure 5:
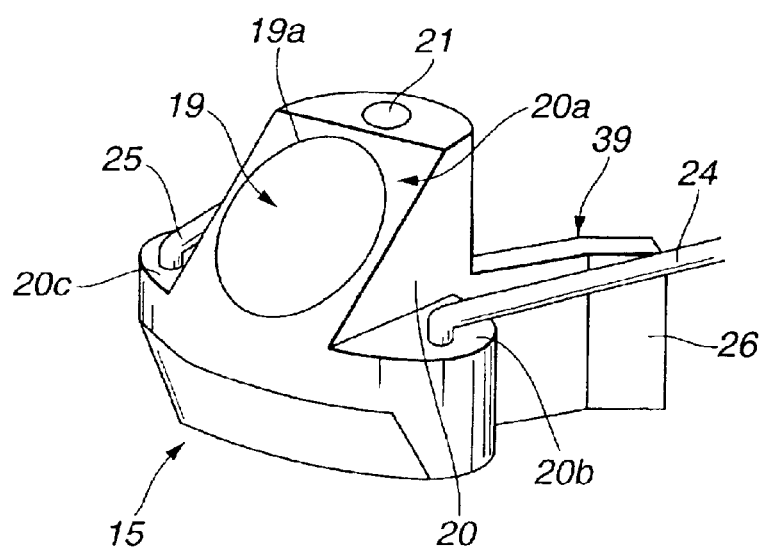

FIG. 5 shows the opening 19a whose perimeter is unintermittently contained in the inclined face 20a of the stand body 20. Alternatively, the opening 19a may be made so large that the perimeter of the opening 19a is intermittently contained in the inclined face 20a. In short, the shape of the opening 19a is not limited to any particular shape.

Furthermore, an opening is bored in the second treatment instrument swing stand placement member 14A on which the second treatment instrument swing stand 14 is placed. When the second treatment instrument swing stand 14 is raised, the opening opens upon the first treatment instrument swing stand placement member 15A. This leads to improved efficiency in cleansing and sterilizing the endoscope.

The height of the treatment instrument guide walls 26 is set to a dimension that prevents the angling wires 24 and 25 from coming into contact with the treatment instrument guide walls 26 when the first treatment instrument swing stand 15 is swung.

Moreover, the positional relationship between the second swing stand manipulating mechanism and first swing stand manipulating mechanism, or the internal diameters, materials, and hardness levels of the second treatment instrument passage channel 7 and first treatment instrument passage channel 9 are not confined to any specific ones.

Operations to be exerted by the endoscope having the foregoing features will be described below.

Figure 8:
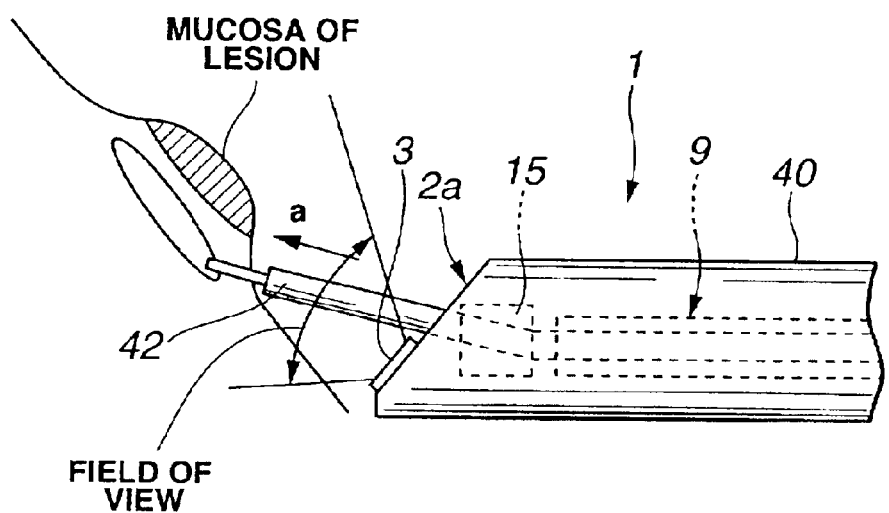

To be begin with, as shown in FIG. 8, the observation window 3 included in the distal part 1 of the insertion unit 40 is opposed to the mucosa of a lesion. The mucosa is observed through the endoscope. A treatment instrument, for example, an injection needle 42 is inserted into a body cavity through the first treatment instrument passage channel 9.

Herein, the first treatment instrument swing stand 15 is swung in order to oppose the injection needle 42 to predetermined part of the mucosa of the lesion. The injection needle 42 is then advanced to an intended region as indicated with arrow a. Physiological saline or any other medicine is then injected into the substratum of the mucosa of the lesion. This causes the tunica mucosa including the mucosa of the lesion to swell.

Figure 9:
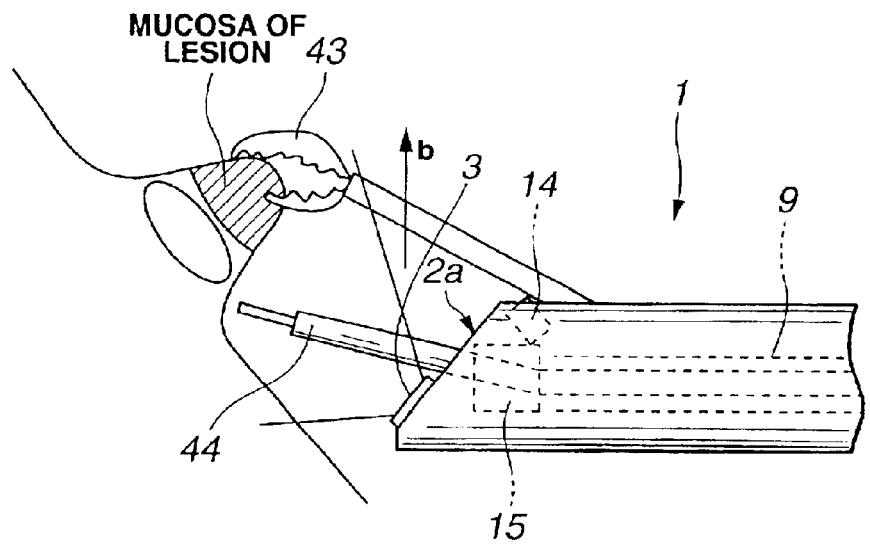

Next, as shown in FIG. 9, clamp forceps 43 that are a treatment instrument are introduced into the body cavity through the second treatment instrument passage channel 7. The second treatment instrument swing stand 14 is swung in order to oppose the clamp forceps 43 to the tunica mucosa that has swelled. When the clamp forceps 43 are opposed to a predetermined region on the tunica mucosa, the clamp forceps 43 are thrust forward in order to clamp the tunica mucosa that has swelled and that includes the mucosa of the lesion. Meanwhile, a cutting instrument 44 that is a treatment instrument is inserted into the first treatment instrument passage channel 9 on behalf of the injection needle 42. The cutting instrument 44 is placed near the mucosa of the lesion.

Thereafter, the second treatment instrument swing stand 14 is swung in order to raise the clamp forceps 43 in the direction of arrow b. Consequently, the tunica mucosa including the mucosa of the lesion clamped by the clamp forceps 43 is lifted.

Figure 10:
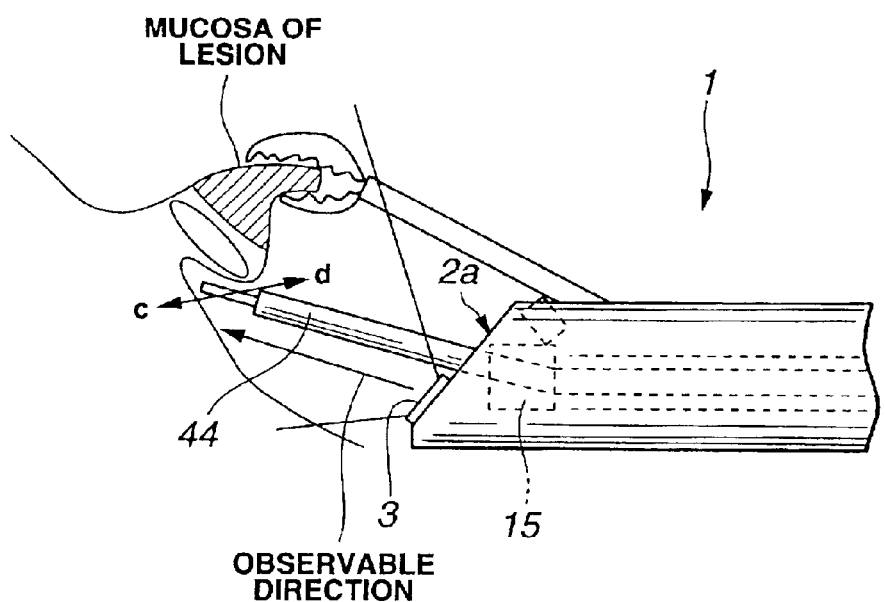

The first treatment instrument swing stand 15 is, as shown in FIG. 10, swung in the directions of arrows c and d in order to resect the substratum of the swelled mucosa using the cutting instrument 44. At this time, the second treatment instrument swing stand 14 is located above the first treatment instrument swing stand 15. Therefore, while the mucosa of the lesion is lifted, the root of the mucosa of the lesion can be resected swiftly with care given to the situation of an incised surface, for example, the depth of the cutting edge of the cutting instrument 44 that is seen through the observation window 3. At this time, the distal part of the treatment instrument can be moved in the rightward and leftward directions of the endoscope over a wide range including a position that corresponds to the center of an endoscopic image. Moreover, every state of the moved distal part of the treatment instrument can be observed.

When an image of the cutting instrument 44 displayed on the screen is located near the screen centerline 45, the cutting edge of the cutting instrument 44 is located farthest from the distal face of the endoscope. In other words, when the image of the cutting instrument 44 appears on one margin of the screen, even if the cutting instrument 44 is swung, the cutting edge of the cutting instrument dose not deeply cut the lesion. An operator takes account of this fact and proceeds with incision.

Consequently, when the endoscope is used in combination with treatment instruments that are accessories of the endoscope, a lesion extending over a wide range can be reliably and easily resected at a time, or any other procedure can be reliably and easily performed on the lesion. Since it is easy to manipulate the treatment instruments, a surgical procedure can be achieved reliably and swiftly. This leads to a lightened load on an operator or a patient.

Incidentally, the cutting instrument 44 may be introduced into a body cavity through the second treatment instrument passage channel 7, and the clamp forceps 43 may be introduced into the body cavity through the first treatment instrument passage channel 9. The position on the mucosa of the body cavity relative to the distal end of the endoscope may then be adjusted. Even in this case, incision can be achieved in the same manner as the aforesaid one.

Next, a first variant of the first embodiment will be described with reference to FIG. 11 to FIG. 13.

Figure 11:
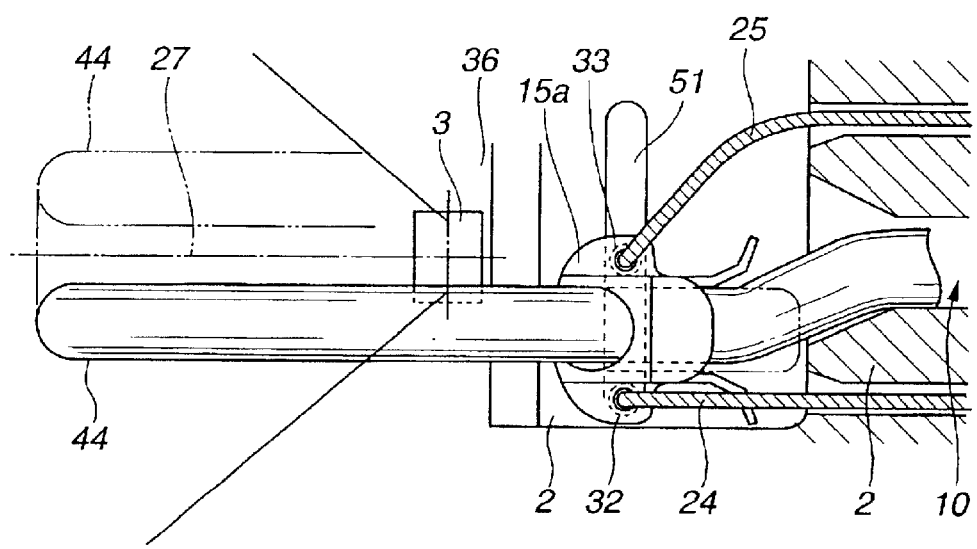
FIG. 11 to FIG. 13 are concerned with a first variant of the first embodiment.

As shown in FIG. 11, according to the present variant, unlike the one included in the aforesaid embodiment, the first treatment instrument swing stand 15 is not swung on the rotation shaft. A stopper concave part 51 that has a linear groove formed parallel to the observation window 3 is disposed at a predetermined position in the distal hard member 2. The first treatment instrument swing stand 15a is displaced in parallel in the rightward and leftward directions of the endoscope with respect to the field-of-view centerline 27 of the observation window 3.

Figure 12:
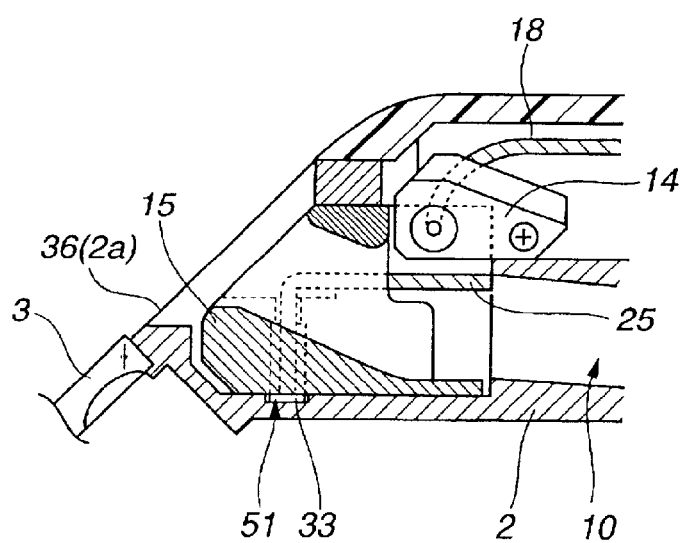
Figure 13:
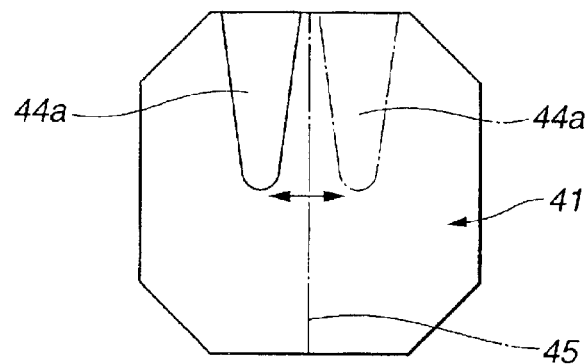

In other words, as shown in FIG. 11 and FIG. 12, the lower end of the second wire termination member 32 fixed to the distal part of the second angling wire 24, and the lower end of the third wire termination member 33 fixed to the distal part of the third angling wire 25 are disposed in the stopper concave part 51.

Consequently, when the second angling wire 24 and third angling wire 25 are handled, the first treatment instrument swing stand 15 moves in parallel with the distal face 36 in the rightward and leftward directions of the endoscope with respect to the field-of-view centerline 27. At this time, the distance from the tip of the treatment instrument 44 that is moved owing to the first treatment instrument swing stand 15 to the distal face 36 of the endoscope remains constant within the swingable range. As shown in FIG. 13, the image 44a of the treatment instrument 44 displayed on the screen 41 of the display device moves in parallel with the upper margin of the screen rightwards and leftwards with respect to the screen centerline 45.

As mentioned above, the second treatment instrument swing stand is designed to move the tip of the treatment instrument in parallel in the rightward and leftward directions of the screen of the display device. In addition to the advantages of the aforesaid embodiment, such an advantage is provided that a procedure can be carried out with the tip of the treatment instrument positioned at a constant distance from the distal face of the endoscope. Consequently, when-the second treatment instrument swing stand is used to move, for example, a cutting instrument, it can be avoided that a cut surface becomes partly deep.

Next, a second variant of the first embodiment will be described with reference to FIG. 14 and FIG. 15.

Figure 14:
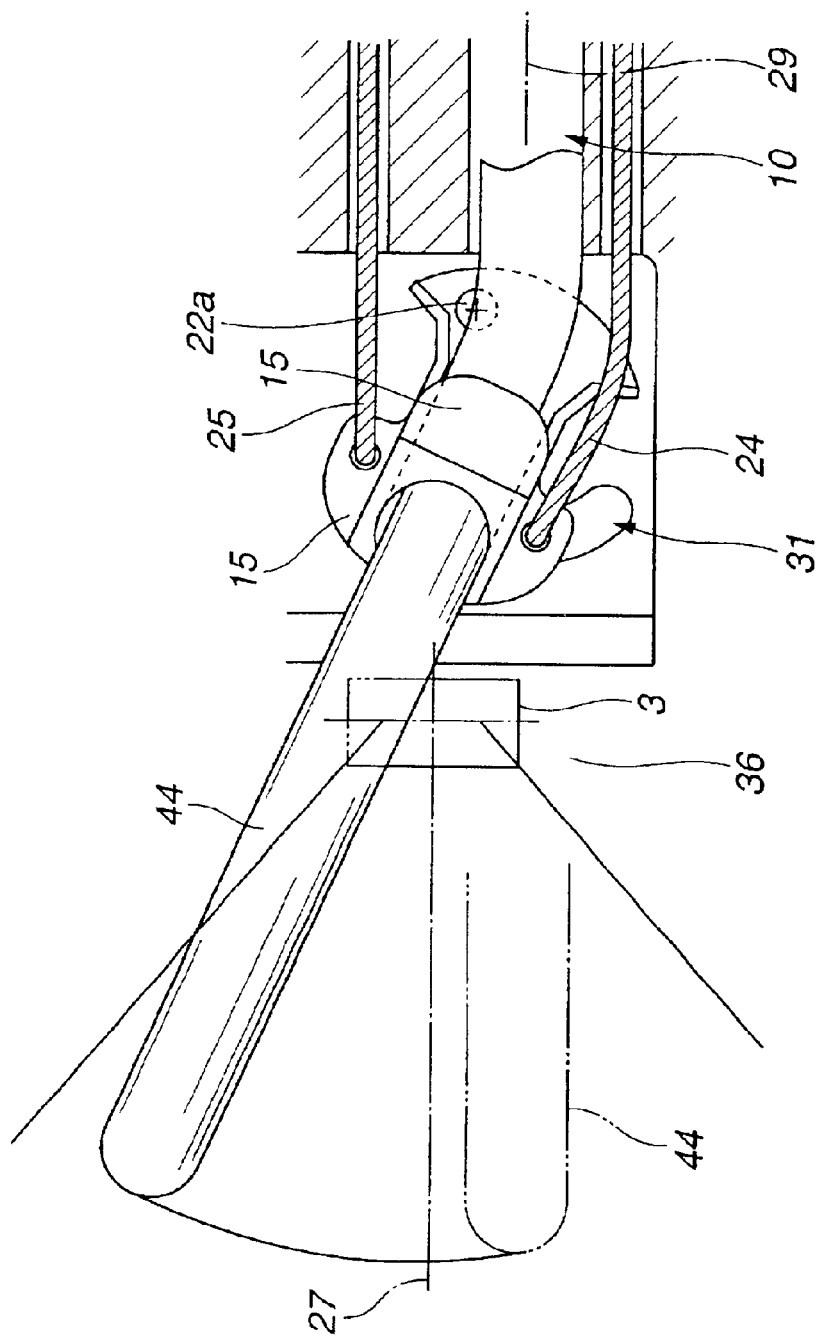

As shown in FIG. 14, according to the present variant, the position of one rotation shaft of the first treatment instrument swing stand 15 is changed to the one of a shaft 22a. Specifically, the position of the rotation shaft 22a is deviated from the channel centerline 29 of the first channel opening portion 10, and also deviated from the centerline of the first treatment instrument swing stand 15. Consequently, a distance by which the first treatment instrument swing stand 15 moves within the swingable range thereof is differentiated between the rightward and leftward directions of the endoscope with respect to the field-of-view centerline 27. When the treatment instrument 44 is swung to approach the field-of-view centerline 27, a distance by which the tip of the treatment instrument 44 projects from the distal face 36 becomes maximum.

Figure 15:
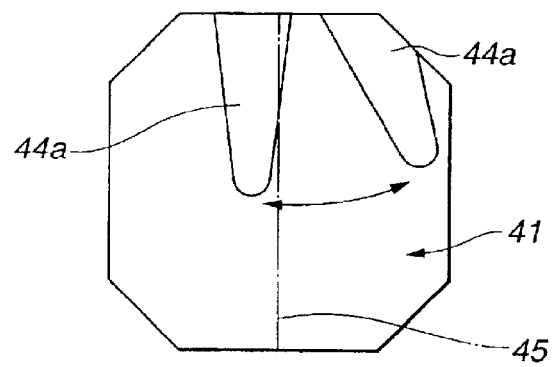
FIG. 14 and FIG. 15 are concerned with a second variant of the first embodiment.

As shown in FIG. 15, the distance by which the image 44a of the treatment instrument 44, which is displayed on the screen 41 of the display device, moves with respect to the screen centerline 45 is different between the rightward and leftward directions of the screen.

As mentioned above, the position of one rotation shaft of the first treatment instrument swing stand is changed. Consequently, in addition to the same advantages as those of the aforesaid embodiment, such an advantage is provided that the swingable range of a treatment instrument that is swung by the first treatment instrument swing stand can be changed according to a procedure required.

Next, a third variant of the first embodiment will be described with reference to FIG. 16 and FIG. 17.

Figure 16:
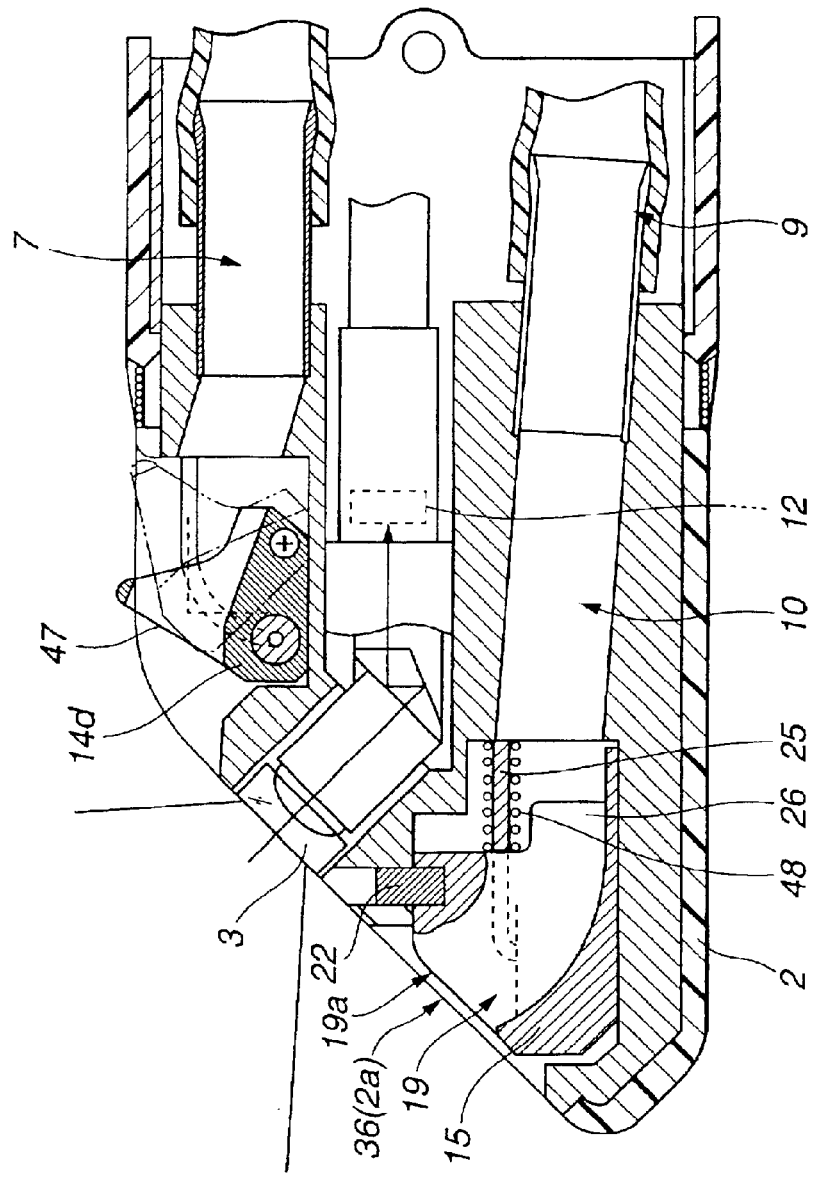

As shown in FIG. 16, according to the present variant, the first treatment instrument swing stand 15 is positioned below the observation window 3.

Moreover, the first treatment instrument swing stand 15 has only one rotation shaft of the second shaft 22. Moreover, the first treatment instrument swing stand 15 has an elastic member 48 whose constraining force varies depending on the swing of the first treatment instrument swing stand 15, for example, a spring.

Similarly to the first treatment instrument swing stand 15, a second treatment instrument swing stand 14d has an opening portion 47. Thus, a magnitude of deflection of the treatment instrument to be swung by the second treatment instrument swing stand 14d is minimized and delicate work is enabled.

Owing to the foregoing structure, when the angling wires 24 and 25 are not tensed at all, the first treatment instrument swing stand 15 returns from a swinging position to a predetermined position owing to a restoring force exerted by the elastic member 48. Moreover, as shown in FIG. 17, the image 44a of the treatment instrument appears to project substantially from the lower margin of the screen 41.

Figure 17:
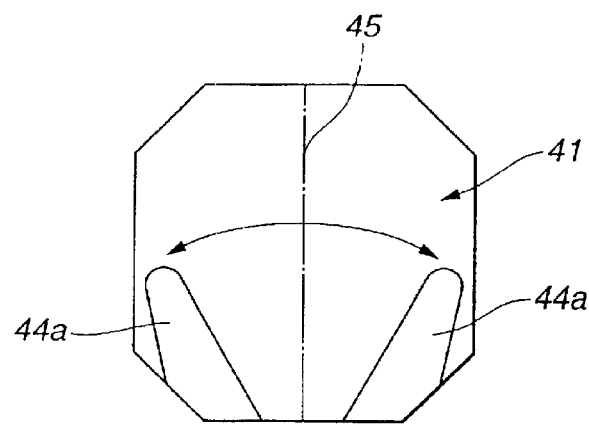
FIG. 16 and FIG. 17 are concerned with a third variant of the first embodiment.

As shown in FIG. 17, the swingable range of the first treatment instrument swing stand 15 is defined so that at least the tip of the treatment instrument will swing in the directions corresponding to the rightward and leftward directions of the screen with respect to the screen centerline 45. When the image 44a lies near the screen centerline 45, the distance by which the tip of the treatment instrument 44 projects from the distal face 36 is maximized. The other components are identical to those of the aforesaid embodiment.

As mentioned above, the elastic member 48 is included that exerts a constraining force which constrains the first treatment instrument swing stand 15 to return to the predetermined position when the angling wires are not tensed at all. Consequently, in addition to the same advantages as those of the aforesaid embodiment, such an advantage is provided that the first treatment instrument swing stand 15 can be returned to a desired position owing to the elastic member 48.

Specifically, owing to the elastic member 48, the treatment instrument guide walls 26 are brought to a predetermined state or opposed to the channel opening portion 10. Thus, the efficiency in guiding the treatment instrument to the first treatment instrument swing stand 15 is improved.

The present invention is not limited to the aforesaid embodiment and variants but can be changed in various aspects without a departure from the gist of the present invention. For example, a direct-vision endoscope having the distal face 36 thereof not inclined belongs to the present invention.

Next, a second embodiment of the present invention will be described with reference to FIG. 18 and FIG. 19. An endoscope of the present embodiment has basically the same components as the endoscope described in conjunction with FIG. 1 to FIG. 6. Differences alone will be described below.

According to the first embodiment, when the first treatment instrument swing stand 15 is swung, the image 44a of the treatment instrument 44 swings in the rightward and leftward directions of the screen 41 with respect to the centerline, which bisects the screen 41 in the rightward and leftward directions, as a border. According to the present embodiment, the distal part of the treatment instrument 44 is caught in a depth of field offered by the observation optical system 11. The distal part of the image 44a of the treatment instrument 44 almost reaches the centerline that bisects the screen 41 in the upward and downward directions of the screen.

As shown in FIG. 1 and others, the direction in which the field of view spreads is not parallel to but intersects the direction of projection in which the treatment instrument is projected via the first treatment instrument swing stand 15. In this state, the treatment instrument 44 swings by substantially the same distance in the rightward and leftward directions of the endoscope with respect to the field-of-view centerline 27 (see FIG. 2).

Figure 18:
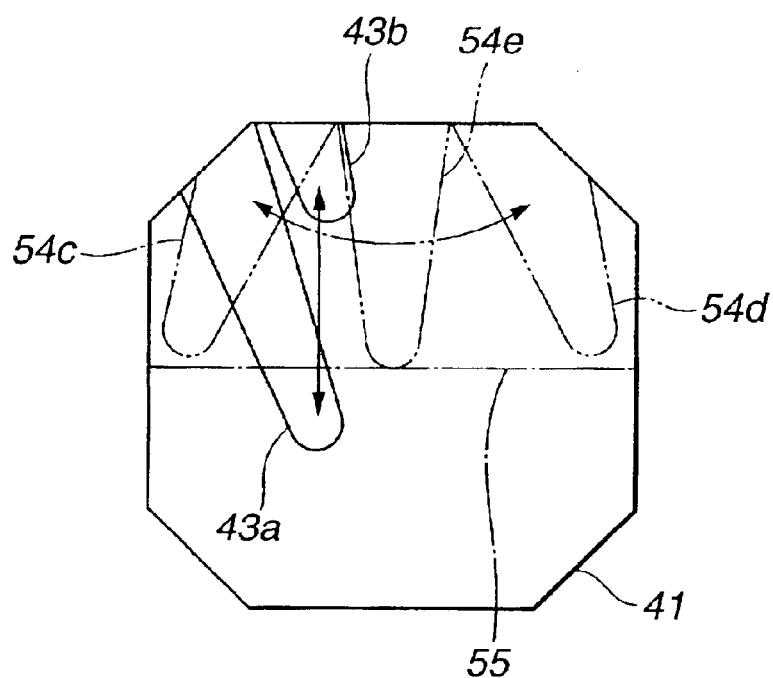
FIG. 18 and FIG. 19 are concerned with a second embodiment of the present invention.

Since the direction of a field of view intersects the direction of projection in which the treatment instrument 44 is projected via the first treatment instrument swing stand 15, a view image appears on the screen 41 as shown in FIG. 18.

Incidentally, when the treatment instrument 44 lies on the field-of-view centerline 27, the tip of the treatment instrument 44 is positioned farthest from the inclined face 2a that is the distal face of the endoscope. Moreover, one of the reasons why the treatment instrument 44 is positioned on the field-of-view centerline 27 is that a resolution is generally higher in the center of a field of view than in the perimeter thereof. The other reason is that an operator tends to catch a region to be observed or a region to be treated in the center of a field of view.

Next, referring to FIG. 18, the movements of the images of the treatment instruments, which are swung by the treatment instrument swing stands 14 and 15, in a view image will be described below.

As shown in FIG. 18, an image of a treatment instrument to be moved by the second treatment instrument swing stand 14, for example, clamp forceps 43 moves substantially in the upward and downward directions of a view image as indicated with solid lines. On the other hand, an image of a treatment instrument to be moved by the first treatment instrument swing stand 15, for example, a cutting instrument 54 moves substantially in the rightward and leftward directions of a view image as indicated with alternate long and two short dashes lines.

To be more specific, when the second treatment instrument swing stand 14 is inverted, if the clamp forceps 43 are projected by approximately 15 mm from the distal face 36, a clamp forceps image 43a appears in a view image. When the inverted second treatment instrument swing stand 14 is raised to an uppermost raised state, a clamp forceps image 43b appears. At this time, the tips of the clamp forceps 43 are visualized to exceed a centerline 55 that bisects the view image in the upward and downward directions thereof. Anyhow, the clamp forceps image moves within the view image.

When the first treatment instrument swing stand 15 is in a neutral state or is swung neither rightwards nor leftwards, if the cutting instrument 54 is projected by approximately 15 mm from the distal face 36, a cutting instrument image 54e is displayed. When the first treatment instrument swing stand 15 in the neutral state is swung leftwards and brought to a leftmost swung state, a cutting instrument image 54c is displayed.

When the first treatment instrument swing stand 15 in the neutral state is swung rightwards and brought to a rightmost swung state, a cutting instrument image 54d is displayed. At this time, the tip of the cutting instrument 54 is caught in the depth of field offered by the observation optical system 11 and visualized to move in the rightward and leftward directions of a view image around the centerline 55 that bisects the view image in the upward and downward directions thereof.

In other words, according to the present embodiment, when the first treatment instrument swing stand 15 is brought to the neutral state and the cutting instrument 54 is projected by approximately 15 mm, the tip of the treatment instrument is visualized like the cutting instrument image 54e to reach the centerline 55 that bisects the view image in the upward and downward directions of the view image.

Incidentally, the distance by which the tip of the treatment instrument is projected from the distal face is not limited to approximately 15 mm but may be any value (within the value of the depth of field) causing no obstacle to observation through the observation optical system 11. When the treatment instrument 44 is projected by a predetermined dimension, which falls within the value of the depth of field, from the distal face, the image of the treatment instrument reaches the centerline 55 that bisects the view image screen 41 in the upward and downward directions thereof.

Owing to the foregoing structure, when the treatment like the one shown in FIG. 8 to FIG. 10 is performed, the tip of a treatment instrument can be introduced to the center of a field of view being observed. Moreover, the distal part of the treatment instrument can be moved over a wide range substantially along the centerline that bisects a view image in the upward and downward directions thereof. Consequently, a procedure such as mucosal resection can be reliably and efficiently performed on a lesion over a wide range. Moreover, since it is easy to manipulate a treatment instrument, a surgical procedure can be achieved reliably and swiftly. This leads to minimized loads on an operator and a patient alike.

In other words, a treatment instrument is positioned around the center of a field of view, and a procedure such as mucosal resection can be easily performed on a lesion over a wide range by manipulating the treatment instrument once. This leads to improved maneuverability.

Incidentally, as a variant of the second embodiment, for example, the first treatment instrument swing stand 15 may be disposed below the observation window 3 so that a treatment instrument projected from the first treatment instrument swing stand 15 will enter a field of view from below.

Figure 19:
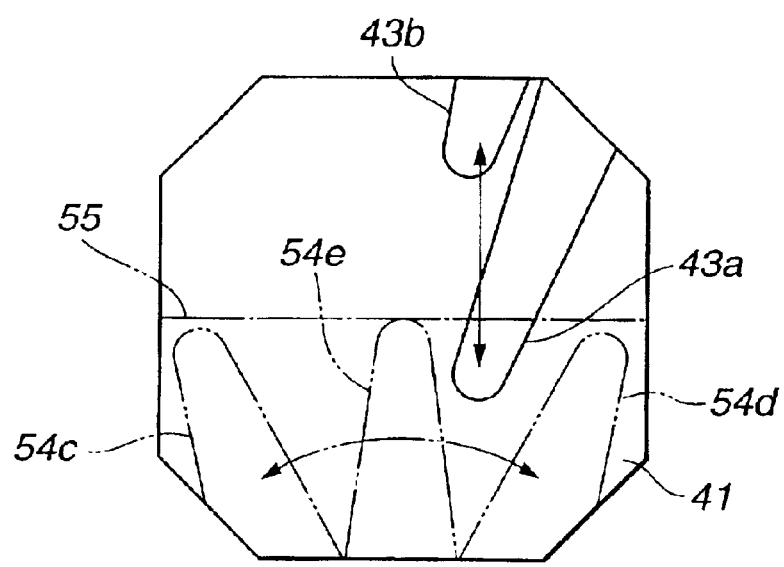

To be more specific, when the treatment instrument swing stands 14 and 15 are swung, the images of the treatment instruments may be moved in a view image as shown in FIG. 19.

Referring to FIG. 19, the clamp forceps images 43a and 43b are the lateral reversals of the images 43a and 43b shown in FIG. 18. The cutting instrument images 54c to 54e are the vertical reversals of the images 54c to 54e shown in FIG. 18.

In short, according to the variant, the first treatment instrument swing stand 15 is disposed below the observation window 3, and the second treatment instrument swing stand 14 is disposed by the right side of the observation window 3 operations and advantages to be exerted and provided by the present variant are nearly identical to those of the second embodiment.

Next, a third embodiment of the present invention will be described with reference to FIG. 20 and FIG. 21.

An endoscope of the third embodiment has nearly the same features as the endoscope shown in FIG. 1 to FIG. 6. Differences alone will be described below.

As mentioned above, assume that the treatment instrument 44 is projected from the inclined face 2a that is the distal face of the distal hard member 2 in order to resect a mucosa. In this case, the treatment instrument 44 is projected by approximately 15 mm that is neither a too short distance nor a too long distance but a distance permitting an operator to manipulate the treatment instrument most easily. The second angling wire 24 and third angling wire 25 are manipulated in order to swing the first treatment instrument swing stand 15. This causes the treatment instrument 44 to trace a trajectory as shown in FIG. 6. In FIG. 6, the treatment instrument 44 is projected rightwards and then swung leftwards. A description will be made on the assumption that the treatment instrument is brought to a neutral state and then swung rightwards or leftwards.

When the wire 24 and 25 are not pulled and the treatment instrument is in the neutral state, the treatment instrument 44 projecting through the opening 19a of the treatment instrument passage hole 19 is positioned as indicated with a solid line. Thereafter, when the wires 24 and 25 are pulled, the treatment instrument swing stand is swung so that the opening 19a will be oriented extremely rightwards or extremely leftwards. Consequently, the opening 19a moves to a position indicated with an alternate long and two short dashes line. At this time, the treatment instrument 44 located at the bottom 49 of the opening swings while being away from an opening rim 56 of the distal hard member 2.

When the treatment instrument 44 must be projected through the opening 19a, the treatment instrument 44 is projected from the inclined face 2a that is the distal face of the distal hard member 2 by, for example, approximately 15 mm that is neither a too short distance nor a too long distance but a distance permitting an operator to manipulate the treatment instrument most easily so as to resect a mucosa. In this state, the second angling wire 24 and third angling wire 25 are manipulated in order to swing the first treatment instrument swing stand 15. Consequently, the distal part of the treatment instrument 44 is, as shown in FIG. 6, moved without exceeding the right and left edges of a field of view for observation spread ahead of the observation window 3.

Figure 20:
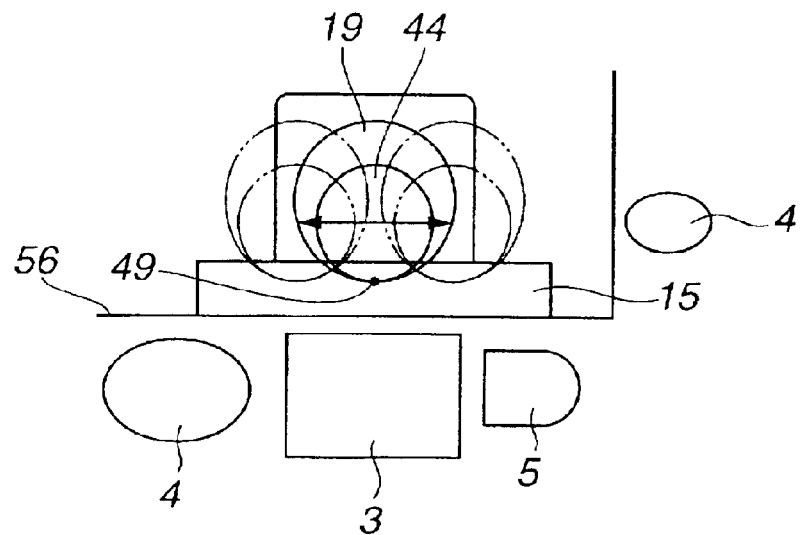
FIG. 20 and FIG. 21 are concerned with a third embodiment of the present invention.
Figure 21:
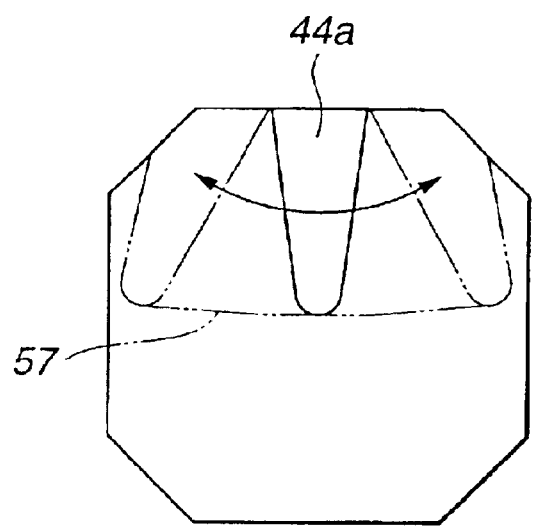

As described in conjunction with FIG. 20, when the treatment instrument is swung rightwards or leftwards from the neutral state, the treatment instrument image 44a contained in an endoscopic image swings from the neutral state indicated with a solid line in the rightward or leftward direction of the endoscopic image as indicated with solid-line arrows. At this time, the tip of the treatment instrument traces a tip trajectory 57 indicated with an alternate long and two short dashes line.

Incidentally, the tip trajectory 57 traced by the treatment instrument 44 curves upwards as the image of the treatment instrument 44 approaches the right or left edge of the endoscopic image. This is because the distances L1, L2 and L3 from the observation window 3 shown in FIG. 6 have the relationship expressed below.

L2 (or L3)<L1

The treatment instrument image 44a of the treatment instrument appears to project substantially from the upper margin of the screen. This is because the first treatment instrument swing stand 15 is disposed above the upper side 3u of the observation window 3.

Operations to be exerted by the present embodiment are nearly identical to those described in conjunction with FIG. 8 to FIG. 10.

According to the present embodiment, the distal trajectory 57 traced by the cutting instrument 44 curves upwards as the image of the cutting instrument 44 approaches the right or left side of an endoscopic image. Therefore, even if the treatment instrument image 44a of the cutting instrument 44 is swung at the right or left edge of the endoscopic image, the cutting edge of the cutting instrument will not deeply cut a region to be treated.

Furthermore, as described in conjunction with FIG. 8 to FIG. 10, assume that the mucosa of a lesion is lifted and the root thereof is resected using the cutting instrument 44. In this case, since the root spreads downwards, if the cutting instrument 44 is swung horizontally, the cutting instrument 44 curves upwards as it approaches the terminals in the horizontal directions. Therefore, the cutting instrument 44 will not cut the lesion too deeply.

Referring to FIG. 22 to FIG. 31, a fourth embodiment of the present invention will be described below.

Figure 22:
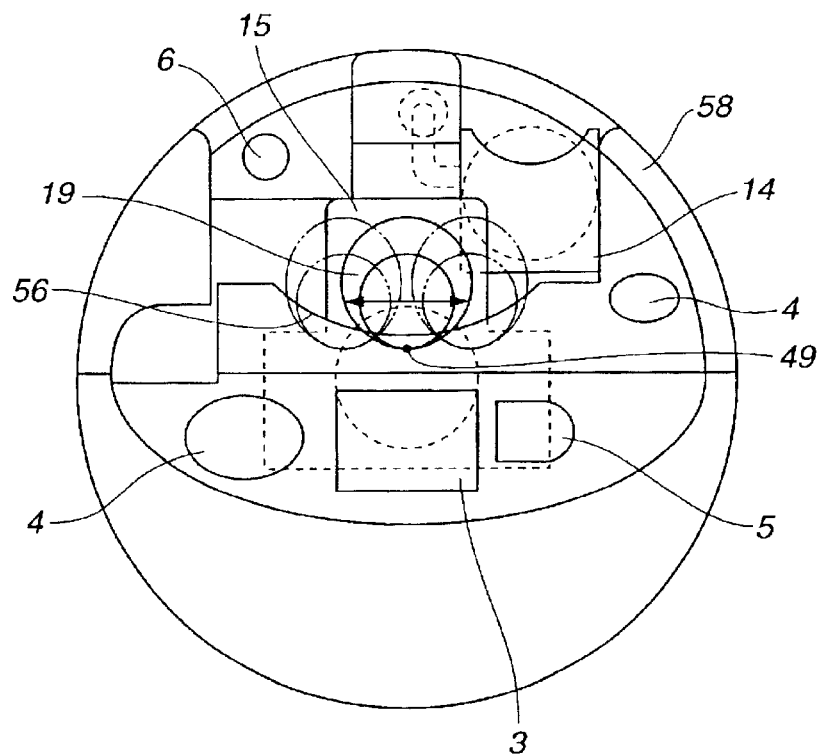
FIG. 22 to FIG. 31 are concerned with a fourth embodiment of the present invention.

According to the present embodiment, as shown in FIG. 22, the opening rim 56 of the distal component assembly 2 including an insulating cover 58 is realized with an arc-shaped curved surface. When the first treatment instrument swing stand 15 is swung, a trajectory the bottom 49 of the opening 19a traces runs below the opening rim 56.

Figure 23:
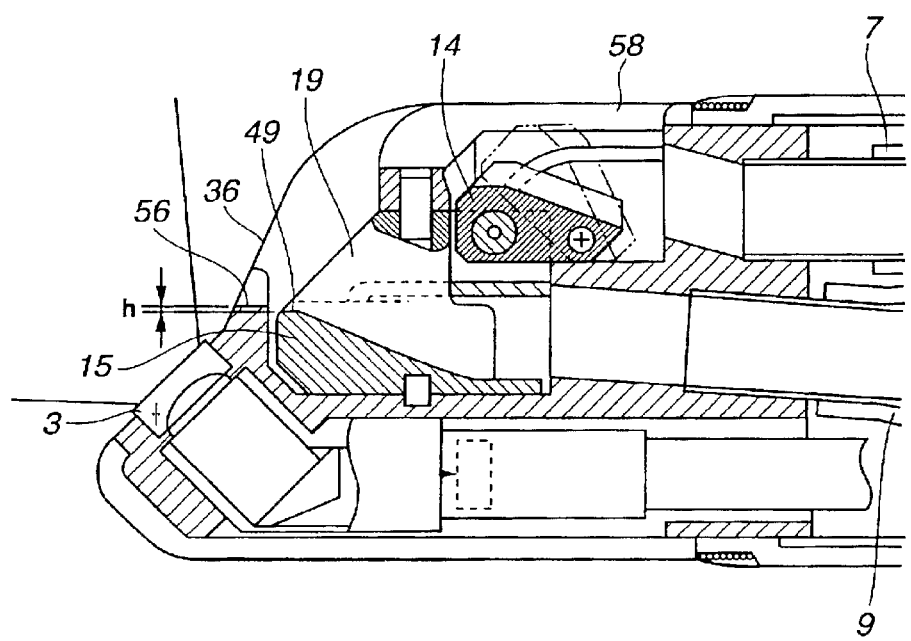
Figure 24:
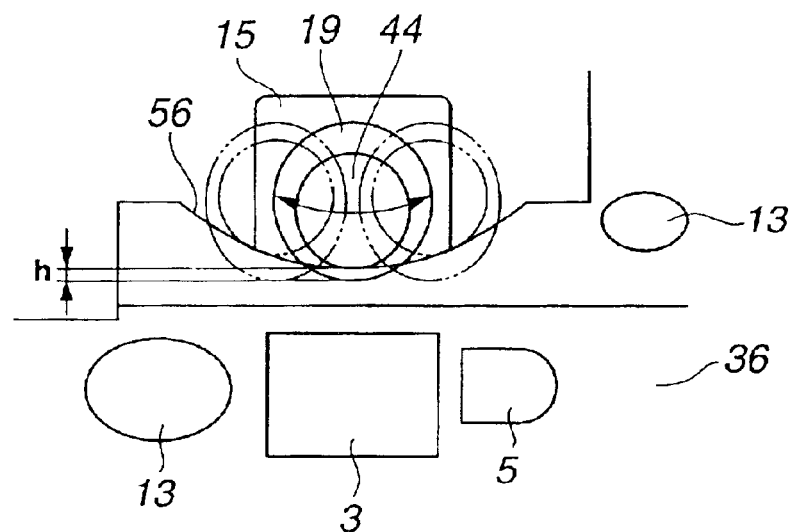

In other words, as shown in FIG. 23, the opening bottom 49 is sunk by a dimension h than the opening rim 56. Consequently, when the first treatment instrument swing stand 15 is swung, the opening 19a swings in the rightward and leftward directions of the endoscope in the same manner as the one included in the second embodiment. However, the cutting instrument 44 projecting through the opening 19a moves along the arc-like curved surface of the opening rim 56.

Figure 25:
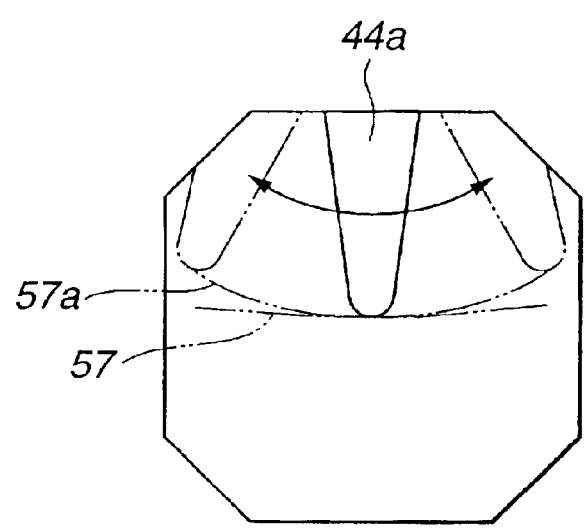

Consequently, for example, assume that the treatment instrument 44 is projected from the distal face 36, which contains the observation window 3, by a predetermined magnitude, and that the first treatment instrument swing stand 15 is swung. In this case, as shown in FIG. 25, a tip trajectory 57a draws a larger curve than the tip trajectory 57 drawn in the second embodiment, and moves up as the image of the first treatment instrument approaches the right and left edges of an endoscopic image.

At this time, similarly to the second embodiment, the tip of the treatment instrument 44 will not exceed the right and left edges of the endoscopic image by all means. The other features are identical to those of the second embodiment. The same reference numerals are assigned to the same members, and the description of the members is omitted.

As mentioned above, the treatment instrument is moved along the arc-like curved surface of the opening rim. Consequently, the tip trajectory traced by the treatment instrument draws a large curve on an endoscopic image as the image of the treatment instrument approaches the right or left edge of the endoscopic image. Herein, the curve rises up within a field of view. Even when the cutting instrument swings at a position corresponding to the right or left edge of the endoscopic image, the cutting edge thereof is reliably prevented from deeply cutting a region to be treated.

Moreover, since the tip trajectory traced by the treatment instrument is largely curved upwards as the image of the treatment instrument approaches the right or left edge of an endoscopic image, the width of a cutting surface in the rightward and leftward directions of the endoscope is narrower than it is in the second embodiment.

Furthermore, since the treatment instrument is turned and swung rightwards and leftwards, a lesion can be cut clearly.

In the structure shown in FIG. 22 and FIG. 23 and employed in the present embodiment, the opening bottom 49 runs below the opening rim 56 over the entire swingable range of the first treatment instrument swing stand 15. Alternatively, the opening bottom 49 and opening rim 56 may have substantially the same height near the center of the observation window 3.

Moreover, the distal face 36 of the distal part 1 may not be planar but may be shaped differently, that is, may be shaped like a concave curved surface.

Figure 26:
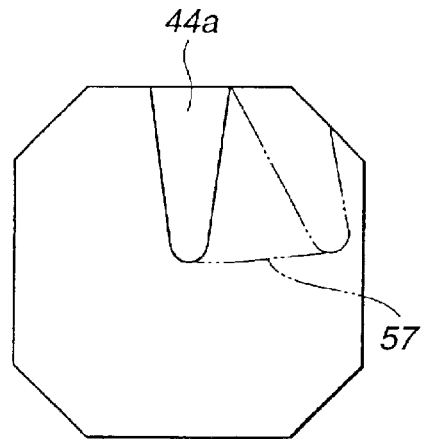

Furthermore, the swingable range of the first treatment instrument swing stand 15 may not cover the swings in the rightward and leftward directions with respect to the screen centerline. Alternatively, as shown in FIG. 26, the swingable range of the first treatment instrument swing stand 15 observed in an endoscopic image may cover the swing in one direction with respect to the screen centerline.

Figure 27:
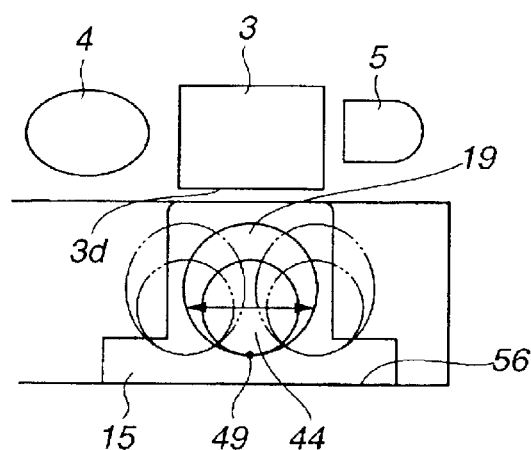
Figure 28:
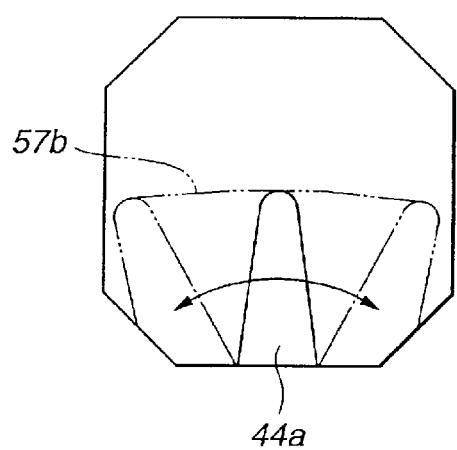

Moreover, the first treatment instrument swing stand 15 may be disposed below the lower side 3d of the observation window 3 as shown in FIG. 27 that shows the position of the first treatment instrument swing stand relative to the observation window.

However, at this time, if the positional relationship between the opening bottom 49 and opening rim 56 is as shown in FIG. 27, the treatment instrument image 44a of the treatment instrument 44 projects from substantially the lower margin of the screen. Moreover, the tip trajectory 57b traced by the treatment instrument 44 curves downwards as the image of the treatment instrument approaches the right or left edge of the endoscopic image.

Figure 29:
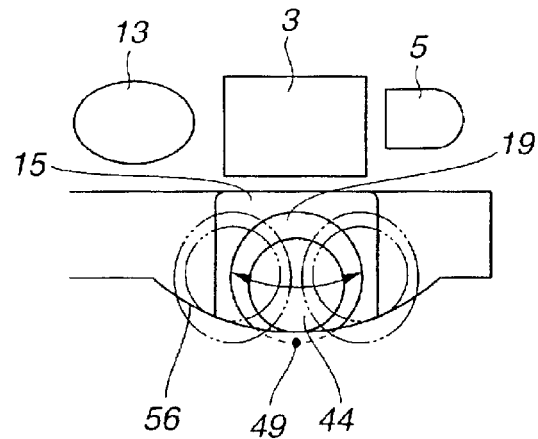

FIG. 29 is an explanatory diagram concerning the opening of the treatment instrument passage hole and the swing of the treatment instrument that projects through the opening. As shown in FIG. 29, the opening rim 56a is realized with an ark-like curved surface, and the opening bottom 49 of the opening 19a runs below the opening rim 56 over the entire swingable range of the first treatment instrument swing stand 15.

Figure 30:
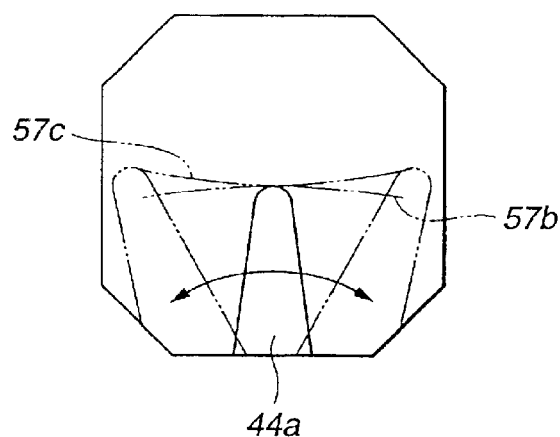

Consequently, as shown in FIG. 30 that is an explanatory diagram showing an image of a treatment instrument displayed on a TV monitor, the image of the tip of the cutting instrument 44 will not exceed the right and left edges of an endoscopic image by all means. The tip trajectory 57c of the treatment instrument is, similarly to the ones in the second and third embodiments, curved upwards as the image of the treatment instrument approaches the right or left edges of the endoscopic image. Consequently, the same operations and advantages as those of the aforesaid embodiments can be exerted and provided.

Figure 31:
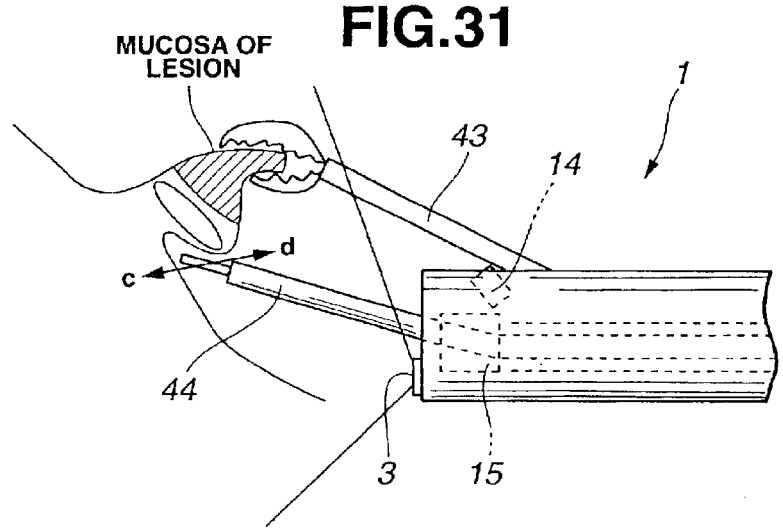

Furthermore, the observation optical system is not limited to an oblique-vision type. As shown in FIG. 31 that shows a direct-vision endoscope having a second treatment instrument swing stand and a first treatment instrument swing stand, the observation optical system may be of a direct-vision type or a side-vision type. Moreover, the aforesaid observation window may be circular.

Next, referring to FIG. 32 to FIG. 34, a fifth embodiment of the present invention will be described below. The present embodiment has nearly the same features as the first embodiment. Differences alone will be described below.

According to the present embodiment, as shown in FIG. 2 and others, the first treatment instrument swing stand 15 is disposed above (the upper side 3u of) the observation window 3.

Moreover, as shown in FIG. 2, the opening centerline 28 bisects the opening 19a of the treatment instrument passage hole 19 in the rightward and leftward directions of the endoscope. The channel centerline 29 bisects the first channel opening portion 10 in the rightward and leftward directions. The field-of-view centerline 27 bisects the observation window 3 in the rightward and leftward directions. The opening centerline 28, channel centerline 29, and field-of-view centerline 27 are contained substantially in the same plane. Alternatively, the opening centerline 28, field-of-view centerline 27, and channel centerline 29 may be contained substantially in the same plane near the centerline that bisects the distal part in the rightward and leftward directions.

Figure 32:
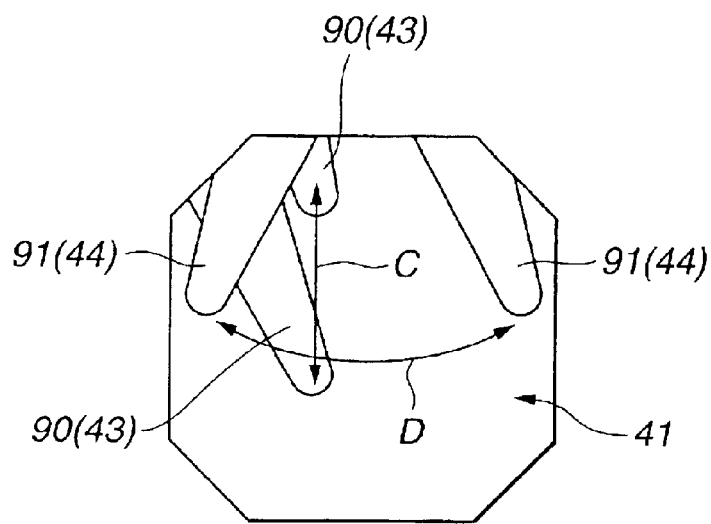
FIG. 32 to FIG. 34 are concerned with a fifth embodiment of the present invention.

Consequently, in whatever state the treatment instrument swing stands 14 and 15 are placed, when treatment instruments are projected through the openings 8a and 19a respectively, an image 91 of one treatment instrument appears, as shown in FIG. 32, to project substantially from the upper margin of the screen 41 of a display device, for example, the TV monitor 53. This is because the first treatment instrument swing stand 15 is disposed above the upper side 3u of the observation window 3.

When the second treatment instrument swing stand 14 is swung, an image 90 of the second treatment instrument projected through the second channel opening 8a moves substantially in the upward and downward directions of the screen 41 as indicated with arrows C. When the first treatment instrument swing stand 15 is swung, the first treatment instrument image 91 of the first treatment instrument projected through the opening 19a moves substantially in the rightward and leftward directions of the screen 41 as indicated with arrows D.

As seen from FIG. 32, when the second treatment instrument image 90 and first treatment instrument image 91 are displayed, if the second and first treatment instruments are projected vertically by approximately 15 mm, the tips of the treatment instruments will not exceed the right, left, upper, and lower edges of the field of view for observation. Therefore, an operator can easily imagine trajectories the tips of the treatment instruments will trace along with the swings of the treatment instrument swing stands 14 and 15.

As mentioned above, according to the present embodiment, the second treatment instrument swing stand 14 and the first treatment instrument swing stand 15 are swung in different directions. Moreover, the second treatment instrument swing stand 14 and the first treatment instrument swing stand 15 are disposed above the observation window 3.

Operations to be exerted by the endoscope having the foregoing features will be described below.

First, as shown in FIG. 8, the observation window 3 included in the distal part 1 of the insertion unit 40 is opposed to the mucosa of a lesion. The mucosa of the lesion is observed through the endoscope. Moreover, for example, the injection needle 42 that is a treatment instrument is passed through the first treatment instrument passage channel 9 and thus introduced into a body cavity. Herein, the first treatment instrument swing stand 15 is swung in order to oppose the injection needle 42 to the mucosa of the lesion. Thus, the injection needle 42 is opposed to a predetermined region on the mucosa of the lesion, and advanced to an intended region as indicated with arrow a. Physiological saline or any other medicine is then injected into the substratum of the mucosa of the lesion. This causes the tunica mucosa including the mucosa of the lesion to swell.

Thereafter, as shown in FIG. 9, the clamp forceps 43 that are a treatment instrument are passed through the second treatment instrument passage channel 7 and thus introduced into the body cavity. Herein, the second treatment instrument swing stand 14 is swung in order to oppose the clamp forceps 43 to the swelled tunica mucosa. When the clamp forceps 43 are opposed to a predetermined region on the tunica mucosa, the clamp forceps 43 are thrust forwards in order to clamp the tunica mucosa including the swelled mucosa of the lesion. Meanwhile, the cutting instrument 44 that is a treatment instrument is inserted into the first treatment instrument passage channel 9 on behalf of the injection needle 42 and disposed near the mucosa of the lesion.

Thereafter, the second treatment instrument swing stand 14 is swung in order to raise the clamp forceps 43 in the direction of arrow b. Consequently, the tunica mucosa including the mucosa of the lesion and being clamped by the clamp forceps 43 is lifted.

The first treatment instrument swing stand 15 is, as shown in FIG. 10, then swung in the directions of arrows c and d, whereby the substratum of the swelled mucosa is resected using the cutting instrument 44. At this time, the second treatment instrument swing stand 14 is disposed above the first treatment instrument swing stand 15 and the first treatment instrument swing stand 15 is disposed above the observation window 3. Therefore, with the mucosa of the lesion lifted, the root of the mucosa of the lesion can be resected swiftly while being caught in the field of view for observation. Meanwhile, care is given to the situation of a cutting surface, for example, the depth of the cutting edge of the cutting instrument 44 that is observed through the observation window 3.

In other words, the mucosa of the lesion is held lifted, and a portion of the root thereof to be incised is caught in the field of view for observation and incised using the cutting instrument 44 projected by means of the first treatment instrument swing stand 15. In this case, the cutting instrument 44 enters the field of view for observation from the upper edge thereof. The portion to be incised with the cutting edge of the cutting instrument 44 can therefore be caught in the field of view. Thus, incision can be proceeded. Moreover, even when incision is in progress, incision can be performed with the cutting edge of the cutting instrument caught in the field of view. In this case, when the cutting instrument 44 enters the field of view from the lower edge thereof, it is hard to catch the apex of the portion incised with the cutting instrument 44 in the field of view.

According to the present invention, in addition to the same advantages as those of the first embodiment, such an advantage is provided that: since the first treatment instrument swing stand 15 that swings the distal part of a treatment instrument in the rightward and leftward directions of the endoscope is disposed above the observation window 3, the distal part of the treatment instrument can be caught in the field of view for observation. This leads to improved maneuverability.

Moreover, the treatment instrument swing stands that swing in different directions are disposed at predetermined positions near the openings of two treatment instrument passage channels, which run through the endoscope, within the distal part of the endoscope. Different treatment instruments introduced into a body cavity by way of the treatment instrument passage channels can be smoothly moved over a wide range by manipulating proximal members. Consequently, a desired procedure can be reliably and easily achieved.

For example, when a lesion must be resected, although the procedure is performed using an endoscope, an operator can achieve the endoscopic procedure as if to hold the clamp forces with his/her one hand and to hold the cutting instrument with the other hand. Moreover, unlike the related art, the distal part of the endoscope need not be moved or angled for the purpose of resection of a lesion. An object can be properly caught in the field of view for observation all the time.

Moreover, when a treatment instrument is introduced into a body cavity by way of a treatment instrument passage channel and imaged by the observation optical system, the image of the treatment instrument appears to project from the upper margin of the screen of a display device all the time. Therefore, the positional relationship between the treatment instrument and a region to be observed and a movable range of the treatment instrument can be grasped readily and utilized for a procedure.

Consequently, when the endoscope is used in combination with treatment instruments that are accessories of the endoscope, the whole of a lesion spread widely can be resected reliably and easily at a time. Moreover, since the treatment instruments can be manipulated easily, a surgical procedure can be performed reliably and swiftly. This leads to reduced loads on an operator and a patient alike.

Incidentally, after the cutting instrument 44 is introduced into a body cavity by way of the second treatment instrument passage channel 7 and the clamp forceps 43 are introduced into the body cavity by way of the first treatment instrument passage channel 9, the position of the distal part of the endoscope relative to the mucosa of the body cavity may be adjusted. Thus, resection can be achieved in the same manner as the aforesaid one.

Figure 33:
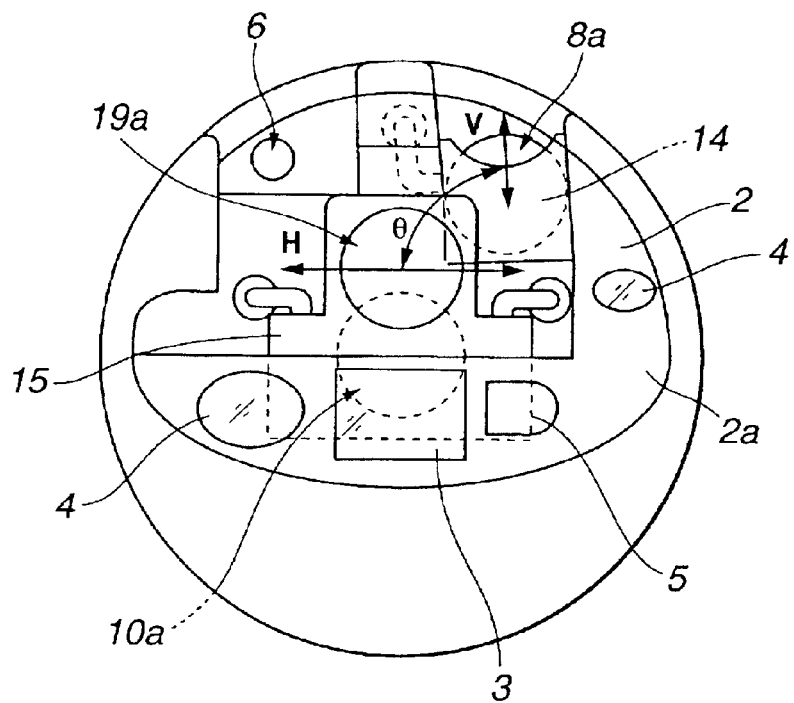

FIG. 33 is an explanatory diagram showing an example of the arrangement of components contained in the distal face of a first variant. As shown in FIG. 33, according to the present variant, the swingable directions V in which the second treatment instrument swing stand 14 can swing are defined obliquely relative to the centerline of a field of view.

To be more specific, for example, a treatment instrument to be swung by the second treatment instrument swing stand 14, a treatment instrument to be swung by the first treatment instrument swing stand 15, and a liquid to be sprayed through the forward water outlet 6, for example, water have such a positional relationship as to substantially cross near the centerline of a field of view seen by an operator at a distance of 15 mm from the distal face 2a. Thus, an angle θ at which the swingable directions V in which the second treatment instrument swing stand 14 can swing and the swingable directions H in which the first treatment instrument swing stand 15 can swing meets is not 90°. The other features are identical to those of the present embodiment. The same reference numerals are assigned to the identical members, and the description of the members is omitted.

As mentioned above, the direction in which a treatment instrument is projected from the second treatment instrument swing stand 14 is aligned with the field-of-view centerline that bisects the field of view in the rightward and leftward directions of the endoscope. Consequently, in addition to the same advantages as those of the present embodiment, such an advantage is provided that a treatment instrument to be swung by the second treatment instrument swing stand 14 is displayed in the center of the screen. This leads to further improved maneuverability.

Figure 34:
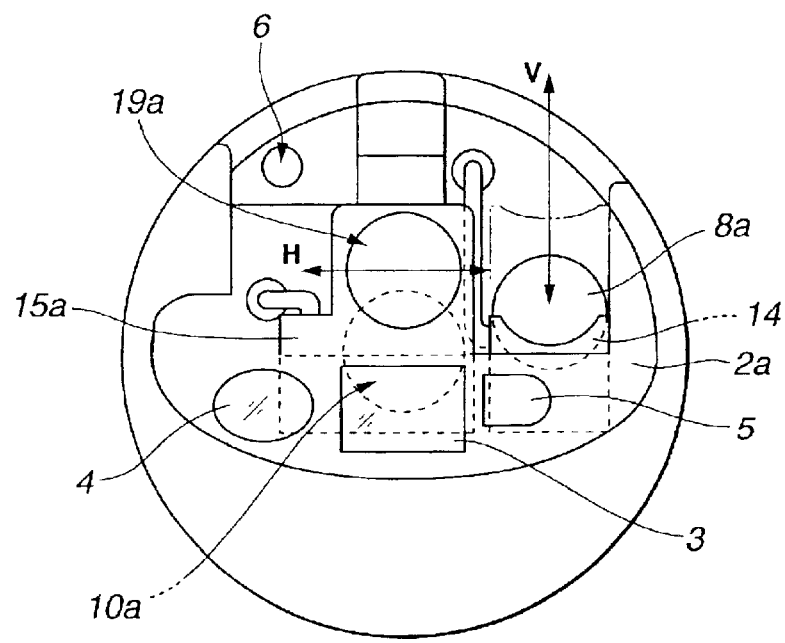

Furthermore, FIG. 34 is an explanatory diagram showing an example of the arrangement of components contained in the distal face of a second variant.

As shown in FIG. 34, according to the present variant, the second treatment instrument swing stand 14 is disposed adjacently to a first treatment instrument swing stand 15*a*. When the second treatment instrument swing stand 14 is inverted completely, a treatment instrument swung by the second treatment instrument swing stand 14 is located below a treatment instrument swung by the first treatment instrument swing stand 15*a*.

As the second treatment instrument swing stand 14 is raised gradually, the treatment instrument swung by the second treatment instrument swing stand 14 comes to lie above the treatment instrument swung by the first treatment instrument swing stand 15*a*.

As mentioned above, the second treatment instrument swing stand 14 is disposed adjacently to the first treatment instrument swing stand 15*a*. Consequently, in addition to the same advantages as those of the present embodiment, such an advantage is provided that the swingable range of the second treatment instrument swing stand 14 adjoining the first treatment instrument swing stand 15*a* to be widened. Eventually, the relationship between two treatment instruments to be swung can be changed in order to perform different endoscopic procedures.

Incidentally, the first treatment instrument swing stand 15*a* included in the present variant is shaped substantially like letter L when seen from the distal face. The first treatment instrument swing stand 15*a* is swung relative to the distal hard member 2 by manipulating one angling wire.

Next, referring to FIG. 35 to FIG. 51, a sixth embodiment of the present invention will be described below.

Figure 35:
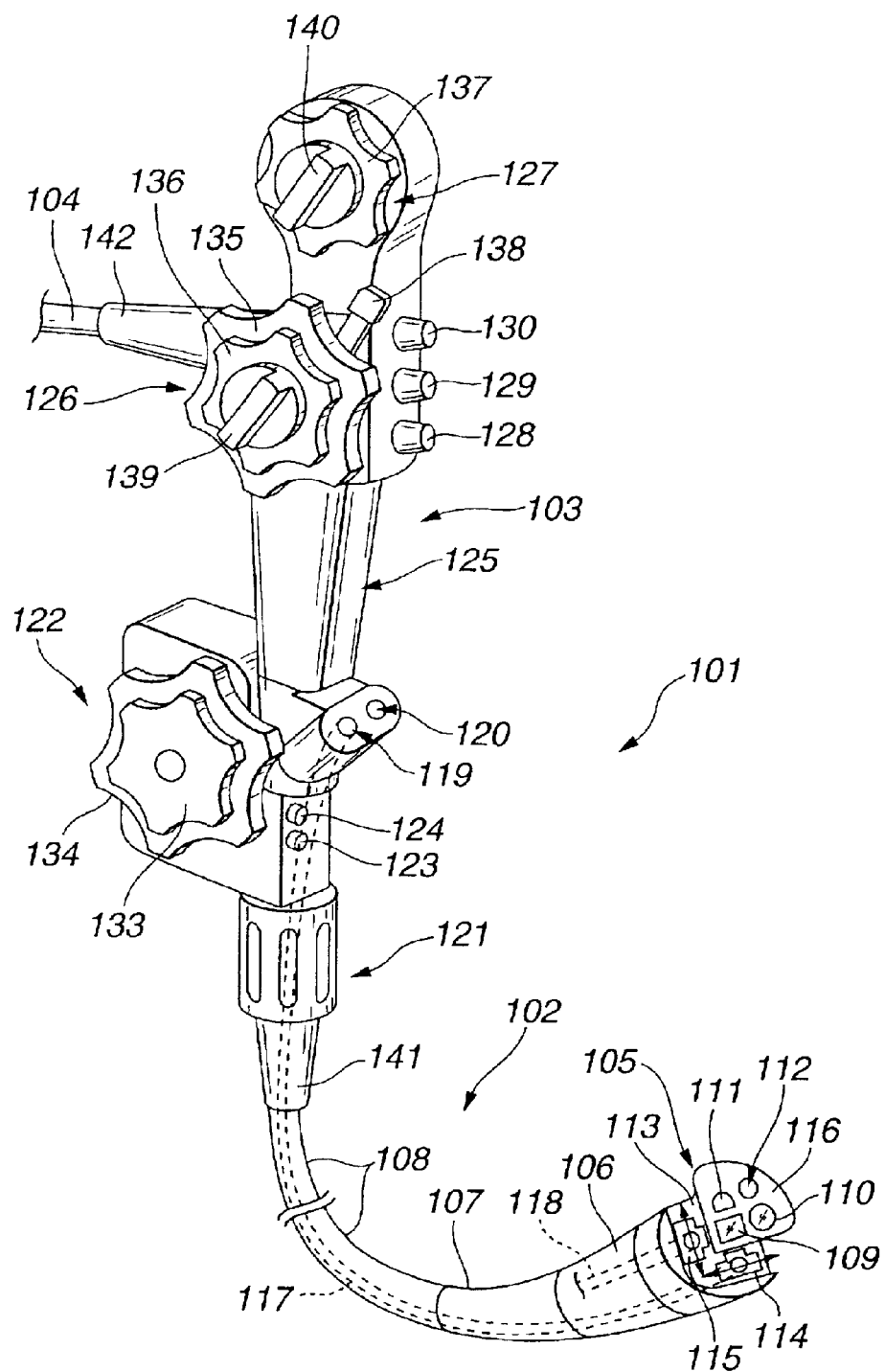

As shown in FIG. 35, an endoscope 101 of the present embodiment includes an insertion unit 102 and an operation unit 103. A light guide and a universal cord 104 containing a cable that is routed to an imaging device which is not shown are led out of the flank of the operation unit 103.

The terminal end of the universal cord 104 is routed to a light source apparatus and a CCU serving as a signal processing unit. Herein, both the light source apparatus and CCU are not shown. A view image picked up by an imaging device is displayed on a view image display screen portion of the display surface of a monitor connected to the CCU.

Figure 36:
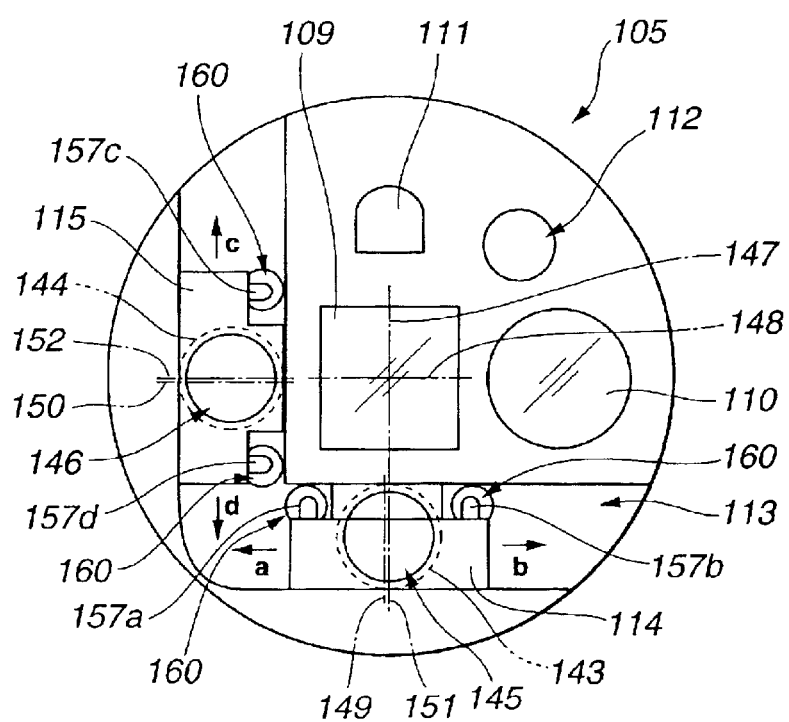
FIG. 35 to FIG. 51 are concerned with a sixth embodiment of the present invention.

The insertion unit 102 has a distal part 105, a first bending section 106, a second bending section 107, and a flexible tube 108 joined in that order from the distal end thereof. The distal face of the distal part 105 contains, as shown in FIG. 36, an observation window 109, an illumination window 110, an air/water supply nozzle 111, and a forward water outlet 112.

Moreover, the distal part 105 includes a treatment instrument swing stand storage member 113 in which a second treatment instrument swing stand 114 and a first treatment instrument swing stand 115 are placed so that they can swing freely. The second treatment instrument swing stand 114 swings substantially in the rightward and leftward directions of the endoscope with a field of view spread ahead of the observation window 109. The first treatment instrument swing stand 115 swings substantially in the upward and downward directions of the endoscope with the field of view spread ahead of the observation window 109.

The external surface of the distal part is covered with an insulating member 116. The swing stand storage member 113 partly opens upon the distal face of the distal part 105 and the flank thereof. This obviates the necessity of increasing the diameter of the distal part 105 and results in the wide swingable ranges of the second treatment instrument swing stand 114 and first treatment instrument swing stand 115. Furthermore, the second treatment instrument swing stand 114 and first treatment instrument swing stand 115 are formed with electrically insulating members made of a ceramic or the like, stainless members coated with an electrically insulating film, or mere stainless members.

The first bending section 106 can be bent substantially in the upward and downward directions of the endoscope and the rightward and leftward directions thereof with the field of view spread ahead by manipulating a first angling member 126 included in the operation unit 103. On the other hand, the second bending section 107 can be bent substantially in the upward and downward directions of the endoscope with the field of view spread ahead by manipulating a second angling member 127. The first bending section 106 and second bending section 107 are bent independently of each other. Angles at which the first bending section 106 can be bent in the upward, downward, rightward, and leftward directions are set to, for example, 210°, 180°, 100°, and 100° respectively. Angles at which the second bending section 107 can be bent in the upward and downward directions are set to, for example, 90° and 90° respectively. Consequently, a lesion can be observed from a point in front thereof, and treated.

A first treatment instrument passage channel 117 and a second treatment instrument passage channel 118 are run through the insertion unit 102. The distal opening of the first treatment instrument passage channel 117 communicates with the first treatment instrument swing stand 114, while the proximal opening thereof communicates with a first treatment instrument inlet 119 formed in the operation unit 103.

On the other hand, the distal opening of the second treatment instrument passage channel 118 communicates with the second treatment instrument swing stand 115, while the proximal opening thereof communicates with a second treatment instrument inlet 120 formed in the operation unit 103. Hereinafter, a treatment instrument to be passed through the first treatment instrument passage channel 117 shall be called a first treatment instrument 153, and a treatment instrument to be passed through the second treatment instrument passage channel 118 shall be called a second treatment instrument 154.

The operation unit 103 is composed mainly of an insertion unit rotator 121, a swing stand manipulator 122, a grip 125, the first angling member 126, and the second angling member 127.

The insertion unit rotator 121 is designed to rotate together with the insertion unit 102. By twisting the insertion unit rotator 121, the insertion unit 102 is turned with the swing stand manipulator 122 and grip 125 left intact.

Referring to FIG. 37 to FIG. 40, the structure of the insertion unit rotator 121 will be described below.

A flexible tube termination member 166 is fixed to the proximal end of the flexible tube 108. An insertion unit anti-breakage member 141 is integrated with the flexible tube termination member 166. A tubular rotation ring structure 162 is integrated with the internal surface of a tubular rotation ring 161 that is a body of the insertion unit rotator 121. The flexible tube termination member 166 is fixed to the rotation ring structure 162.

Figure 3:
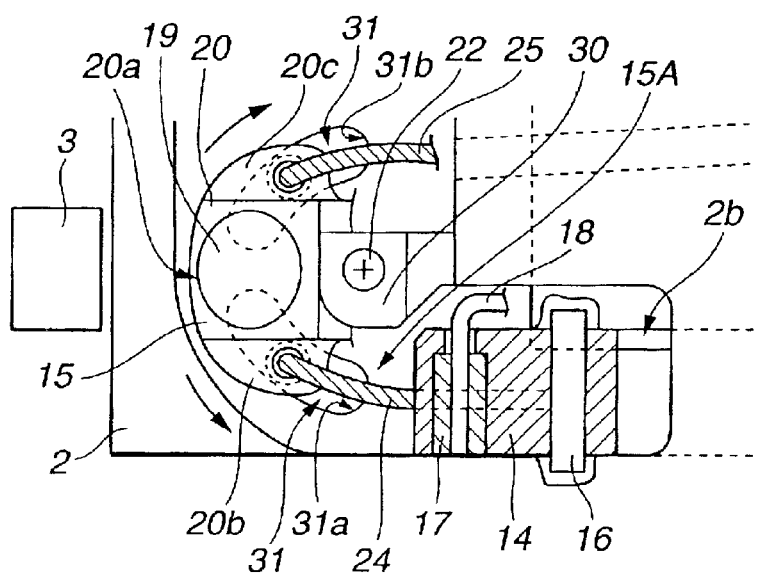

As shown in FIG. 3, a slit 163 that is elongated in a circumferential direction is formed in the periphery of the rotation ring structure 162. An irregular part 171 is, as shown in FIG. 39, formed circumferentially at the proximal end surface of the rotation ring 161.

Furthermore, a swing stand manipulator structure 164 that is an internal structure of the operation unit 103, or more specifically, of the swing stand manipulator 122 has a lock pin 165 that is fitted in the slit 163. The rotation ring structure 162 can rotate in circumferential directions while being guided by the lock pin 165 fitted in the slit 163.

In addition, a turn stopper structure that is a turned state maintaining structure for maintaining a turned state of the rotation ring 161 that is turned by a desired angle is incorporated in the distal part of an armor member 167 that proximally adjoins the rotation ring 161.

Figure 37:
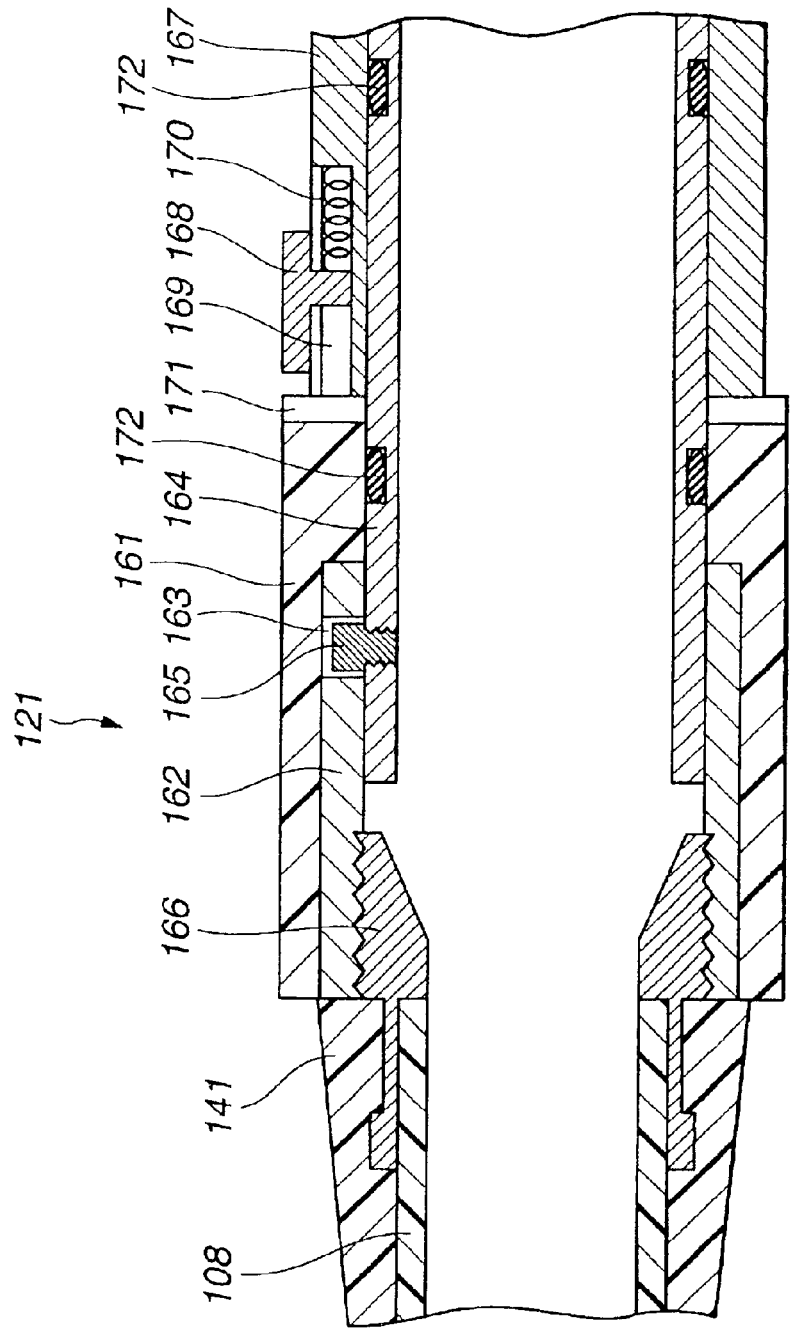
Figure 38:
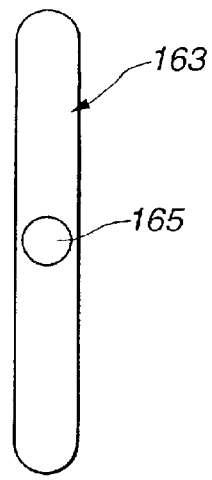
Figure 39:
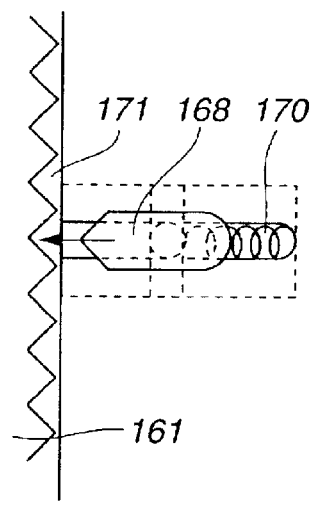
Figure 40:
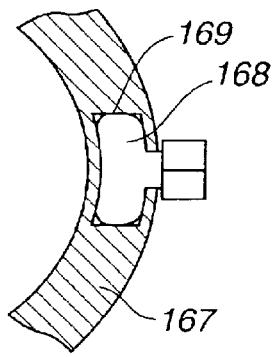

The turn stopper structure consists of, as shown in FIG. 37, FIG. 39, and FIG. 40, a turn/lock switching lever 168 that is held in a turn/lock switching lever storage member 169, which is formed at the end of the armor member 167, while being permitted to move, and a constraining member 170 incorporated in a space proximal to the turn/lock switching lever 168. With a constraining force exerted by the constraining member 170, the distal end of the turn/lock switching lever 168 is engaged with a concave part of the irregular part 171 in a natural state.

Incidentally, watertight members 172 are interposed between the swing stand manipulator structure 164 and the rotation ring 161, and between the swing stand manipulator structure 164 and armor member 167. Owing to the watertight members 172, the insertion unit rotator 121 is kept watertight in the same manner as the other portions of the operation unit are. An angle of rotation by which the rotation ring 162 can be turned clockwise and counterclockwise at maximum may be set to 180°.

Referring back to FIG. 35, the structure of the operation unit 103 will be described below.

The first angling member 126 associated with the first bending section 106 includes a first upward/downward angling knob 135, a rightward/leftward angling knob 136, a first upward/downward turn/lock lever 138, and a rightward/leftward turn/lock lever 139.

Upward/downward angling wires (not shown) extended from the first bending section 106 are coupled to the first upward/downward angling knob 135 within the first angling member 126 or the grip 125. Moreover, rightward/leftward angling wires (not shown) extended from the first bending section 106 are coupled to the rightward/leftward angling knob 136 within the first angling member 126 or the grip 125.

The turnable state of the first upward/downward angling knob 135 and the locked state thereof are switched using the first upward/downward turn/lock lever 138. The turnable state of the rightward/leftward angling knob 136 and the locked state thereof are switched using the rightward/leftward turn/lock lever 139.

The second angling member 127 associated with the second bending section 107 includes a second upward/downward angling knob 137 and a second upward/downward turn/lock knob 140. Upward/downward angling wires (not shown) extended from the second bending section 107 are coupled to the second upward/downward angling knob 137 within the second angling member 127 or the grip 125. The turnable state of the second upward/downward angling knob 137 and the locked state thereof are switched using a second upward/downward turn/lock knob 140.

Incidentally, an air/water supply control button 128, a suction control button 129, and an image control button 130 are disposed near the first angling member 126. Moreover, a universal cord anti-breakage member 142 is included for preventing breakage of the universal cord 104 at the root thereof.

A mechanism (not shown) for manipulating the first treatment instrument swing stand 114 and a mechanism (not shown) for manipulating the second treatment instrument swing stand 115 are incorporated in the swing stand manipulator 122.

Figure 41:
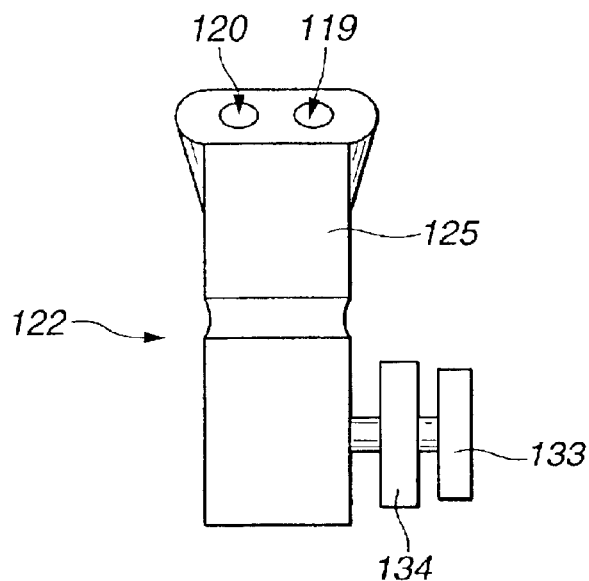

As shown in FIG. 35 and FIG. 41, a first treatment instrument swing stand manipulation knob 133 and a second treatment instrument swing stand manipulation knob 134 which are parts of the mechanisms are formed on the external surface of the swing stand manipulator 122. The first treatment instrument swing stand 133 and second treatment instrument swing stand 135 are disposed coaxially to each other below the first treatment instrument inlet 119 and second treatment instrument inlet 120 respectively.

By handling the first treatment instrument swing stand manipulation knob 133, the two associated angling wires 157a and 157b are alternately pulled. This remotely causes the first treatment instrument swing stand 114 to swing in the direction of arrow a and the direction of arrow b (the rightward and leftward directions) (see FIG. 36).

On the other hand, by handling the second treatment instrument swing stand manipulation knob 134, the two associated angling wires 157c and 157d are alternately pulled. This remotely causes the second treatment instrument swing stand 115 to swing in the direction of arrow c and the direction of arrow d (the upward and downward directions) (see FIG. 36).

A forward water supply inlet 123 and a swing stand angling wire cleansing port 124 are bored in the external surface of the swing stand manipulator 122. The swing stand angling wire cleansing port 124 opens upon the swing stand storage member 113. When a syringe that is not shown is connected to the endoscope, a cleansing solution or the like poured into the syringe is fed to the angling wire passage channels 160 in order to cleanse the angling wires. Moreover, the forward water supply inlet 123 is linked to the forward water outlet 112.

As shown in FIG. 36, the first treatment instrument swing stand 114 has a first treatment instrument passage hole 145 bored therein. The first treatment instrument passage hole 145 communicates with a first distal opening portion 143 of the first treatment instrument passage channel 117 which is indicated with a dashed line. Herein, a centerline 149 bisects the first distal opening portion 143. A centerline 151 drawn with a dot-dash line bisects the first treatment instrument passage hole 145, and meets the swingable directions of the first treatment instrument swing stand 114, in which the first treatment instrument swing stand 114 can swing, substantially at right angles.

On the other hand, a second treatment instrument passage hole 146 is bored in the second treatment instrument swing stand 115. The second treatment instrument passage hole 146 communicates with a second distal opening portion 144 of the second treatment instrument passage channel 118. Herein, a centerline 150 bisects the second distal opening portion 144. A centerline 152 drawn with a dot-dash line bisects the second treatment instrument passage hole 146, and meets the directions of swing, in which the second treatment instrument swing stand 115 swings, substantially at right angles.

Incidentally, a centerline 147 corresponds to a centerline that bisects a view image (that is, the screen 41 in FIG. 1) displayed on the monitor in the rightward and leftward directions of the screen, and is drawn on the observation window 109. A centerline 148 corresponds to a centerline that bisects the view image in the upward and downward directions of the screen, and is drawn on the observation window 109.

When the first passage hole centerline 151 and first opening portion centerline 149 are substantially aligned with each other, and the second passage hole centerline 152 and second opening portion centerline 150 are substantially aligned with each other, the treatment instrument swing stands 114 and 115 are not swung. When the first or second treatment instrument swing stand is not swung, it says that the first or second treatment instrument swing stand is located at a swing neutral position or placed in a swing neutral state.

When the first treatment instrument swing stand 114 is placed in the swing neutral state, the first passage hole centerline 151 and the centerline 147 that bisects a view image in the rightward and leftward directions are substantially aligned with each other. The first treatment instrument swing stand 114 is leveled with the observation window 109. Moreover, when the second treatment instrument swing stand 115 is placed in the swing neutral state, the second passage hole centerline 152 and the centerline 148 that bisects the view image in the upward and downward directions are substantially aligned with each other. The second treatment instrument swing stand 115 is leveled with the observation window 109. Namely, when the treatment instrument swing stands 114 and 115 are disposed as shown in FIG. 36, the treatment instrument swing stands 114 and 115 are both in the swing neutral states.

Figure 42:
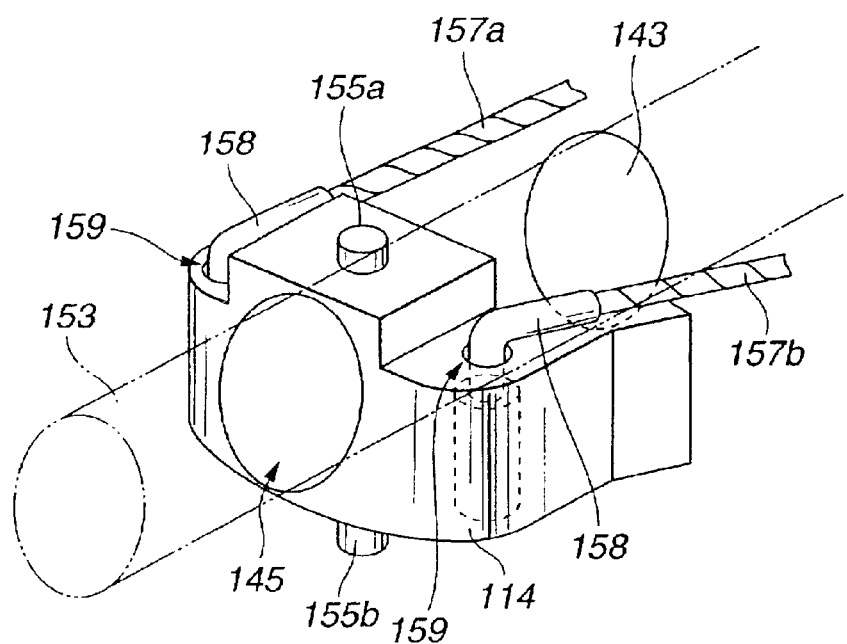

Referring to FIG. 42, swinging mechanism of the first treatment instrument swing stand 114 will therefore be described below. Since the swinging mechanism of the second treatment instrument swing stand 115 is identical to the swinging mechanism of the first treatment instrument swing stand 114, the description of the swinging mechanism of the second treatment instrument swing stand will be omitted.

As shown in FIG. 42, a first rotation shaft 155a and a second rotation shaft 155b are projected from the top of the first treatment instrument swing stand 114 and the bottom thereof with the first treatment instrument passage hole 145 between them. Moreover, attachment holes 159 are bored in both edges of the first treatment instrument swing stand 114 with the first rotation shaft 155a and second rotation shaft 155b between them. Wire termination members 158 fixed to the ends of the angling wires 157a and 157b are inserted in the attachment holes 159 so that they can rotate freely.

The first rotation shaft 155a and second rotation shaft 155b are disposed in the swing stand storage member 113 so that they can rotate freely. The two angling wires 157a and 157b are alternately pulled by handling the first treatment instrument swing stand manipulation knob 133. Consequently, the first treatment instrument swing stand 114 is swung in the rightward and leftward directions within the swing stand storage member 113 with the first rotation shaft 155a and second rotation shaft 155b, which are coaxial to each other, as a center of rotation.

Moreover, referring to FIG. 42, the first treatment instrument swing stand 114 is in the swing neutral state. Therefore, the first treatment instrument 153 indicated with an alternate long and two short dashes line and inserted into the first treatment instrument passage channel 117 is projected substantially straight to outside through the first treatment instrument passage hole 145.

Figure 43:
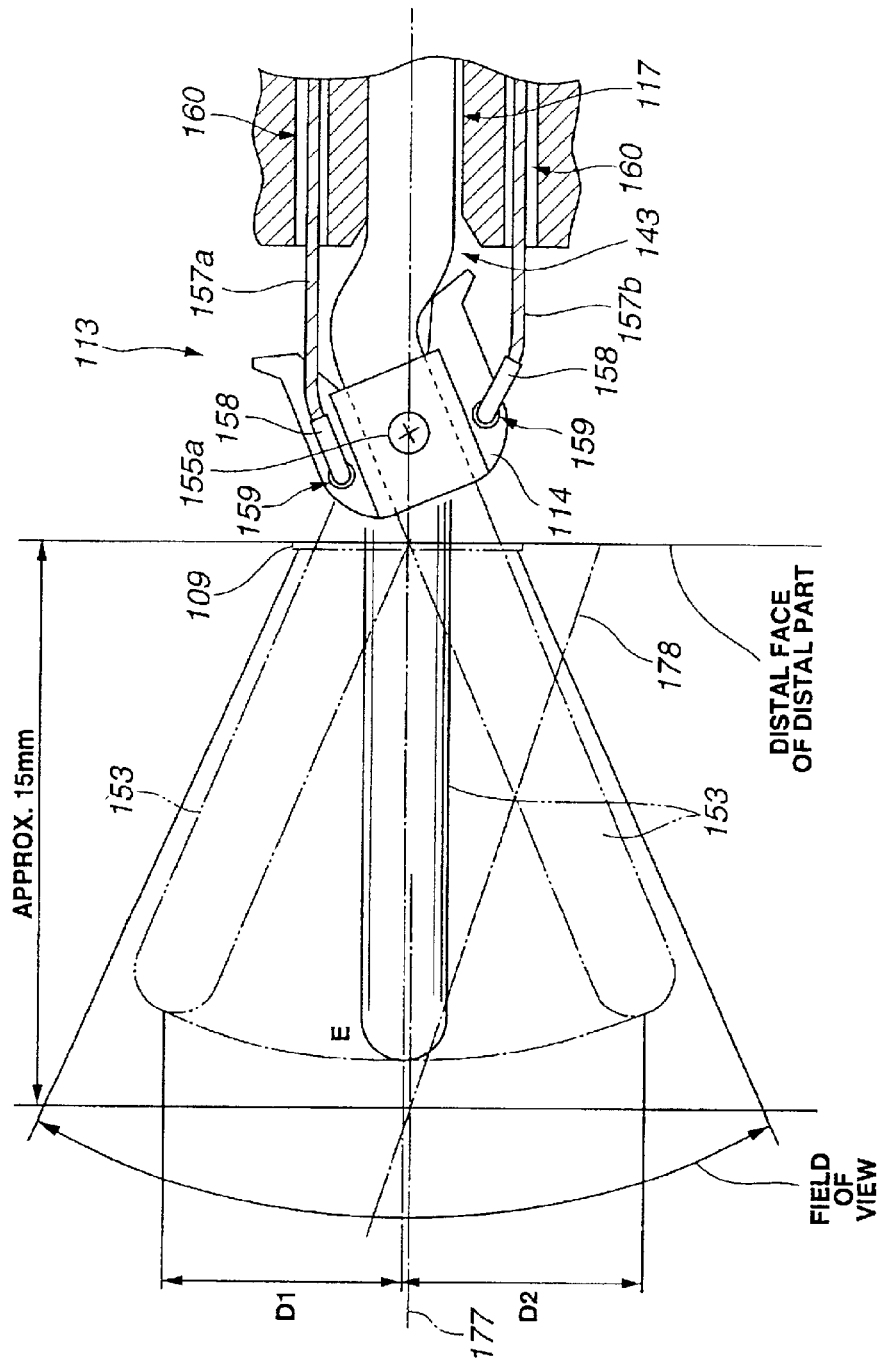

As shown in FIG. 43, the two angling wires 157a and 157b are passed through the angling wire passage channels 160 and coupled to the mechanism which permits an operator to manipulate the first treatment instrument swing stand 114 and which is incorporated in the swing stand manipulator 122. Consequently, when the angling wires 157a and 157b are alternately pulled by handling the first treatment instrument swing stand manipulation knob 133, the first treatment instrument swing stand 114 swings in the rightward and leftward directions, which corresponds to the turned directions in which the manipulation knob is turned, with the rotation shafts 155a and 155b as a center of rotation.

Consequently, the first treatment instrument 153 led out of the first treatment instrument swing stand 114 swings from the swing neutral position E, which is indicated with a solid line, within a range that is defined with a dot-dash line and alternate long and two short dashes lines and that falls within the field of view for observation spread ahead of the observation window 109.

At this time, the distal part of the first treatment instrument 153 swings from the swing neutral position, which is indicated with the solid line, in the rightward and leftward directions of the endoscope by a substantially equal magnitude (D1 equals approximately D2). Consequently, the tip of the first treatment instrument 153 traces an arc-like swing trajectory indicated with the dot-dash line.

Figure 44:
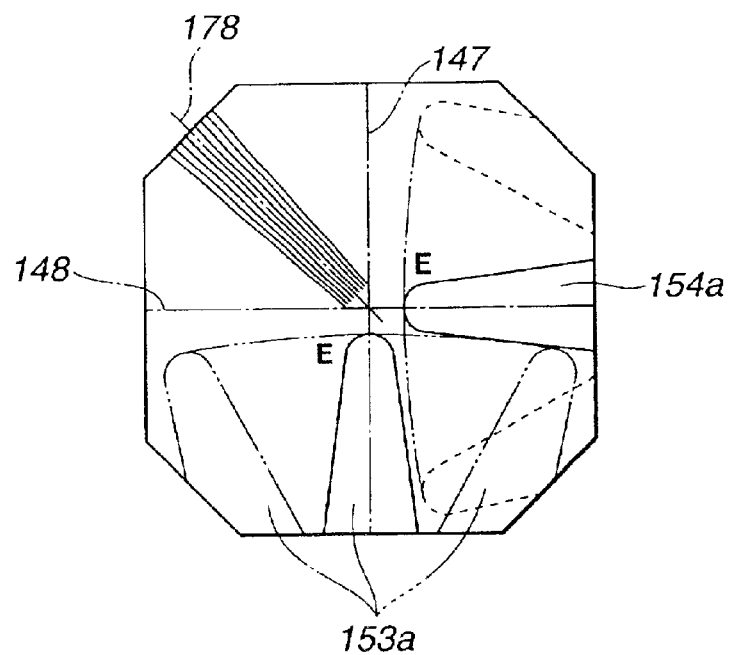

On the other hand, as shown in FIG. 44, an image 153a rendering the first treatment instrument 153 and being located in the center of a view image swings to the right side of the screen and the left side thereof. In FIG. 44, a center image 153a indicated with a solid line renders the first treatment instrument 153 located at the swing neutral position, and bears reference numeral E. As for the image 154a rendering the second treatment instrument 154, the center image 154a renders the second treatment instrument 154 located at the swing neutral position and bears reference numeral E.

When the first treatment instrument 153 is located at the swing neutral position E indicated with a solid line in FIG. 43, the first treatment instrument 153 is linear. The direction of projection in which the first treatment instrument 153 projects is substantially aligned with a centerline 177 that bisects the field of view. In this case, an advancing or withdrawing force that must be exerted in advancing or withdrawing the treatment instrument is the lightest. The treatment instrument can therefore be advanced or withdrawn easily.

Moreover, the direction of jet in which water is jetted out of the forward water outlet 112 is adjusted so that the jetted water will shoot a forward point which is located near the field-of-view centerline 177 at a distance of approximately 15 mm from the distal face. Consequently, when water or the like is jetted out of the water jet port 112, a line heading for the center of the view image (endoscopic image) is, as shown in FIG. 44, displayed to render a jetted water trajectory 178. In this state, cleansing is achieved most efficiently. Furthermore, the passage channels 160 through which the four angling wires 157a, 157b, 157c, and 157d run merge together within the swing stand manipulator 122, and communicate with the swing stand angling wire cleansing port 124. The four angling wires 157a, 157b, 157c, and 157d have one ends thereof fixed to the first treatment instrument swing stand 114 or second treatment instrument swing stand 115.

Operations to be exerted by the endoscope 101 having the foregoing features will be described below.

When the treatment instruments 153 and 154 are jutted out of the first treatment instrument swing stand 114 and second treatment instrument swing stand 115 respectively, the treatment instrument image 153a of the first treatment instrument 153 jutted out of the first treatment instrument swing stand 114 and the treatment instrument image 154a of the second treatment instrument 154 jutted out of the second treatment instrument swing stand 115 are, as shown in FIG. 44, displayed while being superposed on an endoscopic image. Herein, the treatment instrument image 153a projects from the lower edge of the endoscopic image and swings in the rightward and leftward directions of the screen. The treatment instrument image 154a projects from the right edge of the endoscopic image and swings in the upward and downward directions of the screen. Incidentally, the treatment instrument images 153a and 154a indicated with solid lines render the treatment instruments 153 and 154 located at the swing neutral positions described in conjunction with FIG. 43.

When the first treatment instrument swing stand 114 and second treatment instrument swing stand 115 are located at the swing neutral positions, the first treatment instrument 153 lies near the centerline 147 that bisects a view image in the rightward and leftward directions, and the second treatment instrument 154 lies near the centerline 148 that bisects the view image in the upward and downward directions.

Figure 45:
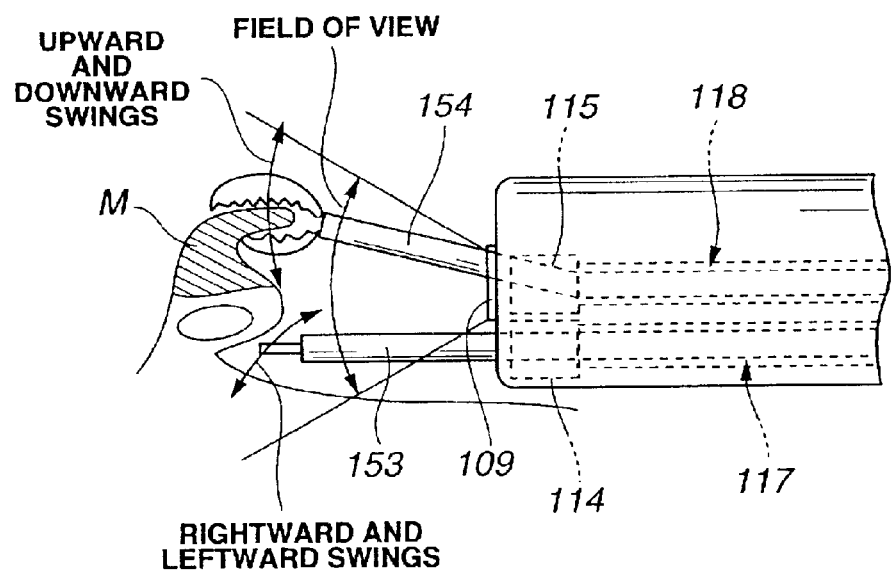
Figure 46:
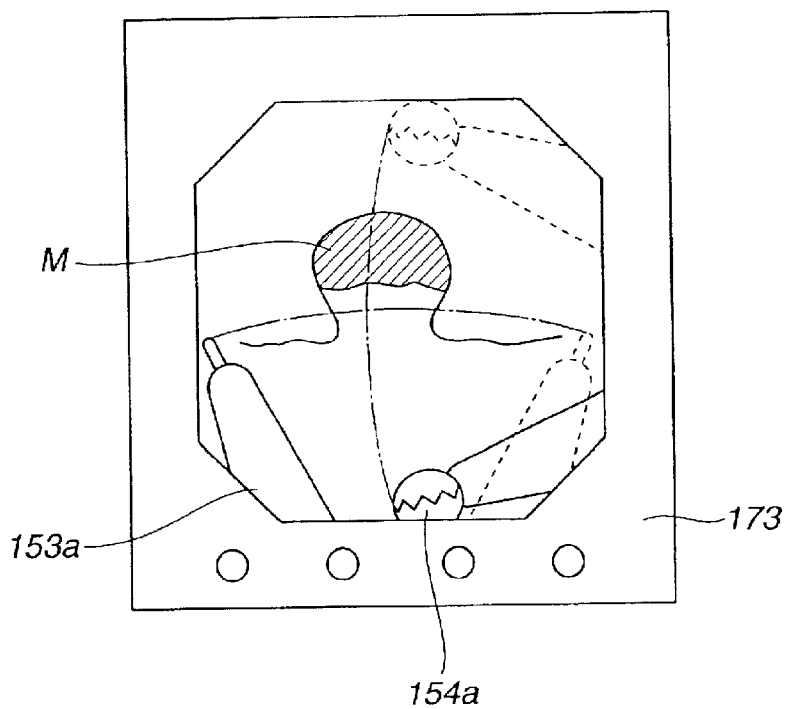

Herein, assume that a lesion is visualized to appear substantially in the center of an endoscopic image. In this case, the second treatment instrument 154 (for example, clamp forceps) are, as shown in FIG. 45, used to lift the mucosa M of the lesion, and the first treatment instrument 153 (for example, a cutting instrument) is swung rightwards and leftwards in order to incise the root of the lesion. At this time, an endoscopic image like the one shown in FIG. 46 is displayed on the screen of the monitor 173. Moreover, the images of the first treatment instrument 153 and second treatment instrument 154 can be swung over a wide range on the screen as indicated with solid lines and dashed lines.

As mentioned above, since the swing stand manipulator and insertion unit rotator are disposed near the first treatment instrument inlet and second treatment instrument inlet respectively, while the insertion unit is turned, the first treatment instrument and second treatment instrument can be swung, advanced, or withdrawn. This leads to greatly improved efficiency in treatment.

Moreover, two treatment instruments are jutted out of the treatment instrument swing stands that are in the swing neutral states, whereby the treatment instruments can be swung in both directions of raising and inversion in which they are raised and inverted. Treatment instrument images are displayed while being oriented to the center of an endoscopic image from the center position that bisects one edge of the endoscopic image in the rightward and leftward directions of the screen or from the center position that bisects another edge thereof in the upward and downward directions thereof. A lesion can be observed or treated using the endoscope with an image thereof displayed in the center of the screen. Thus, the treatment instruments can be approached to the lesion smoothly from optimal directions. Moreover, an operator can swing the treatment instruments without a feeling that something is wrong while viewing the endoscopic image, and thus proceed with work. This leads to greatly improved maneuverability and efficiency in work.

Furthermore, a lesion can be visualized to appear in the center of the screen for the purpose of endoscopic treatment. In this case, since the treatment instruments are jutted out linearly, an advancing or withdrawing force that must be exerted in advancing or withdrawing each of the treatment instruments is the lightest. The treatment instruments can therefore be easily advanced or withdrawn.

Consequently, the treatment instruments can be manipulated delicately and responsively. This results in an endoscope that will prove very useful in incision.

Moreover, the swing neutral positions of the treatment instruments are defined as the positions at which the images of the treatment instruments are displayed along the centerlines that bisect a view image in rightward and leftward directions of the screen and in the upward and downward directions thereof. Therefore, if the images of the treatment instruments are oriented to the center of the screen, it is judged from the endoscopic image that the treatment instruments are located at the swing neutral positions. Consequently, the first treatment instrument and second treatment instrument can be smoothly removed from the first treatment instrument swing stand and second treatment instrument swing stand respectively. At this time, since the treatment instruments are removed straight, they are little damaged.

FIG. 46 shows the endoscopic image in which the image of the first treatment instrument 153 (cutting instrument) appears below the image of the mucosa M of a lesion. In order to project the image of the first treatment instrument 153 above the image of the mucosa M of the lesion so as to proceed with incision, manipulations are performed as described below.

Figure 47:
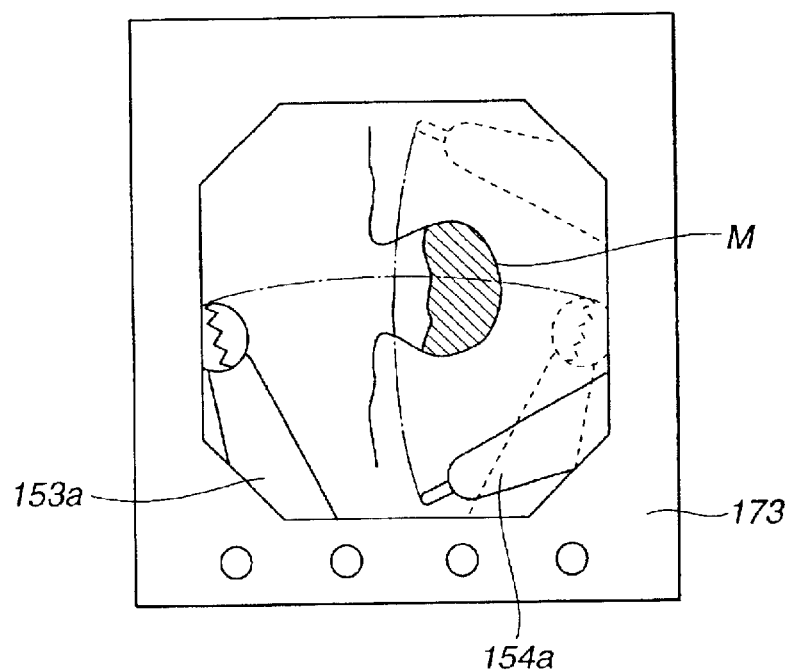

First, the insertion unit rotator 121 shown in FIG. 35 is handled in order to turn the insertion unit 102 leftwards by approximately 90°. At this time, as shown in FIG. 47, the image of a lesion is turned rightwards by 90°. In this state, the turn/lock switching lever 168 is handled to lock the turned insertion unit 102.

Thereafter, the clamp forceps and cutting instrument are switched. Specifically, the clamp forceps are adopted as the first treatment instrument 153, and the cutting instrument is adopted as the second treatment instrument 154. Consequently, the cutting instrument can be swung in order to incise the mucosa M of the lesion from above.

Figure 48:
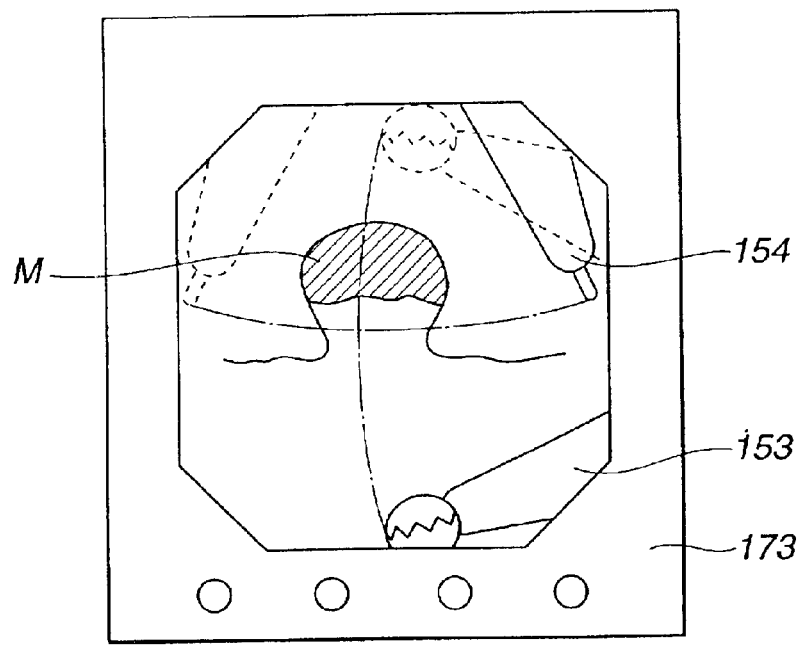

At this time, an endoscopic image displayed as shown in FIG. 47 is turned leftwards by 90° using an image rotation facility installed in the CCU (or a video processor) that is not shown and that is connected to the endoscope 101. Consequently, an endoscopic image shown in FIG. 48 is displayed on the screen of the monitor 173. Consequently, an operator can smoothly proceed with work in the same manner as the aforesaid one while viewing the endoscopic image.

Since the insertion unit rotator is included, the insertion unit alone can be twisted with the operation unit left intact in order to perform treatment. This obviates the necessity of twisting the operation unit together. The other manipulations to be performed by handling the operation unit will not be obstructed.

Moreover, the image rotation facility is used to change the orientation of an image so that an operator can view the image easily. The operator then performs treatment. Consequently, even when the first and second treatment instruments are switched, they can be swung accurately merely by viewing an endoscopic image.

Instead of including the first angling member 126 that is used to manipulate the first bending section and the second angling member 127 that is used to manipulate the second bending section, the first and second bending sections 106 and 107 may be designed to be controlled electrically.

Moreover, the directions of angling in which the endoscope is angled may be associated with the directions in which an image is turned by the rotation facility. Specifically, the upward, downward, rightward, and leftward directions of an endoscopic image displayed on the TV monitor are matched with the upward, downward, rightward, and leftward directions of angling. Consequently, even when the insertion unit is twisted, the insertion unit can be angled in relation to the upward, downward, rightward, and leftward directions of an endoscopic image. When an endoscope includes a mechanism for turning the insertion unit, an operator will not be at a loss to know in what direction the insertion unit should be angled.

Figure 49:
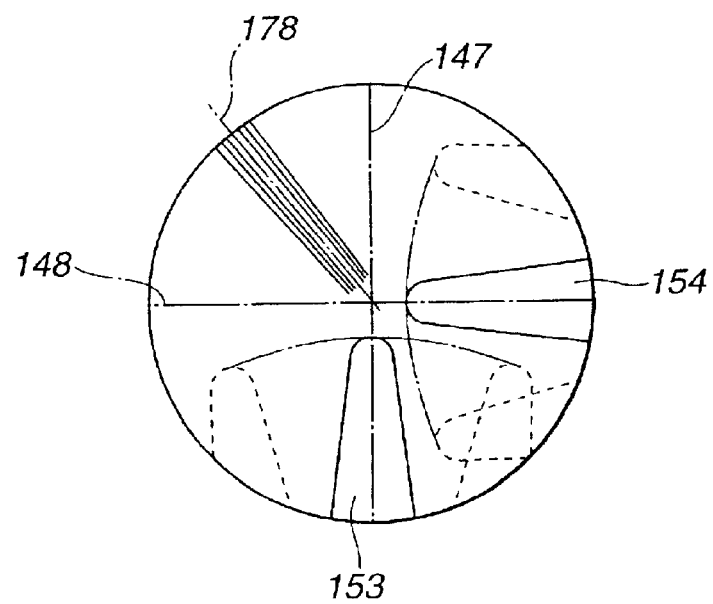

Furthermore, an endoscopic image displayed on the screen of the monitor may be, as shown in FIG. 49, circular. Namely, the shape of a field of view may have a circular shape or any other shape.

Furthermore, according to the present embodiment, the swing trajectory traced by a treatment instrument draws an arc. The swing trajectory is not limited to the arc-like one. For example, as shown in FIG. 50 and FIG. 51, the swing trajectory may be linear.

Figure 50:
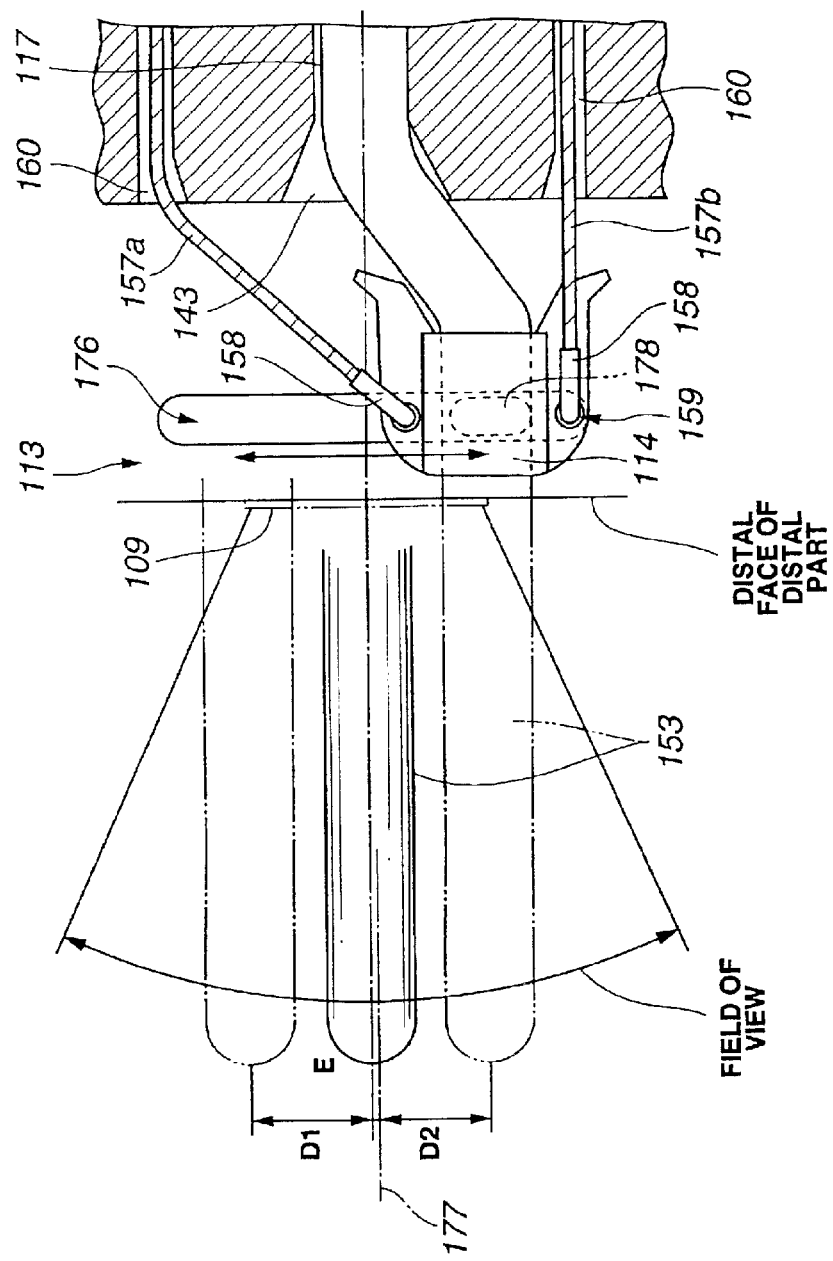
Figure 51:
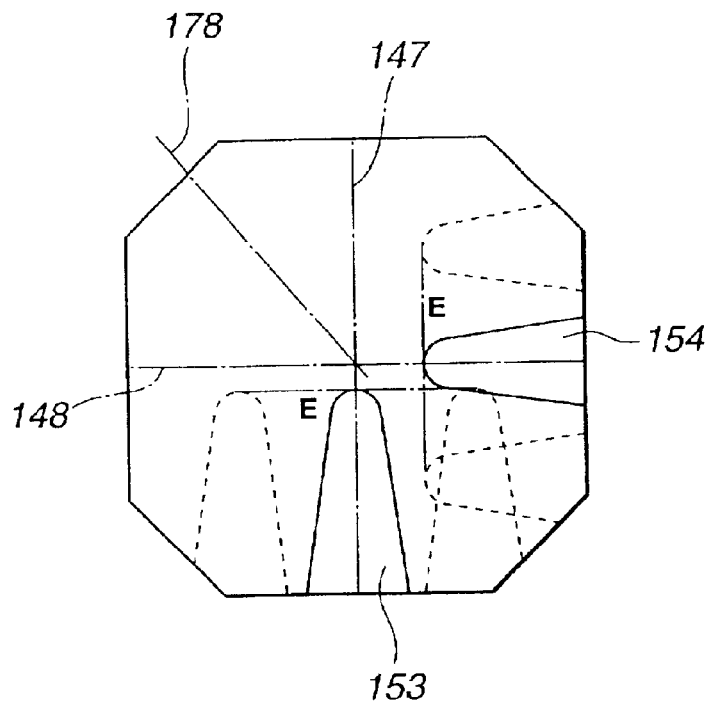

Consequently, as shown in FIG. 50, the first treatment instrument swing stand 114 has neither the first rotation shaft 155*a* nor second rotation shaft 155*b* that are shown in FIG. 42. Instead, a swing stand sliding convex part 179 that slides while being fitted in a swing stand sliding groove 176 which is formed linearly in parallel with the distal face within the swing stand storage member 113 is projected from the bottom of the first treatment instrument swing stand 114.

Consequently, by pulling either of the two angling wires 157*a* and 157*b*, the swing stand sliding convex part 179 projecting from the first treatment instrument swing stand 114 slides within the swing stand sliding groove 176 as indicated with arrows in FIG. 50.

Consequently, the tip of the first treatment instrument 153 jutted out of the first treatment instrument swing stand 114 traces a trajectory that draws a line substantially parallel to the distal face of the distal part 105. At this time, the first treatment instrument 153 swings by a nearly equal magnitude (D1 equals approximately D2) in the rightward and leftward directions of the endoscope with respect to the swing neutral position E indicated with a solid line. When the first treatment instrument 153 is located at the swing neutral position E, the first treatment instrument 153 projects in a direction that is substantially aligned with the field-of-view centerline 177.

Owing to the foregoing feature, the tips of the first and second treatment instruments 153 and 154 move substantially linearly substantially in parallel with the distal face of the distal part 105 but does not move to draw an arc unlike they are in the sixth embodiment. As shown in FIG. 51, when the first and second treatment instruments are located at the swing neutral positions E, the image of the first treatment instrument 153 is located near the centerline 147 that bisects an endoscopic image in the rightward and leftward directions of the screen, and the image of the second treatment instrument 154 is located near the centerline 148 that bisects the endoscopic image in the upward and downward directions thereof.

As mentioned above, the tips of the treatment instruments are moved substantially in parallel with the distal face of the distal part. Consequently, the treatment instruments can be caught fully not only in the center of a field of view but also in the perimeter thereof. This leads to greatly improved efficiency in incision.

The jetted water trajectory 178 to be traced by water jetted forwards passes a point that is located near the field-of-view centerline 177 at a distance of approximately 15 mm from the distal face.

Figure 52:
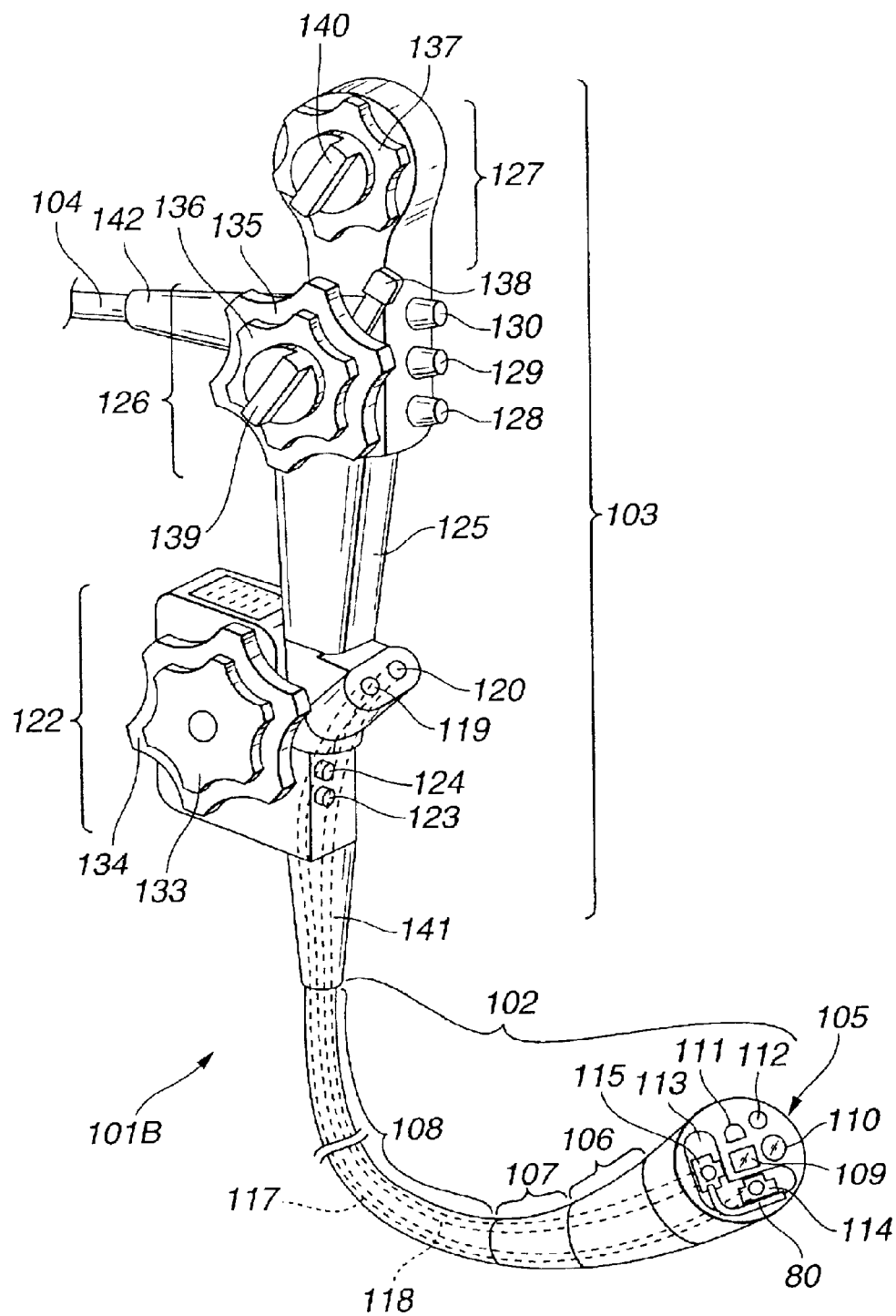

Referring to FIG. 52 to FIG. 59, a seventh embodiment of the present invention will be described below. An endoscope 101B of the seventh embodiment shown in FIG. 52 is analogous to the endoscope 101 of the sixth embodiment shown in FIG. 35.

The endoscope 101B of the seventh embodiment basically has the same features as the endoscope 101 of the sixth embodiment. The endoscope 101 includes a raising lever that is shaped like letter L and that is swung upwards and downwards responsively to the upward and downward swings of the second treatment instrument swing stand 115 incorporated in the distal part of the endoscope 101. One end of the raising lever is attached to the second treatment instrument swing stand 115, and the other end thereof is terminated near the first treatment instrument passage hole 145 of the first treatment instrument swing stand 114 that is swung in the rightward and leftward directions of the endoscope. Owing to the raising lever, a treatment instrument jutted out of the first treatment instrument passage hole 145 can be swung in the upward and downward directions. That is to say, the treatment instrument jutted out of the first treatment instrument passage hole 145 can be swung in four directions.

The features of the endoscope 101B and operations to be exerted by the endoscope will be described below.

The endoscope 101B shown in FIG. 52 consists mainly of the insertion unit 102 and operation unit 103. The universal cord 104 containing the light guide cable and signal cable is routed to the operation unit 103.

The insertion unit 102 has the distal part 105, first bending section 106, second bending section 107, and flexible tube 108 joined in that order from the distal end thereof.

The distal face of the distal part 105 contains the observation window 109, illumination window 110, air/water supply nozzle 111, and forward water outlet 112. Moreover, the treatment instrument swing stand storage member 113 that is shaped substantially like letter L is formed in the distal part. The first treatment instrument swing stand 114 and second treatment instrument swing stand 115 are held in the treatment instrument swing stand storage member 113 so that they can swing freely.

An objective and a solid-state imaging device for imaging a region to be observed, which are not shown, are mounted on the observation window 109. The signal cable contained in the universal cord 104 is routed to the solid-state imaging device. Alternatively, light carrying an image of the region to be observed which is formed by the objective may be propagated to an eyepiece optical system, which is not shown and incorporated in the operation unit 103, over an image guide cable that is not shown and passed through the insertion unit 102 and operation unit 103.

The universal cord 104 is routed to a video processor that is not shown. Thus, driving the solid-state imaging device is controlled, a produced image signal is subjected to predetermined signal processing and recorded on a recording medium, or an image is displayed on a monitor.

One end of the light guide cable over which illumination light is propagated, which is passed through the insertion unit 102, operation unit 103, and universal cord 104, and which is not shown is located to the illumination window 110. Illumination light emanating from a light source apparatus to which the universal cord 104 is routed is propagated over the light guide cable, and radiated to the region to be observed.

The air/water supply nozzle 111 communicates with an air/water supply channel that is not shown and that is run through the insertion unit 102 and operation unit 103. An air/water supply pump coupled to the air/water supply channel is used to spray air or water to the observation window 109.

The forward water outlet 112 communicates with a forward water supply channel that is not shown and that is run through the insertion unit 102 and operation unit 103. Water is supplied to the region to be observed through the forward water outlet 112.

The first treatment instrument swing stand 114 and second treatment instrument swing stand 115 are swung using the first treatment instrument swing stand manipulation knob 133 and second treatment instrument swing stand manipulation knob 134 that are included in the operation unit 103 and that will be described later. The first treatment instrument swing stand 114 swings substantially in the rightward and leftward directions of the field of view, while the second treatment instrument swing stand 115 swings substantially in the upward and downward directions thereof.

The first bending section 106 can be bent substantially in the upward and downward directions of the field of view and the rightward and leftward directions thereof using the first angling member 126 that is included in the operation unit 103 and that will be described later.

The second bending section 107 can be bent substantially in the upward and downward directions of the field of view using the second angling member 127 that is included in the operation unit 103 and that will be described later.

The first and second treatment instrument passage channels 117 and 118 lie through the insertion unit 102.

The distal opening of the first treatment instrument passage channel 117 communicates with the first treatment instrument swing stand 114, and the rear opening thereof communicates with the treatment instrument inlet 119 included in the operation unit 103.

Moreover, the distal opening of the second treatment instrument channel 118 communicates with the second treatment instrument swing stand 115, and the rear opening thereof communicates with the second treatment instrument inlet 120 included in the operation unit 103.

The operation unit 103 consists mainly of the swing stand manipulator 122, grip 125, first angling member 126, and second angling member 127.

First and second treatment instrument swing stand manipulating mechanisms that are not shown are incorporated in the swing stand manipulator 122. The first treatment instrument swing stand manipulation knob 133 that is part of the first treatment instrument swing stand manipulating mechanism is disposed on the external surface of the swing stand manipulator 122. The second treatment instrument swing stand manipulation knob 134 that is part of the second treatment instrument swing stand manipulating mechanism is also disposed on the external surface of the swing stand manipulator 122.

Specifically, when the first treatment instrument swing stand manipulation knob 133 is handled, the first treatment instrument swing stand 114 is remotely swung substantially in the rightward and leftward directions of the field of view by means of the first treatment instrument swing stand manipulating mechanism. When the second treatment instrument swing stand knob 134 is handled, the second treatment instrument swing stand 115 is remotely swung substantially in the upward and downward directions of the field of view by means of the second treatment instrument swing stand manipulating mechanism. The swings of the first and second treatment instrument swing stands 114 and 115 will be described later.

The forward water supply inlet 123 and swing stand angling wire cleansing port 124 are formed in the external surface of the swing stand manipulator 122. The forward water supply inlet 123 is linked to the forward water outlet 112 formed in the distal part 105 by a water supply channel that lies through the insertion unit 102.

Moreover, the swing stand angling wire cleansing port 124 is linked to the treatment instrument swing stand storage member 113 in the distal part 105 by the angling wire passage channels 160 that lie through the insertion unit 102 and the will be described later. Moreover, a syringe that is not shown can be fitted into the swing stand angling wire cleansing port 124 so that a cleansing solution or the like can be fed to the angling wire passage channels 160.

The first angling member 126 has externally a first bending section manipulation knob (upward and downward directions) 135, a first bending section manipulation knob (rightward and leftward directions) 136, a first turn/lock switching lever (upward and downward directions) 138, and a first turn/lock switching knob (rightward and leftward directions) 139.

The first bending section manipulation knob (in upward and downward directions) 135 is a manipulation knob that is used to bend the first bending section 106 in the upward or downward direction. The first bending section manipulation knob 135 is coupled to upward/downward angling wires (not shown), which are routed to the first bending section 106, within the first angling member 126 or grip 125.

The first bending section manipulation knob (rightward and leftward directions) 136 is a manipulation knob that is used to bend the first bending section 106 in the rightward or leftward direction. The first bending section manipulation knob 136 is coupled to rightward/leftward angling wires (not shown), which are routed to the first bending section 106, within the first angling member 126 or grip 125.

A state in which the first bending section 106 can be bent using the first bending section manipulation knob (upward and downward directions) 135 and a state in which the bent first bending section 106 is locked are switched using the first turn/lock switching lever (upward and downward directions) 138. A state in which the first bending section 106 can be bent using the first bending section manipulation knob (rightward and leftward directions) 136 and a state in which the bent first bending section 106 is locked are switched using the first turn/lock switching knob (rightward and leftward directions) 139.

The second angling member 127 has externally a second bending section manipulation knob 137 and a second turn/lock switching knob 140.

The second bending section manipulation knob 137 is a knob used to bend the second bending section 107 in the upward or downward direction, and coupled to upward/downward angling wires (not shown), which are routed to the second bending section 107, within the second angling member 127 or grip 125.

A state in which the second bending section 107 can be bent using the second bending section manipulation knob 137 and a state in which the bent second bending section 107 is locked are switched using the second turn/lock switching knob 140.

The air/water supply control button 128, suction control button 129, and image control button 130 are disposed near the first angling member 126.

The air/water supply control button 128 is a button used to control driving of an air/water supply pump connected to the air/water supply nozzle 111 included in the distal part 105 of the insertion unit 102. The suction control button 129 is a button used to control driving of a pump that sucks a gas or liquid, which is supplied through the air/water supply nozzle 111, by way of the suction channel that lies through the operation unit 103 and insertion unit 102 and that is not shown. The image control button 130 is a button used to control an image, which is displayed on the monitor, via a video processor to which the universal cord 104 is routed. The details have nothing to do with the present embodiment and will therefore be omitted.

Incidentally, an insertion member anti-breakage member 141 is mounted on the joint joining the operation unit 103 and the insertion unit 102. A universal cord anti-breakage member 142 is mounted as the joint joining the operation unit 103 and the universal cord 104. Thus, the breakage of the insertion unit 102 at the root thereof and the breakage of the universal cord 104 at the root thereof are prevented.

Figure 53:
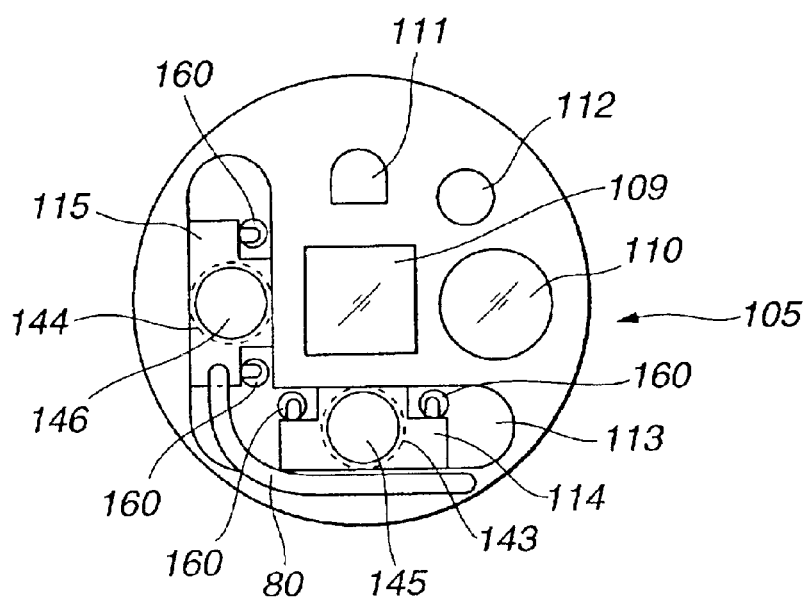

Next, the distal structure of the distal part 105 will be described with reference to FIG. 53. The observation window 109 is disposed in the center of the distal face of the distal part 105. Referring to FIG. 53, the illumination window 110 is located on the right side of the observation window 109, and the air/water supply nozzle 111 is located above the observation window 109. The forward water outlet 112 is interposed between the illumination window 110 and air/water supply nozzle 111.

The treatment instrument swing stand storage member 113 shaped substantially like letter L lies on the left side of and below the observation window 109.

The first treatment instrument swing stand 114 is disposed in the portion of the treatment instrument swing stand storage member 113 below the observation window 109. The second treatment instrument swing stand 115 is disposed in the portion of the treatment instrument swing stand storage member 113 on the left side of the observation window 109.

The first treatment instrument swing stand 114 and second treatment instrument swing stand 115 have a first treatment instrument passage hole 145 and a second treatment instrument passage hole 146 respectively.

The first treatment instrument passage hole 145 and second treatment instrument passage hole 146 communicate with an opening 143 (indicated with a dashed line) of the first treatment instrument channel 117 and an opening 144 (indicated with a dashed line) of the second treatment instrument passage channel 118 respectively.

A raising bar 80 shaped substantially like letter L is attached to the second treatment instrument swing stand 115. The proximal end of the raising bar 80 is fixed to the second treatment instrument swing stand 115, while the distal end thereof extends below the first treatment instrument passage hole 145.

Moreover, the angling wire passage channels 160 open onto both sides of the first treatment instrument swing stand 114 and both sides of the second treatment instrument swing stand 115.

Specifically, as shown in FIG. 54, the first treatment instrument 153 passed through the first treatment instrument passage channel 117 is inserted into the first treatment instrument passage hole 145 of the first treatment instrument swing stand 114 through the opening 143 of the first treatment instrument passage channel 117. The first treatment instrument 153 is then led or jutted out of the distal part 105.

On the other hand, the first rotation shaft 155*a* is embedded in the center of the first treatment instrument swing stand 114. The terminal ends of the angling wires 157 passed through the angling wire passage channels 160 are fixed to the wire termination members 158 and locked in both the sides of the first treatment instrument swing stand 114.

The proximal ends of the angling wires 157 are fixed to the first treatment instrument swing stand manipulation knob 133 via the first treatment instrument swing stand manipulating mechanism included in the swing stand manipulator 122.

In other words, by turning the first swing stand manipulation knob 133, the angling wires 157 are alternately pulled. This causes the first treatment instrument swing stand 114 to swing on the first rotation shaft 155*a* in the rightward and leftward directions. With the swing of the first treatment instrument swing stand 114, the first treatment instrument 153 passed through the first treatment instrument passage hole 145 swings in the rightward and leftward directions.

Incidentally, the movement of the second treatment instrument swing stand 115 is the same as that of the first treatment instrument swing stand 114. The description of the movement of the second treatment instrument swing stand 115 will be omitted. Reference numerals relevant to the second swing stand 115 are written in parentheses in FIG. 54.

The first treatment instrument 153 jutted out through the first treatment instrument passage hole 145 of the first treatment instrument swing stand 114 swings, as shown in FIG. 54, as indicated with an alternate long and two short dashes line within the field of view for observation spread ahead of the observation window 109. As shown in FIG. 53, the observation window 109 is located above the first treatment instrument swing stand 114. Therefore, the observation window 109 is indicated with an alternate long and two short dashes line in FIG. 54.

Specifically, when the first treatment instrument swing stand manipulation knob 133 included in the treatment instrument swing stand manipulator 122 is turned, the angling wires 157 coupled to the first treatment instrument swing stand 114 are alternately pulled via the first treatment instrument swing stand manipulating mechanism. This causes the first treatment instrument swing stand 114 to swing substantially in the rightward and leftward directions with the first rotation shaft 155*a* as a center of rotation. Consequently, the first treatment instrument 153 swings.

A swing trajectory traced by the tip of the first treatment instrument 153 draws an arc. In other words, along with the swing of the first treatment instrument swing stand 114, the first treatment instrument 153 swings by a nearly equal magnitude (D1 equals approximately D2) in the rightward and leftward directions with respect to the field-of-view centerline 177 from the swing neutral state (position) E in which the first treatment instrument 153 is jutted out in the axial direction of the distal part 105.

On the other hand, the jetted water trajectory 178 traced by water supplied forwards through the forward water outlet 112 is adjusted so that it will pass a point which is located near the field-of-view centerline 177 at a distance of approximately 15 mm from the distal face of the distal part 105.

The four angling wires that pull the first and second treatment instrument swing stands 114 and 115 lie through the four angling wire passage channels 160. The angling wire passage channels 160 are merged into one within the swing stand manipulator 122. The proximal end of the resultant channel opens onto the swing stand angling wire cleansing port 124. Consequently, when a cleansing solution is poured through the wing stand angling wire cleansing port 124, the angling wire passage channels 160 and angling wires 157 can be cleansed.

Next, the structure of the first treatment instrument swing stand 114 and the swing thereof will be described with reference to FIG. 55, and the structure of the second treatment instrument swing stand 115 and the swing thereof will be described with reference to FIG. 56.

Figure 55:
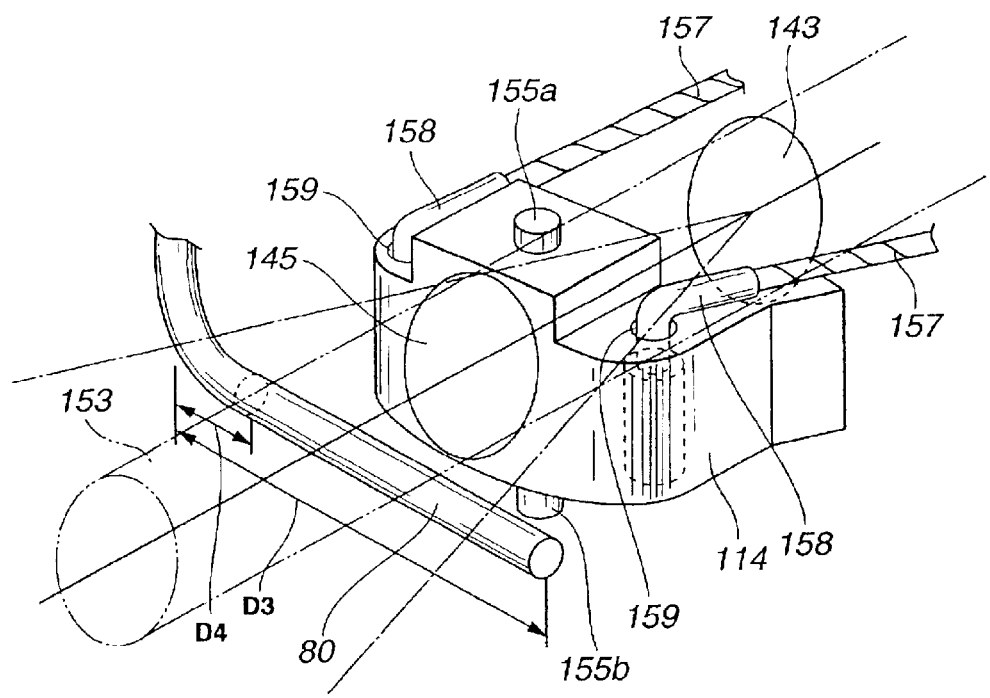

As shown in FIG. 55, the first and second rotation shafts 155a and 155b are embedded substantially in the centers of the top and bottom of the first treatment instrument swing stand 114. The first and second rotation shafts 155a and 155b are aligned with the centerline of the first treatment instrument passage hole 145.

The two attachment holes 159 are bored in both of the right and left edges of the first treatment instrument swing stand 114 with respect to the first and second rotation shafts 155a and 155b. The wire termination members 158 for terminating the angling wires 157 are fitted into the attachment holes 159.

The first and second rotation shafts 155a and 155b are held in the treatment instrument swing stand storage member 113 so that they can rotate freely. When the two angling wires 157 are pulled alternately, the first treatment instrument swing stand 114 is remotely swung in the rightward and leftward directions within the treatment instrument swing stand storage member 113 with the first and second rotation shafts 155a and 155b as a center of rotation. The wire termination members 158 are held in the attachment holes 159 so that they can rotate freely.

Referring to FIG. 55, the first treatment instrument 153 passed through the first treatment instrument hole 145 of the first treatment instrument swing stand 114 is jutted out of the first treatment instrument passage hole 145 while being in the swing neutral state or being substantially straight. The raising bar 80 is disposed below the first treatment instrument 153 in FIG. 55. Specifically, when the angling wires 157 are pulled, the first treatment instrument swing stand 114 swings in the rightward and leftward directions of FIG. 55. This causes the first treatment instrument 153 to swing in the rightward and leftward directions above the raising bar 80.

Figure 56:
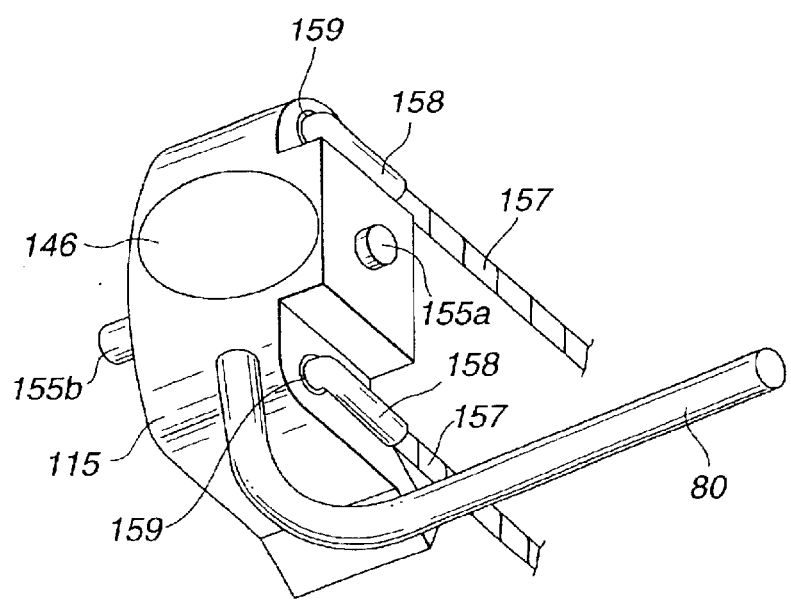

On the other hand, the second treatment instrument swing stand 115 has, as shown in FIG. 56, similarly to the first treatment instrument swing stand 114, the first and second rotation shafts 155a and 155b. Moreover, the second treatment instrument swing stand 115 has two attachment holes 159 into which the wire termination members 158 for terminating the angling wires 157 are fitted. The second treatment instrument swing stand 115 is fixed in a direction substantially orthogonal to the direction in which the first treatment instrument swing stand 114 is fixed. Furthermore, the second treatment instrument swing stand 115 has the raising bar 80 that can be brought into contact with the first treatment instrument 153 passed through the first treatment instrument swing stand 114.

When the angling wires 157 terminated at the second treatment instrument swing stand 115 are pulled, the second treatment instrument swing stand 115 swings on the first and second rotation shafts 155a and 155b in the upward and downward directions of the drawing.

When the second treatment instrument swing stand 115 swings in the upward and downward directions, the raising bar 80 turns in the upward and downward directions. Consequently, as shown in FIG. 55, the first treatment instrument 153 jutted out of the first treatment instrument swing stand 114 is swung in the upward and downward directions of the drawing.

If the length of the raising bar 80 is set to be as large as length D3 shown in FIG. 55, the first treatment instrument 153 can be swung in the upward and downward directions by the second treatment instrument swing stand 115 over the entire swingable range within which the first treatment instrument swing stand 114 can swing in the rightward and leftward directions. If the length of the raising bar 80 is set to be as small as length D4, only when the first treatment instrument swing stand 114 is swung in an extremely rightward direction of observation, the first treatment instrument 153 can be swung in the upward and downward directions by means of the second treatment instrument swing stand 115.

In other words, the first treatment instrument 153 passed through the first treatment instrument swing stand 114 swings with the swing of the first treatment instrument swing stand 114. Moreover, the first treatment instrument 153 can swing in the upward and downward directions, which are substantially orthogonal to the directions of swing in which the first treatment instrument swing stand 114 can swing, owing to the raising bar 80 extended from the second treatment instrument swing stand 115.

Incidentally, it is apparent that the raising bar 80 may be attached to the first treatment instrument swing stand 114. In this case, the second treatment instrument 154 passed through the second treatment instrument swing stand 115 can be swung in the rightward and leftward directions that are substantially orthogonal to the directions of swing in which the second treatment instrument swing stand 115 can swing.

Figure 57:
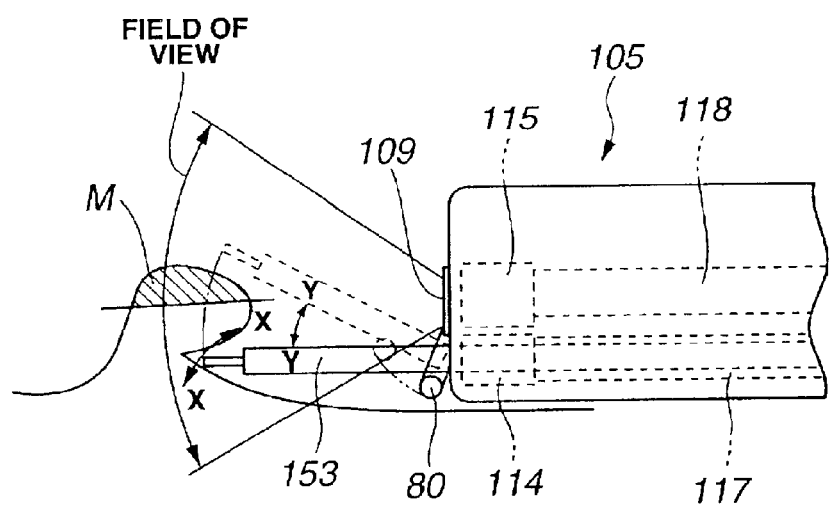

Referring to FIG. 57, treating a lesion using the endoscope 101B will be described below.

FIG. 57 shows the swing of the first treatment instrument 153 jutted out of the first treatment instrument swing stand 114. When the first treatment instrument swing stand 114 is swung, the first treatment instrument 153 swings in the rightward and leftward directions as indicated with arrows X in the drawing. Thereafter, when the second treatment instrument swing stand 115 is swung, the first treatment instrument 153 swings in the upward and downward directions as indicated with arrows Y in the drawing owing to the raising bar 80. Consequently, the first treatment instrument 153 can be moved to a position indicated with a dashed line in the drawing.

Specifically, for example, the tips of cutting forceps serving as the first treatment instrument 153 are led to the substratum of the mucosa M of a lesion in a body cavity. The first and second treatment instrument swing stands 114 and 115 are swung in order to swing the first treatment instrument 153 in the upward, downward, rightward, and leftward directions. Consequently, the mucosa M of the lesion can be incised laterally and vertically.

Figure 58:
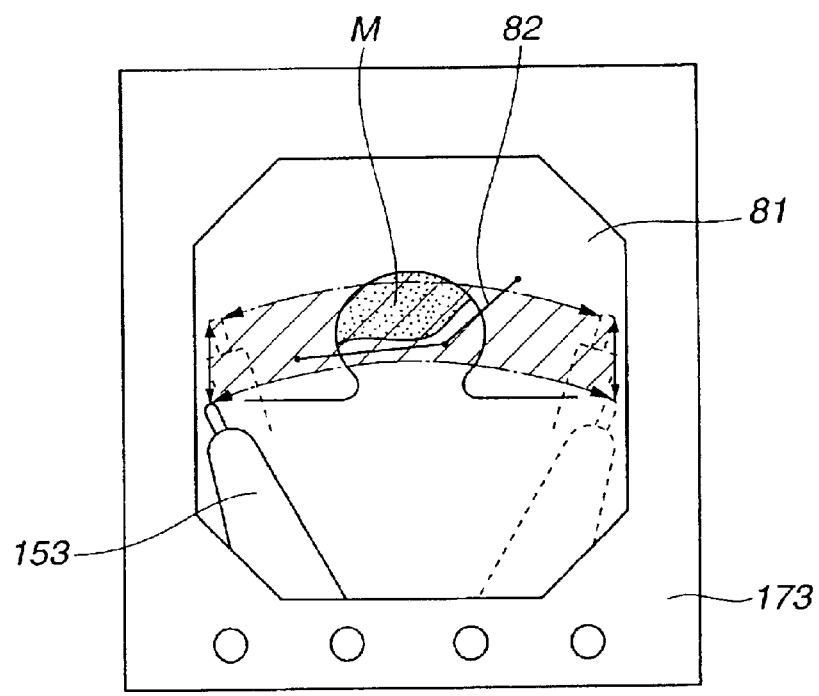

Moreover, the movement of the first treatment instrument 153 for treatment is, as shown in FIG. 58, observed by displaying on the monitor 173 an image of a region to be observed which is picked up by the solid-state imaging device mounted on the observation window 109 in the distal part 105 of the insertion unit 102. Specifically, an image of a region to be observed that is caught in the field of view spread ahead of the observation window 109 and an image of the distal part of the first treatment instrument 153 that swings over the swingable range are displayed on the monitor.

Specifically, by manipulating the first and second treatment instrument swing stands 114 and 115, the tip of the first treatment instrument 153 jutted out of the first treatment instrument swing stand 114 can be moved freely within a portion of the region to be observed corresponding to a hatched portion of FIG. 58. The mucosa M of the lesion within the portion can be incised.

A transparent touch-sensitive panel 81 and a tip movement desirable line 82 shown in FIG. 58 will be described later.

Next, how to manipulate the first and second treatment instruments accessory to the endoscope 101B will be described with reference to FIG. 59.

Figure 59:
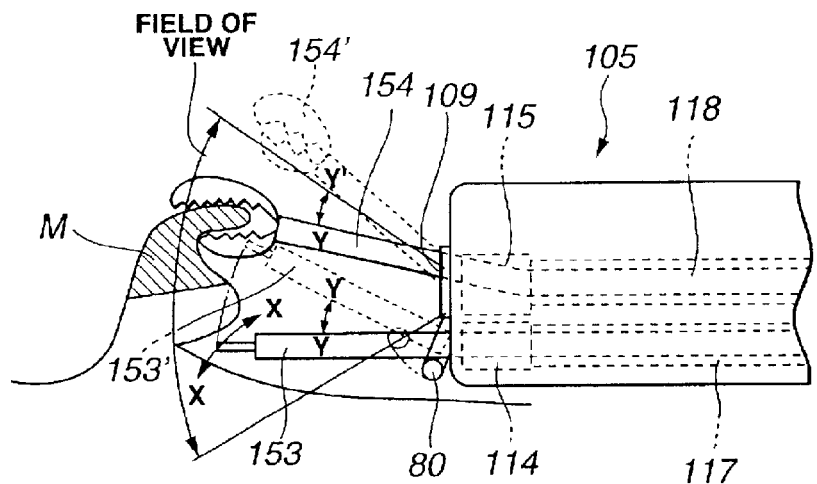

Referring to FIG. 59, the first treatment instrument 153 passed through the first treatment instrument swing stand 114 shall be, similarly to the one described in conjunction with FIG. 57, cutting forceps. The second treatment instrument 154 passed through the second treatment instrument swing stand 115 shall be, for example, clamp forceps.

The clamp forceps serving as the second treatment instrument 154 are used to clamp the mucosa M of a lesion, and the second treatment instrument swing stand 115 is manipulated. This causes the first treatment instrument 153 to swing in the directions of arrows Y in the drawing owing to the raising bar 80. The second treatment instrument 154 swings in the directions of arrows Y' in the drawing. The first and second treatment instruments 153 and 154 are swung to the positions of first and second treatment instruments 153' and 154' indicated with dot lines in the drawing.

Specifically, the mucosa M of the lesion clamped by the clamp forceps serving as the second treatment instrument 154 is lifted upwards in the drawing. The cutting forceps serving as the first treatment instrument 153 are thrust into the substratum of the lifted mucosa M of the lesion.

In this state, when the first treatment instrument swing stand 114 is swung in the directions of arrows X in the drawing, the mucosa M of the lesion is incised. Consequently, the mucosa M of the lesion is incised reliably and easily.

If the length of the raising bar 80 is set to the small length D4 as shown in FIG. 55 that has been referred to previously, only when the first treatment instrument 153 is swung extremely rightwards, the first treatment instrument 153 can be swung in the upward and downward directions with the raising bar 80 (second treatment instrument swing stand 115). In short, the swingable range of the first treatment instrument 153 depends on the length D of the raising bar 80.

Next, an endoscope 101C in accordance with an eighth embodiment of the present invention will be described with reference to FIG. 60 to FIG. 64.

The endoscope of the present embodiment is characterized in that an electric switch unit 87 is used to bend the first and second bending sections 106 and 107, swing the first and second treatment instrument swing stands 114 and 115, and supply water forwards through the forward water outlet 112.

Figure 60:
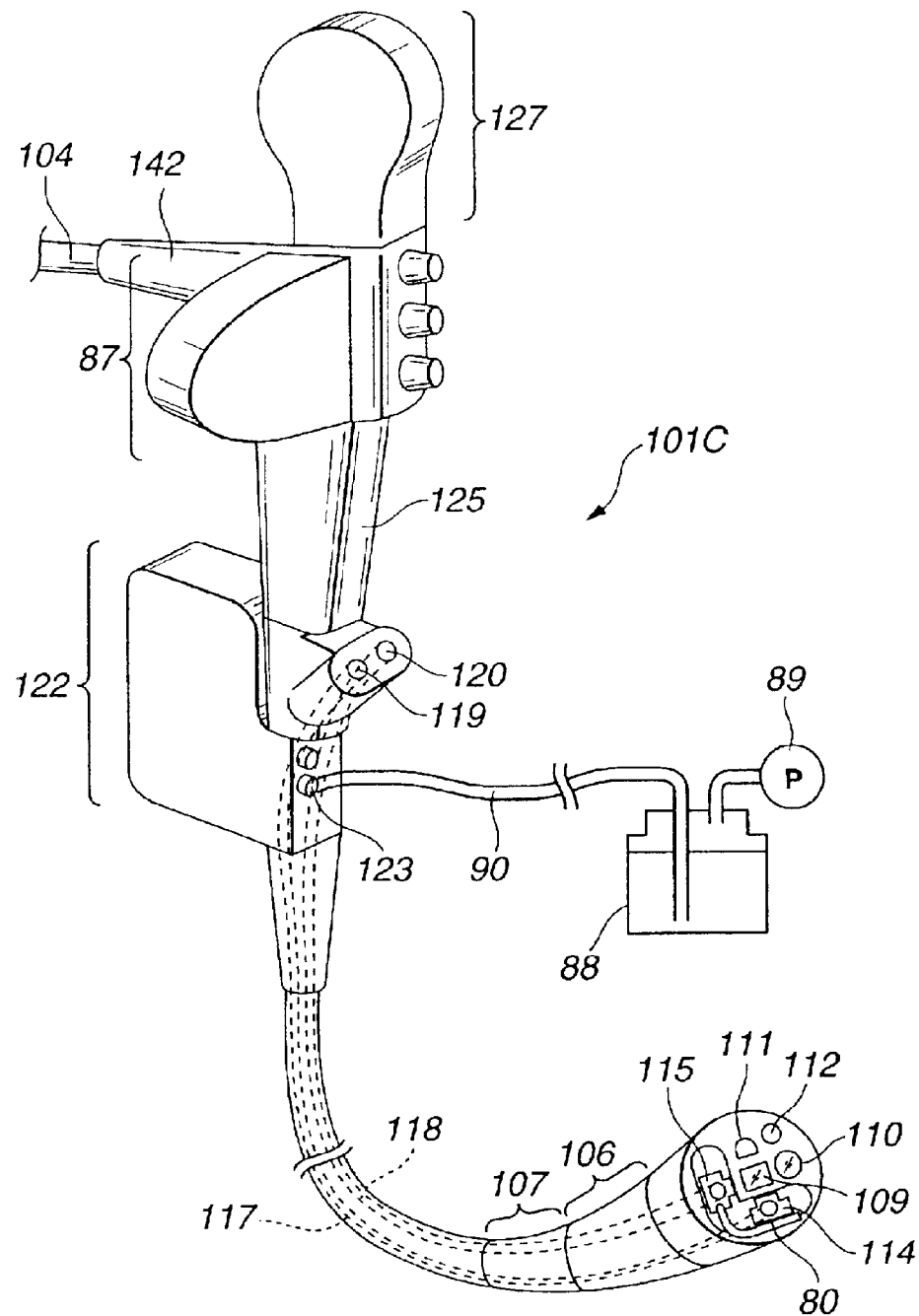

To be more specific, as shown in FIG. 60, the endoscope 101C does not have, unlike the endoscope 101B, the manipulation knobs 133, 134, and 137 and the turn/lock switching knob 140 on the swing stand manipulator 122 and the second angling member 127. Moreover, the endoscope 101C has the electric switch unit 87 on behalf of the first angling member 126.

Figure 61:
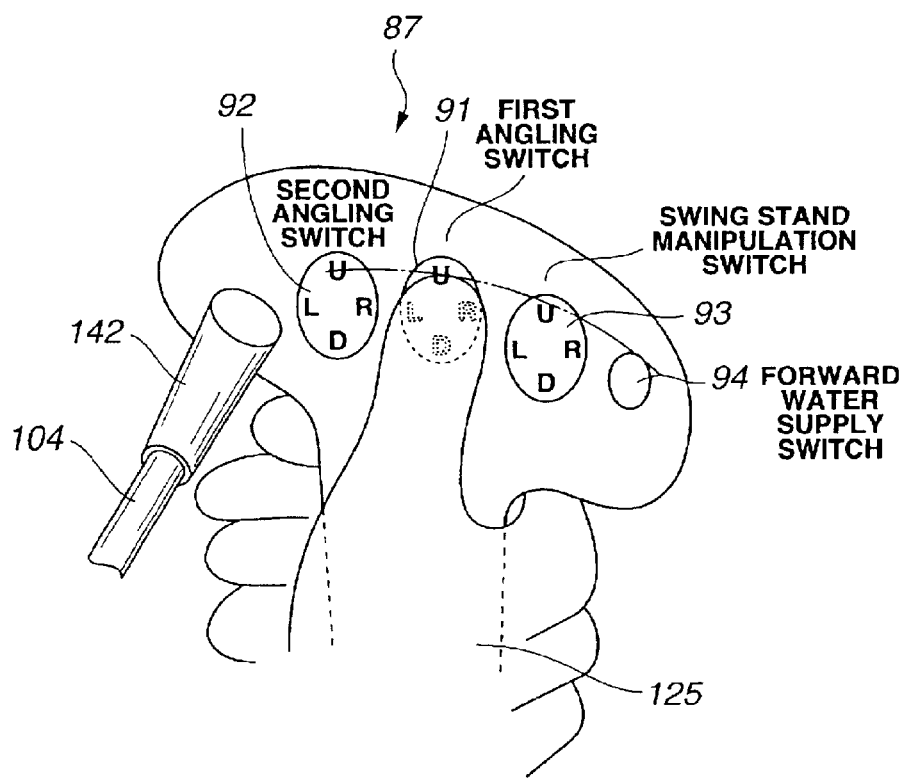
FIG. 60 to FIG. 63 are concerned with an eighth embodiment of the present invention.

The electric switch unit 87 includes, as shown in FIG. 61, a first angling switch 91, a second angling switch 92, a swing stand manipulation switch 93, and a forward water supply switch 94.

The first and second angling switches 91 and 92 included in the electric switch unit 87 each include switches that instruct bending of the first or second bending section 106 or 107 in the upward, downward, rightward, or leftward (U, D, R, or L) direction. For example, when the Upward (U) switch of the first angling switch 91 is turned on, a motor that is not shown is driven in order to pull the angling wires, which are not shown, so as to bend the first bending section 106 upwards. When any of the Upward, Downward, Rightward, and Leftward (U, D, R, L) switches included in the first and second angling switches 91 and 92 is turned on, the first or second bending section 106 or 107 is bent in the direction associated with the switch turned on.

Incidentally, the first and second bending sections 106 and 107 can be bent in the four directions of the upward, downward, rightward, and leftward directions. If either of the first and second bending sections is made bendable in two directions alone, the switch associated with the bending section bendable in the two directions alone is, needless to say, composed of two switches that instruct bending in the two directions.

Moreover, the swing stand manipulation switch 93 is, similarly to the first and second angling switches 91 and 92, composed of Upward, Downward, Rightward, and Leftward (U, D, R, and L) switches and a motor that is driven when any of the switches is turned on and that pulls the angling wires 157 terminated at the treatment instrument swing stand 114 or 115.

The forward water supply switch 94 is a switch to be turned on or off in order to enable or disable water supply from a forward water supply tank 88 that is connected to the forward water supply inlet 123 included in the swing stand manipulator 122. Sterilization water is reserved in the forward water supply tank 88. A water supply tube 90 led out of the forward water supply tank 88 is routed to the forward water supply inlet 123. When the water supply tank 88 is pressured by a booster pump 89, the sterilization water reserved in the forward water supply tank 88 is delivered to the forward water supply inlet 123 over the water supply tube 90. The water supplied to the forward water supply inlet 123 is jetted out through the forward water outlet 112 included in the distal part 105 by way of a channel lying through the insertion unit 2. The forward water supply switch 94 is turned on or off in order to switch driving and non-driving of the booster pump 89.

If the first angling switch 91, second angling switch 92, swing stand manipulation switch 93, and forward water supply switch 94 included in the electric switch unit 87 are arranged in an arc so that they can be turned on or off with an operator's thumb, maneuverability and efficiency improve.

Figure 64:
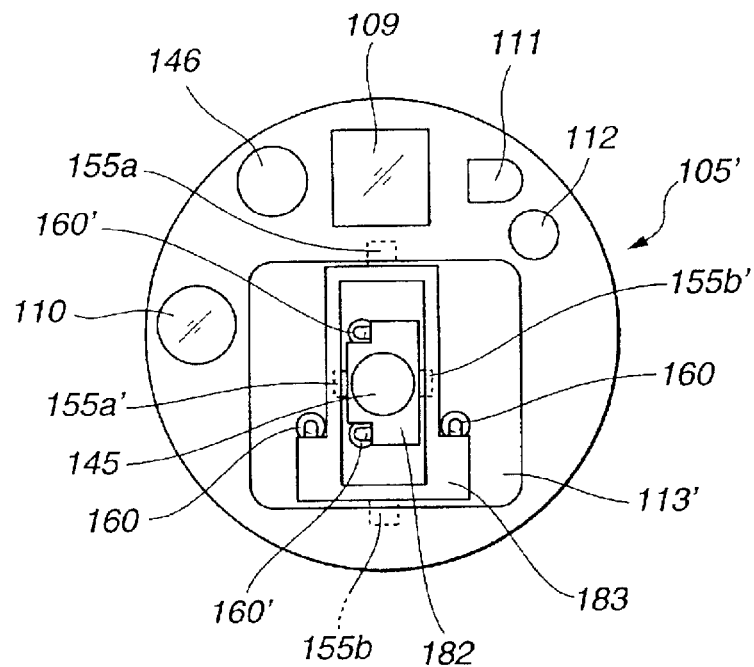
FIG. 64 is a front view showing the arrangement of components in the distal face of the distal part of an endoscope in accordance with a ninth embodiment of the present invention.

How to treat the mucosa M of a lesion using the electric control type endoscope that uses an electric motor to bend the first and second bending sections 106 and 107 thereof and to swing the treatment instrument swing stands 114 and 115 thereof will be described with reference to FIG. 62 and FIG. 64.

Figure 62:
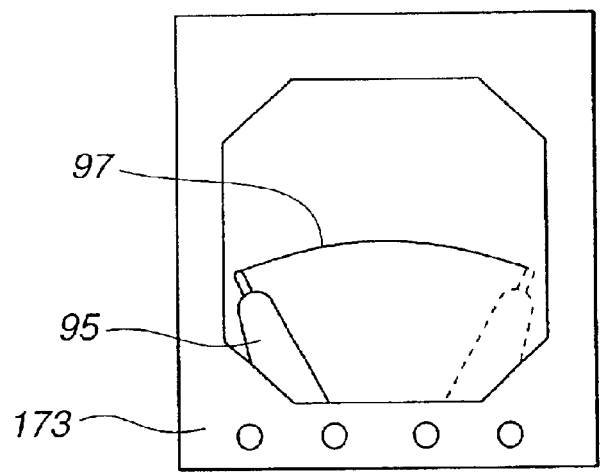
Figure 63:
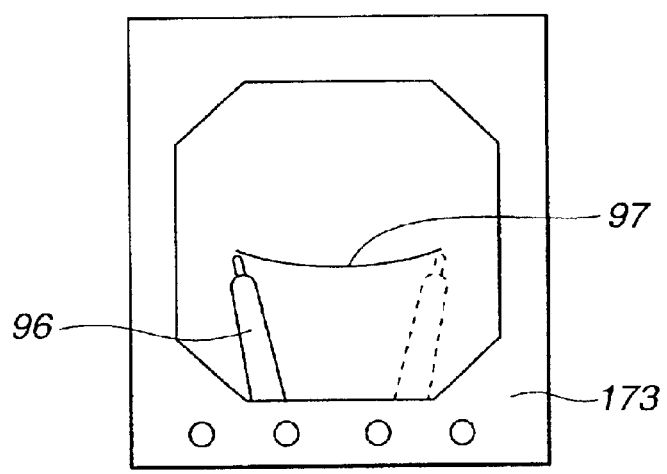

FIG. 62 and FIG. 63 are explanatory diagrams showing a swing trajectory traced by a treatment instrument accessory to the electric control type endoscope 101C that includes an electric motor and that is shown in FIG. 60.

FIG. 62 shows a swing trajectory traced by a large-diameter treatment instrument 95. FIG. 63 shows a swing trajectory traced by a small-diameter treatment instrument 96. The swing trajectories of the treatment instruments shown in FIG. 62 and FIG. 63 are tip movement predictive lines 97 each of which expresses the swing of the tip of the treatment instrument and is displayed on the monitor 173, on which an image of a region to be observed (region near the mucosa M of a lesion) is displayed, together with the image of the region to be observed.

As seen from FIG. 62 and FIG. 63, the swing trajectory of the tip of a treatment instrument varies depending on the thickness or hardness of the treatment instrument. Therefore, the tips of the treatment instruments 95 and 96 trace different swing trajectories. Furthermore, the swing trajectory varies depending on the relationship between the inner diameter of the first treatment instrument passage hole 145 (second treatment instrument passage hole 146) and the outer diameter of a treatment instrument to be passed through the hole, that is, the size of a clearance.

Treatment instrument sensing means that are not shown are included for identifying the types of treatment instruments inserted into the first treatment instrument inlet 119 and second treatment instrument inlet 120. The treatment instrument sensing means sense the types of treatment instruments passed through the first treatment instrument passage channel 117 and second treatment instrument passage channel 118. Based on the sensed types of treatment instruments, stored data items representing the specifications, performance, and swing trajectories characteristic of the types of treatment instruments are read. Consequently, the types of treatment instruments and the tip movement predictive lines 97 are displayed on the monitor 173.

The tip movement predictive line 97 is a predictive line along which the tip of a treatment instrument swings when the first treatment instrument swing stand 114 (or second treatment instrument swing stand 115) swings with the treatment instrument jutted out by a certain magnitude, for example, approximately 15 mm from the distal face.

When the tip movement predictive line 97 is displayed in advance on the monitor 173, an operator can grasp in advance the movement of the tip of a treatment instrument employed. This leads to efficient treatment.

Moreover, as described in conjunction with FIG. 58, the screen of the monitor 173 is realized with the transparent touch-sensitive panel 81. With an image of the mucosa M of a lesion displayed on the transparent touch-sensitive panel 81, an operator draws a tip movement desirable line 82, along which a treatment instrument to be used to incise a lesion desirably swings, on the transparent panel 81 with his/her finger.

A reading means that is not shown may be included for reading the tip movement desirable line 82 from the transparent touch-sensitive panel 81. Based on the read data of the tip movement desirable line 82, the first treatment instrument 153 (second treatment instrument 154) may be automatically electrically controlled so that the tip thereof will trace the tip movement desirable line 82. This leads to improved efficiency in manipulating a treatment instrument.

Next, referring to FIG. 64, a treatment instrument swing stand included in the distal part of an endoscope in accordance with a ninth embodiment will be described below. FIG. 64 is a plan view showing the arrangement of components on the distal face of the distal part of the endoscope.

The observation window 109 is disposed in the upper center on the distal face of a distal part 105' of the endoscope. The air/water supply nozzle 111 and forward water outlet 112 are disposed on the right side of the observation window 109 in the drawing. The second treatment instrument passage hole 146 is bored on the left side of the observation window 109 in the drawing.

A substantially cubic treatment instrument swing stand storage member 113' is disposed below the observation window 109 on the distal face of the distal part 105' in the drawing. The illumination window 110 is disposed on the left side of the treatment instrument swing stand storage member 113'.

The observation window 109, the air/water supply nozzle 111, the forward water outlet 112, the illumination window 110, and the opening 146 of the second treatment instrument passage channel 118 which are included in the distal part 105' have the same abilities as those included in the distal part 105 of the endoscope 101C and exert the same operations.

A dual swing stand composed of an internal swing stand 182 and an external swing stand 183 is placed in the treatment instrument swing stand storage member 113'. The external swing stand 183 has the first and second rotation shaft 155a and 155b and a hollow part. The first and second rotation shaft 155a and 155b are embedded in the upper and lower internal walls of the swing stand storage member 113' so that they can rotate freely. The hollow part has a convex shape, has the two angling wire passage channels 160 fixed to the sides thereof, and has the internal swing stand 182 placed therein. Herein, the angling wires used to swing the external swing stand 183 on the first and second rotation shafts 155a and 155b are passed through the angling wire passage channels.

The internal swing stand 182 has first and second rotation shafts 155a' and 155b' held in the hollow part of the external swing stand 183 so that the first and second rotation shafts 155a' and 155b' can rotate freely. The first and second rotation shafts 155a' and 155b' are extended orthogonally to the first and second rotation shafts 155a and 155b of the external swing stand 183.

Two angling wire passage channels 160' through which angling wires used to swing the internal swing stand 182 on the first and second rotation shafts 155a' and 155b' are passed are fixed to the sides of the internal swing stand 182. The second treatment instrument passage hole 145 communicating with the first treatment instrument passage channel 117 is bored in the center of the internal swing stand 182.

In the distal part 105' having the foregoing components, the first and second rotation shafts 155a' and 155b' of the internal swing stand 182 are orthogonal to the first and second rotation shafts 155a and 155b of the external swing stand 183. When the internal swing stand 182 is swung by pulling the angling wires, the internal swing stand 182 alone swings. A treatment instrument passed through the first treatment instrument passage hole 145 of the internal swing stand 182 swings in the upward and downward directions of the drawing. When the external swing stand 183 is swung, the internal swing stand 182 swings along with the swing of the external swing stand 183. A treatment instrument passed through the first treatment instrument passage hole 145 of the internal swing stand 182 is swung in the rightward and leftward directions of the drawing.

In other words, the treatment instrument passed through the first treatment instrument passage hole 145 of the internal swing stand 182 is swung upwards and downwards by the internal swing stand 182, and swung rightwards and leftwards by the external swing stand 183.

Since the distal part 105' of the endoscope has the dual swing stand composed of the internal swing stand 182 and external swing stand 183, a treatment instrument can be swung in four directions. This leads to improved efficiency in treatment.

Figure 65:
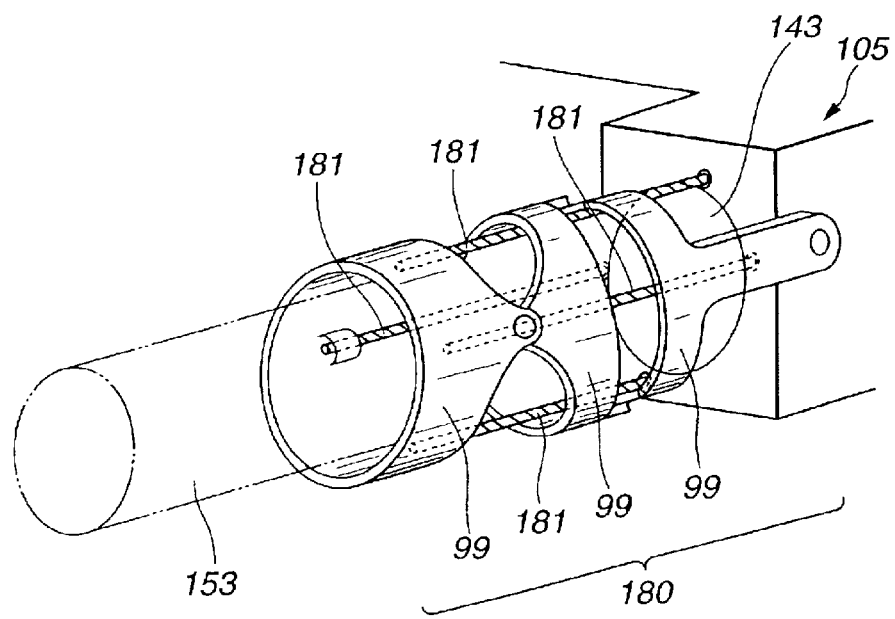
FIG. 65 is a perspective view showing a swing stand included in an endoscope in accordance with a tenth embodiment of the present invention.

Next, a swing stand included in an endoscope in accordance with a tenth embodiment will be described with reference to FIG. 65. FIG. 65 is a perspective view showing the swing stand included in the endoscope in accordance with the tenth embodiment.

The swing stand is formed with a swing tube 180 composed of a plurality of bending pieces 99. The bending pieces 99 are relatively short and cylindrical. A pair of joints is extended from the opposed lateral parts of each cylindrical bending piece 99. Owing to the joints, the preceding and succeeding bending pieces 99 are joined so that they can pivot freely. The bending pieces 99 are angled differently by 90°. Thus, the swing tube 180 is realized.

The proximal end of the swing tube 180 having the plurality of bending pieces 99 joined so that the bending pieces can pivot freely is fitted in the opening 143 of the first treatment instrument passage channel 117 included in the distal part 105. In this state, the swing tube 180 can pivot freely. Four swing tube angling wires 181 are fixed to the leading bending piece 99 of the swing tube 180.

When the swing tube 180 having the foregoing components is adopted, if the swing tube angling wires 181 are pulled, the wing tube 180 can bend upwards, downwards, rightwards, and leftwards. Consequently, a treatment instrument led out through the opening 143 of the first treatment instrument passage channel 114 and passed inside the bending pieces 99 of the swing tube 180 can swing upwards, downwards, rightwards, and leftwards. Consequently, the treatment instrument can be swung in the four directions using the one swing tube 180. This leads to improved efficiency in treatment.

Next, referring to FIG. 66 to FIG. 68, an endoscope in accordance with an eleventh embodiment of the present invention will be described below.

The present embodiment is an endoscope having an external swing stand.

Figure 66:
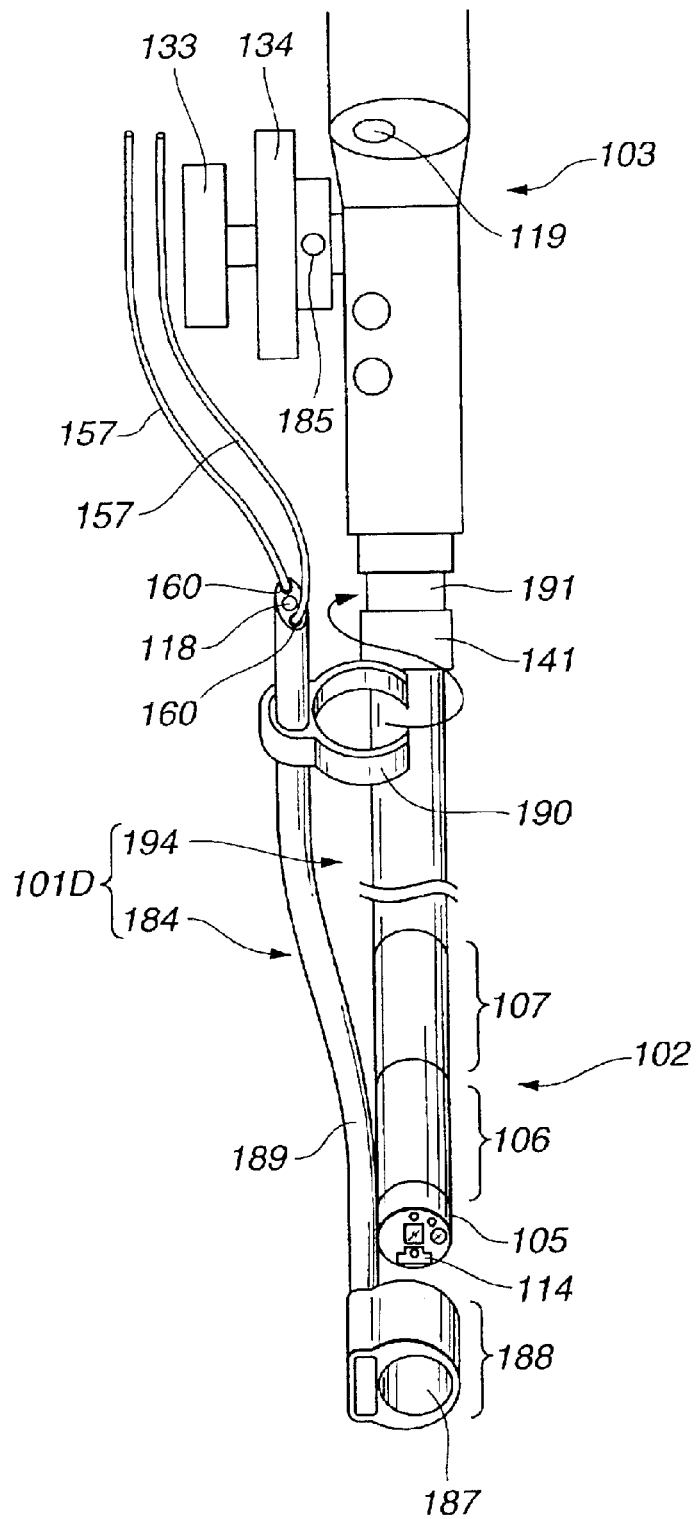
FIG. 66 to FIG. 68 are concerned with an eleventh embodiment of the present invention.

As shown in FIG. 66, an endoscope 101D consists mainly of an endoscope body 194 and a treatment swing stand-inclusive external channel 184 that is freely detachably attached to the endoscope body 194.

A first treatment instrument passage channel lies through the insertion unit 102 and operation unit 103 of the endoscope body 194. The first swing stand 114 that swings a first treatment instrument alone in only two directions and that communicates with the first treatment instrument passage channel is included in the distal part 105 of the insertion unit 102.

When the treatment instrument swing stand-inclusive external channel 184 is attached to the endoscope body 194, the first treatment instrument led out of the first swing stand 114 can be swing in directions different from the directions in which the first treatment instrument can be swung by the first swing stand 114. Thus, the first treatment instrument led out of the first swing stand 114 can be swung in four directions.

The treatment instrument swing stand-inclusive external channel 184 consists mainly of a distal external channel part 188, which can be mounted on the periphery of the distal part 105 of the endoscope body 194, and a channel member 189.

Figure 68:
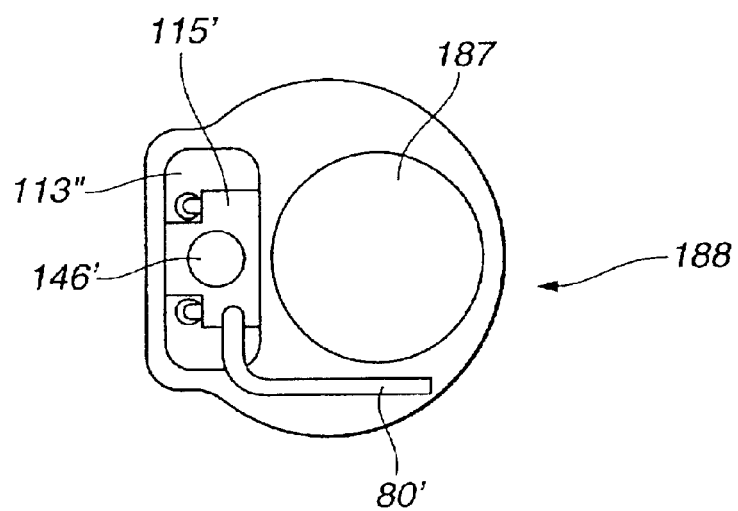

The distal external channel part 188 has, as shown in FIG. 68, a distal part fitting hole 187 in which the periphery of the distal part 105 of the endoscope body 194 is fitted, and a second treatment instrument swing stand storage member 113" that is disposed on the left side of the distal part fitting hole 187. A second treatment instrument swing stand 115' having a second treatment instrument passage hole 146' and a raising bar 80' is placed in the second treatment instrument swing stand storage member 113".

In short, the distal external channel portion 188 has the second treatment instrument swing stand 115' identical to the second treatment instrument swing stand 115 described in conjunction with FIG. 53.

The first treatment instrument passage hole 146' of the second treatment instrument swing stand 115' communicates with the second treatment instrument passage channel 118 lying through the channel member 189. Furthermore, two angling wires 157 used to swing the second treatment instrument swing stand 115' are passed through the channel member 189.

Figure 67:
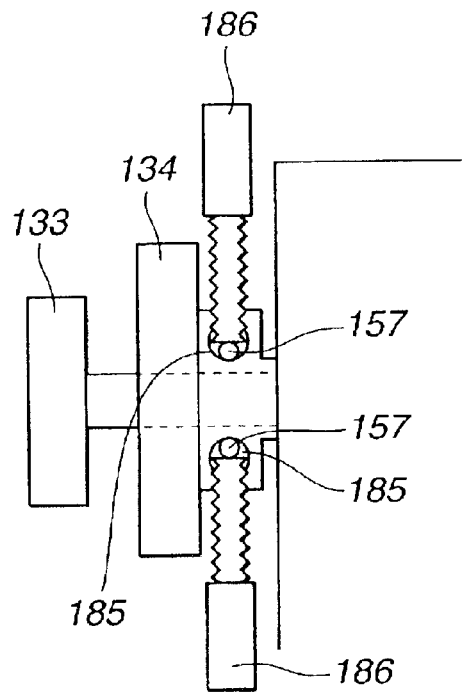

The angling wires 157 are, as shown in FIG. 67, routed to the angling wire fitting ports 185 that are bored in the second treatment instrument swing stand manipulation knob 134 included in the operation unit 103, and locked using wire lock members 186.

Specifically, when the second treatment instrument swing stand manipulation knob 134 is turned, the angling wires 157 are pulled alternately. This causes the second treatment instrument swing stand 115' to swing. With the swing of the second treatment instrument swing stand 115', a second treatment instrument passed through the second treatment instrument passage channel 118 and led out of the second treatment instrument swing stand 115' is swung. Furthermore, the swing of the second treatment instrument swing stand 115' causes the first treatment instrument led out of the first treatment instrument swing stand 114 included in the distal part 105 to swing or rise due to the raising bar 80'.

In other words, when the treatment instrument swing stand-inclusive external channel 184 is attached to the endoscope body 194 with which only one type of treatment instrument can be used in combination and which permits the treatment instrument to swing in only two directions, two second treatment instruments become usable.

In this case, the treatment instrument swing stand-inclusive external channel 184 is attached so that the second treatment instrument swing stand 115' will lie orthogonally to the first swing stand 114 included in the distal part 105 of the endoscope. Thus, the first treatment instrument in the distal part 105 can be swung in four directions owing to the swing of the second treatment instrument swing stand 115'.

Consequently, swinging can be freely designated depending on the type of treatment instrument to be used in combination with the endoscope 101D. This leads to improved efficiency in treatment to be performed using the endoscope 101D.

Moreover, the treatment instrument swing stand-inclusive external channel 184 can be attached to an endoscope whenever it is needed. Therefore, the endoscope body 194 to which the treatment instrument swing stand-inclusive external channel 184 is not attached can be designed thinly.

Incidentally, the channel member 189 included in the treatment instrument swing stand-inclusive external channel 184 has a proximal mount 190. The proximal mount 190 is fitted in a concave part 191 of the insertion unit anti-breakage member 141 of the endoscope body 194. Consequently, the treatment instrument swing stand-inclusive external channel 184 can be reliably held and locked by the distal part 105 of the insertion unit 102 of the endoscope body 194 and the insertion unit anti-breakage member 141.

Incidentally, the treatment instrument swing stand-inclusive external channel 184 may be of a disposable type.

Referring to FIG. 69 to FIG. 72, an endoscope in accordance with a twelfth embodiment of the present invention will be described below. The endoscope of the present embodiment is basically characterized in that the distal opening portion of a treatment instrument passage channel is disposed behind an observation window in an insertion unit. Thus, even a treatment instrument having a long distal hard member can be caught in the field of view for observation so that it can be observed easily. This is intended to facilitate treatment.

The features of the present embodiment will be described practically.

Figure 70:
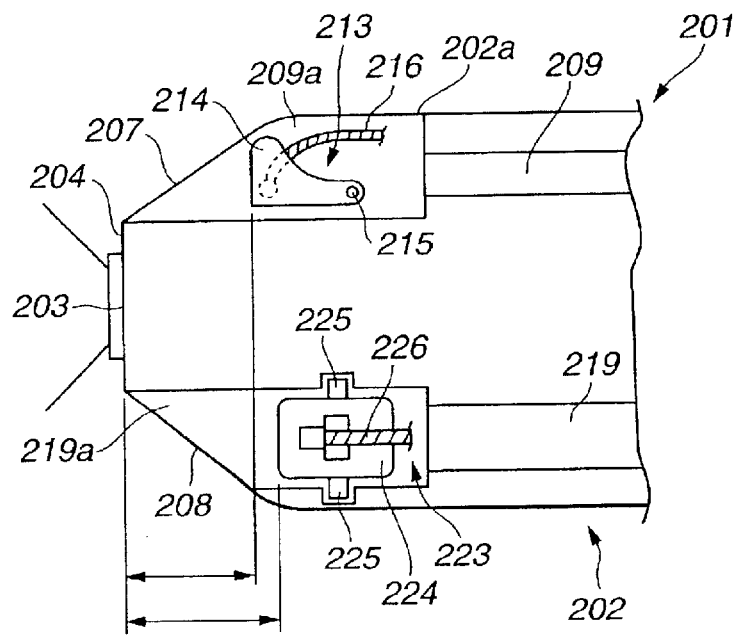

An endoscope 201 of the present embodiment has, as shown in FIG. 70, a mount 204 for an observation window 203, through which a lesion is observed, disposed in the distal part of an insertion unit 202 that is elongated and soft and inserted into a lumen.

The observation window mount 204 is realized with a plane formed substantially orthogonally to the direction of the axial center of the insertion unit 202. The observation window mount 204 has one observation window 203, two illumination windows 205, and an air/water supply nozzle 206. The observation window 203 is disposed substantially in the center of the observation window mount 204. The two illumination windows 205 are disposed on both sides of the observation window 203. Incidentally, the air/water supply nozzle 206 is oriented towards the observation window 203. Cleansing solution or air jetted out of the air/water supply nozzle 206 is sprayed directly to the observation window 203.

Moreover, inclined surfaces 207 and 208 that are inclined relative to the directions orthogonal to the direction of the axial center of the insertion unit 202 are, as shown in FIG. 70, extended from both edges of (the upper and lower edges in FIG. 69) the observation window mount 204. The first distal opening portion 209a of a first treatment instrument passage channel 209 is disposed substantially in the center of the upper inclined surface 207 of the observation window mount 204.

A first treatment instrument, for example, clamp forceps 212 (FIG. 71) are inserted into the first treatment instrument passage channel 209 so that they can be removed. Furthermore, a hemostatic treatment instrument passage channel 210 and a forward water outlet 211 are disposed in the opposite sides of the upper inclined surface 207.

Moreover, a first treatment instrument swinging mechanism 213 for swinging the clamp forceps 212, which are thrust forwards from the first distal opening portion 209a of the first treatment instrument passage channel 209, in the upward and downward directions (first directions of swing) is included in the first distal opening portion 209a.

The first treatment instrument swinging mechanism 213 includes an upward/downward raising stand (swing stand) 214 that swings the clamp forceps 212 or any other treatment instrument, which is thrust forwards from the distal opening portion 209a, in the upward and downward directions. The upward/downward raising stand 214 has the proximal end thereof supported on the side walls of the distal opening portion 209a so that it can freely pivot on a rotation shaft 215.

Herein, an escape groove 202a is formed in the periphery of the distal part of the insertion unit 202 so that it will be opposed to the first distal opening portion 209a of the first treatment instrument passage channel 209. When the clamp forceps 212 jutted out of the first distal opening portion 209a are raised by the upward/downward raising stand 214, the clamp forceps 212 enters the escape groove 202a so as to avoid interference with the clamp forceps 212.

Furthermore, the distal end of a raising wire 216 is fixed to the distal part of the upward/downward raising stand 214. The proximal end of the raising wire 216 is led to the proximal part of the insertion unit 202 included in the endoscope 201. An upward/downward raising lever and others that are not shown are included in a proximal operation unit coupled to the proximal part of the insertion unit 202. The raising wire 216 is pulled by handling the upward/downward raising lever, whereby the upward/downward raising stand 214 is swung on the rotation shaft 215 in the upward and downward directions indicated with arrows A in FIG. 1.

Incidentally, when the first treatment instrument swinging mechanism 213 is not raised, the clamp forceps 212 or any other treatment instrument is jutted out of the first distal opening portion 209a substantially in the axial direction of the insertion unit 202.

Moreover, the clamp forceps 212 include an elongated wire-like inserting member 217, a pair of clamping members 218a and 218b that can open or close and that are coupled to the distal end of the inserting member 217, and a forceps manipulating member that is not shown and that is coupled to the proximal end of the inserting member 217. The pair of clamping members 218a and 218b is opened or closed by handling the forceps manipulating member, whereby a living tissue is clamped by the clamping members 218a and 218b.

Figure 69:
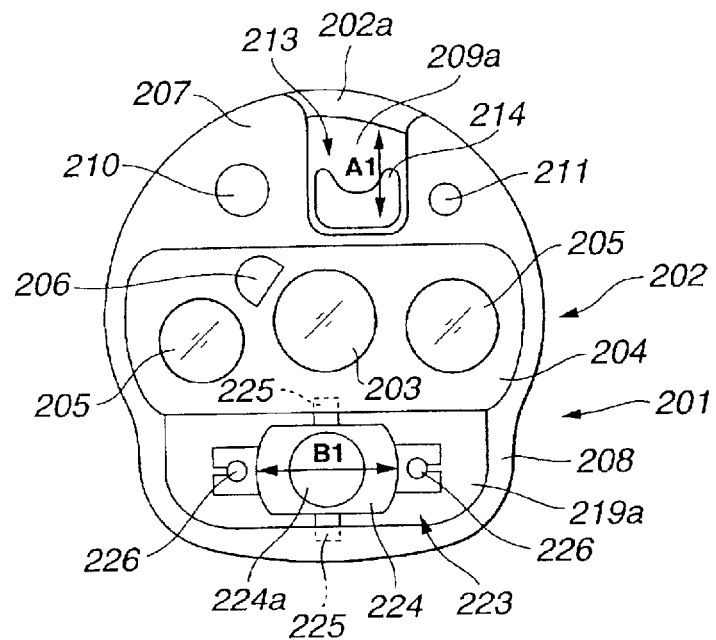
FIG. 69 to FIG. 72 are concerned with a twelfth embodiment of the present invention.

Moreover, a second distal opening portion 219a of a second treatment instrument passage channel 219 is contained in the inclined surface 208 extending below the observation window mount 204. The sideways width of the second distal opening portion 219a of the second treatment instrument passage channel 219 is, as shown in FIG. 69, substantially identical to the sideways width of the observation window mount 204. The second treatment instrument passage channel 219 opens substantially in the center of the sideways width of the second distal opening portion 219a.

Furthermore, a second treatment instrument, for example, a diathermic knife 220 (FIG. 71) is inserted into the second treatment instrument passage channel 219 so that it can be removed. The diathermic knife 220 includes an elongated wire-like inserting member 221, a treating member 222 distal to the inserting member 221, and a manipulating member that is not shown and that is proximal to the inserting member 221.

Moreover, a second treatment instrument swinging mechanism 223 for swinging the diathermic knife 220, which is thrust forwards from the second distal opening portion 219a of the second treatment instrument passage channel 219, in the rightward and leftward directions (second directions of swing) is included in the second distal opening portion 219a.

The second treatment instrument swinging mechanism 223 includes a rightward/leftward swing stand 224 that swings the diathermic knife 220 or any other treatment instrument, which is thrust forward from the second distal opening portion 219a, in the rightward and leftward directions. The rightward/leftward swing stand 224 has the proximal part thereof supported on the upper and lower walls of the second distal opening portion 219a so that it can swing on rotation shafts 225 that are formed with upward and downward extensions as shown in FIG. 69 and FIG. 70.

Furthermore, a treatment instrument passage hole 224a through which the second treatment instrument such as the diathermic knife 220 is passed is formed in the center of the rightward/leftward swing stand 224. The second treatment instrument such as the diathermic knife 220 is passed through the treatment instrument passage hole 224a.

The distal ends of two swinging wires 226 are fixed to both the sides of the rightward/leftward swing stand 224. The proximal ends of the swinging wires 226 are led to the proximal part of the insertion unit 202 of the endoscope 201. Incidentally, a proximal operation unit includes a rightward/leftward swinging lever and others that are not shown. The right and left swinging wires 26 are advanced or withdrawn by handling the rightward/leftward swinging lever. Consequently, the rightward/leftward swing stand 224 swings on the rotation shafts 225 in the rightward and leftward directions indicated with arrows B1 in FIG. 69.

Furthermore, in an initial state in which the rightward/leftward swinging lever is not handled, the rightward/leftward swing stand 224 included in the present embodiment is held at a neutral position that is substantially in the center of the sideways width of the second distal opening portion 219a. In this state, the second treatment instrument such as the diathermic knife 220 is jutted out of the second distal opening portion 219a substantially in the axial direction of the insertion unit 202.

Incidentally, according to the present embodiment, the distal ends of the two swinging wires 226 are fixed to both the sides of the rightward/leftward swing stand 224. Alternatively, one swinging wire 226 may be fixed to one side of the rightward/leftward swing stand 224 so that the rightward/leftward swing stand 224 will be swung in the rightward and leftward directions using the one swinging wire 226.

Next, operations to be exerted by the present embodiment having the foregoing features will be described below. When the endoscope 201 of a front-vision type in accordance with the present embodiment is employed, the insertion unit 202 of the endoscope 201 is inserted into a body cavity. After the distal part of the insertion unit 202 is led to an intended region, the first treatment instrument such as the clamp forceps 212 are inserted into the body cavity through the first treatment instrument passage channel 209. Moreover, the second treatment instrument such as the diathermic knife 220 is inserted into the body cavity through the second treatment instrument passage channel 219.

Figure 71:
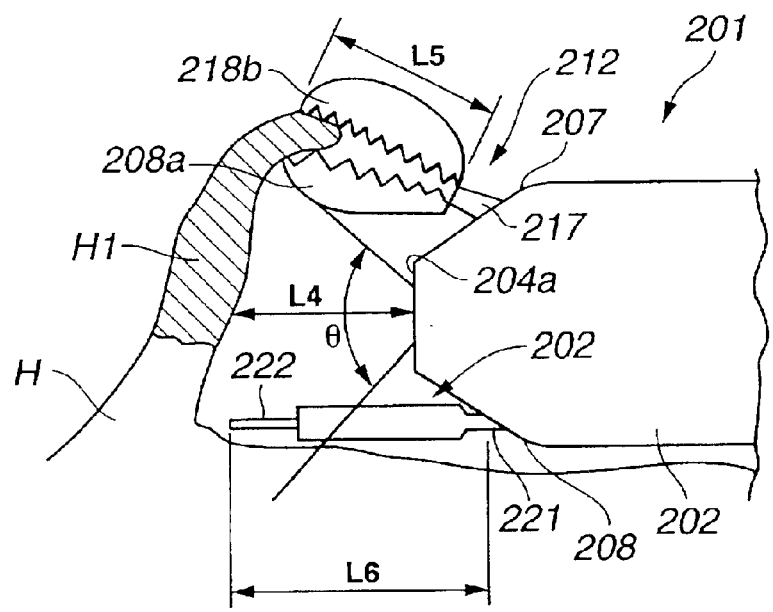

Herein, the clamp forceps 212 are thrust forwards from the first distal opening portion 209a of the first treatment instrument passage channel 209, while the diathermic knife 220 is thrust forwards from the second distal opening portion 219a of the second treatment instrument passage channel 219. At this time, as shown in FIG. 71, the clamp forceps 212 are inserted into an observable range θ that can be observed through the observation window 203 of the endoscope 201 from the upper edge of the observable range, and the diathermic knife 220 is inserted thereinto from the lower edge thereof.

Figure 72:
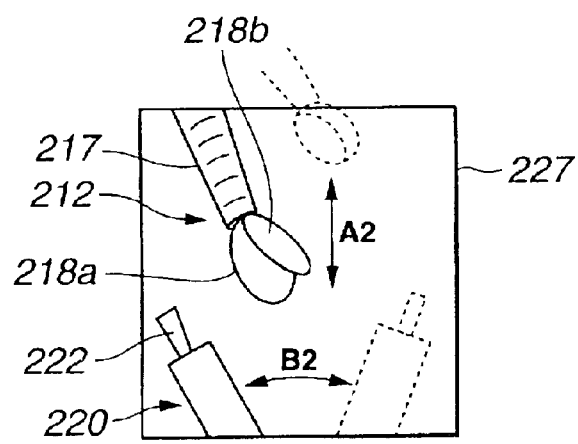

Consequently, as shown in FIG. 72, an image of the diathermic knife 220 is superposed on the lower part of a view image 227 that renders a view observed through the observation window 203 of the endoscope 201. An image of the clamp forceps 212 is superposed on the upper part of the view image 227.

Moreover, in the initial state in which the first treatment instrument swinging mechanism 213 is not operated, the clamp forceps 212 are jetted out of the first distal opening portion 209a substantially in the axial direction of the insertion unit 202. Furthermore, in the initial state in which the rightward/leftward swinging lever is not handled, the rightward/leftward swing stand 224 is held at the neutral position that lies substantially in the center of the sideways width of the second distal opening portion 219a. In this state, the second treatment instrument such as the diathermic knife 220 is jutted out of the second distal opening portion 219a substantially in the axial direction of the insertion unit 202.

Moreover, in order to operate the first treatment instrument swinging mechanism 213, the raising wire 216 is pulled by handling the proximal upward/downward raising lever. Along with the pulling of the raising wire 216, the upward/downward raising stand 214 is swung on the rotation shaft 215 in the upward and downward directions indicated with arrows A1 in FIG. 69.

Consequently, the image of the clamp forceps 212 jutted out of the first distal opening portion 209a moves in the upward and downward directions of the view image 227, which renders a view observed through the observation window 203 of the endoscope 201, as indicated with arrows A2 in FIG. 72.

Moreover, the magnitude of jut by which the clamp forceps 212 are jutted out of the first distal opening portion 209a is adjusted by manipulating the clamp forceps 212 optimally. Furthermore, when the pair of clamping members 218a and 218b is opened and closed using the forceps manipulating member, a lesion H1 of a living tissue H is clamped by the clamping members 218a and 218b. Thereafter, the lesion H1 of the living tissue H clamped by the clamp forceps 212 is lifted.

Thereafter, the root of the lesion H1 of the living tissue H lifted using the clamp forceps 212 is cut using the second treatment instrument such as the diathermic knife 220. At this time, the magnitude of jut by which the diathermic knife 220 is jutted out of the second distal opening portion 219a is adjusted by manipulating the diathermic knife 220 optimally.

Furthermore, by operating the second treatment instrument swinging mechanism 223, the rightward/leftward swing stand 224 is moved in the rightward and leftward directions indicated with arrows B1 in FIG. 69. At this time, the diathermic knife 220 is moved together with the rightward/leftward swing stand 224 in the rightward and leftward directions indicated with arrows B2 in FIG. 72. The root of the lesion H1 of the living tissue H is then cut. Consequently, as shown in FIG. 71, the mucosa can be resected using various kinds of treatment instruments including the clamp forceps 212 and diathermic knife 220 in combination with the endoscope 201.

The inclusion of the foregoing features provides advantages described below. That is to say, the endoscope 201 of the present embodiment has the distal opening portions 209a and 219a of the treatment instrument passage channels arranged on both the edges of the observation window mount 204 contained in the distal face of the insertion unit 202. The first distal opening portion 209a of the first treatment instrument passage channel 209 includes the first treatment instrument swinging mechanism 213 that swings the clamp forceps 212, which are thrust forwards from the first distal opening portion 209a, in the upward and downward directions. The second opening portion 219a of the second treatment instrument passage channel 219 includes the second treatment instrument swinging mechanism 223 that swings the diathermic knife 220, which is thrust forwards from the second distal opening portion 219a, in the rightward and leftward directions.

Consequently, an image of the clamp forceps 212 jutted out of the first distal opening portion 209a located on one edge of the observation window mount 204 is superposed on the upper part of the view image 227 rendering a view observed through the observation window 203 of the endoscope 201. An image of the diathermic knife 220 jutted out of the second distal opening portion 219a located on the other edge of the observation window mount 204 is superposed on the lower part of the view image 227.

While the lesion H1 of the living tissue H clamped by the clamp forceps 212 whose image is superposed on the upper part of the view image 227 is held lifted, the rightward/leftward swing stand 224 which is included in the second treatment instrument swinging mechanism 223 and whose image is superposed on the lower part of the view image 227 is swung rightwards and leftwards. Consequently, the root of the lesion H1 of the living tissue H can be resected over a wide range owing to the rightward and leftward swings of the diathermic knife 220.

Moreover, the endoscope 201 of the present embodiment has the upward/downward raising stand 214 and rightward/leftward swing stand 224 located behind the observation window 203. Therefore, as shown in FIG. 71, although the distance L4 between the observation window 203 and a target region such as the lesion H1 of the living tissue H is short, the length by which the clamp forceps 212 are jutted out of the first distal opening portion 209a or the length by which the diathermic knife 220 is jutted out of the second distal opening portion 219a can be set to a relatively large value.

Consequently, as shown in FIG. 71, even when a treatment instrument whose hard member has a large length, such as, the clamp forceps 212 whose clamping members 218a and 218b have length L5 or the diathermic knife 220 whose treating member 222 has length L6 is used, a region to be treated such as the lesion H1 will not largely deviate from a proper focal point at which the lesion can be observed distinctly through the observation window 203 of the endoscope 201. Thus, the treatment instrument whose hard member has a large length can be used effectively.

Furthermore, the endoscope 201 of the present embodiment has the inclined surface 7 formed above the observation window mount 204. Moreover, the inclined surface 208 is formed below the observation window mount 204. Therefore, although the outer diameter of the distal part is relatively large, the distal part can be inserted into a body cavity smoothly.

Moreover, no built-in component is present in a direction of raising in which the upward/downward raising stand 214 included in the first treatment instrument swinging mechanism 213 is raised and in a direction of swing in which the rightward/leftward swing stand 224 included in the second treatment instrument swinging mechanism 223 is swung. Therefore, a raising-enabled range within which the upward/downward raising stand 214 can be raised and a swingable range within which the rightward/leftward swing stand 224 can be swung can be made larger than they conventionally are. Consequently, the mucosa of the lesion H1 of the living tissue H can be resected over a wide range. This means that the mucosa of the lesion H1 of the living tissue H can be resected efficiently.

Figure 73A:
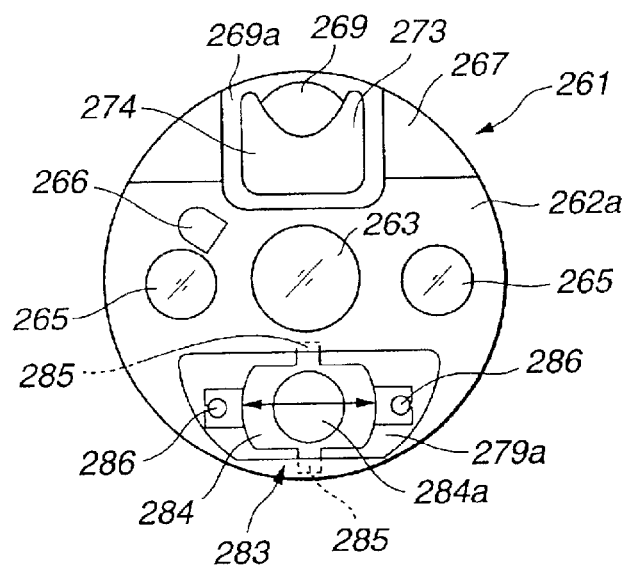
FIG. 73A and FIG. 73B are concerned with a thirteenth embodiment of the present invention.
Figure 73B:
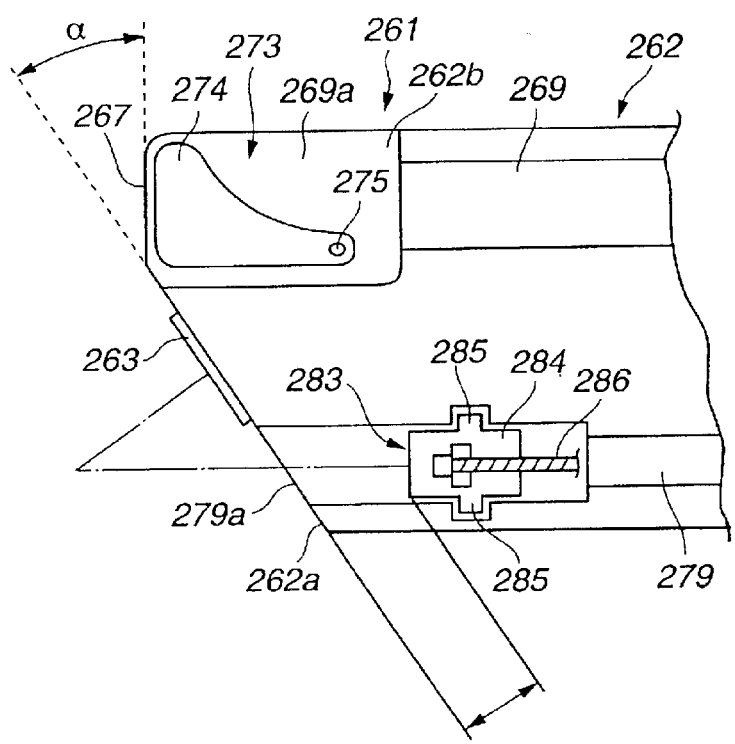

FIG. 73A and FIG. 73B show a thirteenth embodiment of the present invention. According to the present embodiment, an endoscope 261 of an oblique-vision type is adopted on behalf of the endoscope 201 of a front-vision type in accordance with the twelfth embodiment (see FIG. 69 to FIG. 72).

The endoscope 261 of an oblique-vision type has, as shown in FIG. 73B, an inclined surface 262a formed as part of the distal part of an elongated soft insertion unit 262 that is inserted into a lumen. The inclined surface 262a is inclined with respect to a direction orthogonal to the direction of the axial center of the insertion unit 262. As shown in FIG. 73A, an observation window 263 for observation is contained substantially in the center of the inclined surface 262a.

The inclined surface 262a contains one observation window 263, two illumination windows 265, and an air/water supply nozzle 266. The observation window 263 is located substantially in the center of the inclined surface 262a. The two illumination windows 265 are arranged on both the sides of the observation window 263.

A direction of emission in which illumination light is emitted through the two illumination windows 265 and a direction of observation permitted through the observation window 263 are set to the same direction. Incidentally, the air/water supply nozzle 266 is oriented towards the observation window 263. Cleansing solution or air to be jetted out of the air/water supply nozzle 266 is sprayed directly to the observation window 263.

Moreover, a first distal opening portion 269a of a first treatment instrument passage channel 269 is disposed substantially in the center of an area spread above the inclined surface 262a. A first treatment instrument, for example, clamp forceps 212 (FIG. 71) are inserted into the first treatment instrument passage channel 269.

Furthermore, a bent surface 267 that is bent in a direction different from a direction of inclination in which the inclined surface 262a is inclined, for example, a direction orthogonal to the direction of the axial center of the insertion unit 262 is formed above the inclined surface 262a adjacently to the first distal opening portion 269a. The direction of bending in which the bent surface 267 is bent and the direction of inclination in which the inclined surface 262a is inclined meet at a proper angle α.

Moreover, the first distal opening portion 269a of the first treatment instrument passage channel 269 includes a first treatment instrument swinging mechanism 273 that swings the clamp forceps 212, which are thrust forwards from the first distal opening portion 269a, in the upward and downward directions (first directions of swing).

The first treatment instrument swinging mechanism 273 includes an upward/downward raising stand (swing stand) 274 that swings a treatment instrument such as the clamp forceps 212, which are thrust forwards from the distal opening portion 269a, in the upward and downward directions. The upward/downward raising stand 274 has the proximal end thereof supported on the side walls of the distal opening portion 269a so that it can freely pivot on a rotation shaft 275.

Herein, an escape groove 262b is formed in the periphery of the distal part of the insertion unit 262 so that it will be opposed to the first distal opening portion 269a of the first treatment instrument passage channel 269. When the clamp forceps 212 to be jutted out of the first distal opening portion 269a are raised by the upward/downward raising stand 274, the clamp forceps 212 escape to the escape groove so as to avoid interference with the distal part.

Furthermore, the distal end of a raising wire that is not shown is fixed to the distal end of the upward/downward raising stand 274. The proximal end of the raising wire is led to the proximal part of the insertion unit 262 of the endoscope 261. Incidentally, a proximal operation unit proximal to the insertion unit 262 has an upward/downward raising lever and others that are not shown. The raising wire is pulled by handling the upward/downward raising lever, whereby the upward/downward raising stand 274 is swung on the rotation shaft 275 in the upward and downward directions.

Incidentally, when the first treatment instrument swinging mechanism 273 is not raised, the treatment instrument such as the clamp forceps 212 are jutted out of the first distal opening portion 269a substantially in the axial direction of the insertion unit 262.

Moreover, a second distal opening portion 279a of a second treatment instrument passage channel 279 that has a sideways oblong section opens upon outside below the inclined surface 262a. The second treatment instrument passage channel 279 is located substantially in the center of the sideways width of the second distal opening portion 279a. Furthermore, a second treatment instrument, for example, the diathermic knife 220 (FIG. 71) can be inserted into or removed from the second treatment instrument passage channel 279.

Moreover, the second distal opening portion 279a of the second treatment instrument passage channel 279 includes a second treatment instrument swinging mechanism 283 that swings the diathermic knife 220, which is thrust forwards from the second distal opening portion 279a, in the rightward and leftward directions (second directions of swing).

The second treatment instrument swinging mechanism 283 includes a rightward/leftward swing stand 284 that swings the treatment instrument such as the diathermic knife 220, which are thrust forwards from the second distal opening portion 279a, in the rightward and leftward directions. The rightward/leftward swing stand 284 has the proximal part thereof supported on the upper and lower walls of the second distal opening portion 279a so that it can turn freely on rotation shafts 285. The rotation shafts 285 are formed as extensions of the top and bottom of the rightward/leftward swing stand 284 in FIG. 73B.

Furthermore, a treatment instrument passage hole 284a through which the second instrument member such as the diathermic knife 220 is passed is formed in the center of the rightward/leftward swing stand 284. The second treatment instrument such as the diathermic knife 220 is passed through the treatment instrument passage hole 284a.

Moreover, the distal ends of two swinging wires 286 are fixed to both the sides of the rightward/leftward swing stand 284. The proximal ends of the swinging wires 286 are extended to the proximal part of the insertion unit 262 of the endoscope 261. Incidentally, a proximal operation unit includes a rightward/leftward swinging lever and others which are not shown. The rightward and leftward swinging wires 286 are advanced or withdrawn by handling the rightward/leftward swinging lever. Consequently, the rightward/leftward swing stand 284 is swung on the rotation shafts 285 in the rightward and leftward directions indicated with arrows in FIG. 73A.

Furthermore, in an initial state in which the rightward/leftward swinging lever is not handled, the rightward/leftward swing stand 284 is held neutral substantially in the center of the sideways width of the second distal opening portion 279a. In this state, the second treatment instrument such as the diathermic knife 220 is jutted out of the second distal opening portion 279a substantially in the axial direction of the insertion unit 262.

According to the present embodiment, the distal ends of the two swinging wires 286 are fixed to both the sides of the rightward/leftward swing stand 284. Alternatively, the distal end of one swinging wire 286 maybe fixed to one side of the rightward/leftward swing stand 284, and the rightward/leftward swing stand 284 may thus be swung in the rightward and leftward directions using the one swinging wire. Moreover, the rightward/leftward swing stand 284 may not be automatically held neutral.

The inclusion of the foregoing features provides the advantages described below. That is to say, the endoscope 261 of the present embodiment has the observation window 263 disposed substantially in the center of the distal inclined surface 262a of the insertion unit 262. The first distal opening portion 269a of the first treatment instrument passage channel 269 is disposed above the observation window 263 contained in the inclined surface 262a. The second distal opening portion 279a of the second treatment instrument passage channel 279 which has a sideways oblong section is disposed below the inclined surface 262a.

Consequently, an image of the clamp forceps 212 jutted out of the first distal opening portion 269a above the observation window 263 contained in the inclined surface 262a is located at the upper edge of the view image 227 rendering a view seen through the observation window 263 of the endoscope 261. An image of the diathermic knife 220 jutted out of the second distal opening portion 279a below the inclined surface 262a is located at the lower edge of the view image 227.

The lesion H1 of the living tissue H clamped by the clamp forceps 212 whose image is located at the upper edge of the view image 227 is held lifted. In this state, the rightward/leftward swing stand 284 included in the second treatment instrument swinging mechanism 283 located below the view rendered by the view image 227 is swung rightwards and leftwards. Consequently, the root of the lesion H1 of the living tissue H can be resected over a wide range due to the rightward and leftward swings of the diathermic knife 220.

Moreover, the endoscope 261 of the present embodiment has the rightward/leftward swing stand 284 located behind the observation window 263. Even if the distance L4 between the observation window 263 and a target region such as the lesion H1 of the living tissue H is short, the length by which the diathermic knife 220 is jutted out of the second distal opening portion 279a can be set to a relatively large value. Consequently, even when a treatment instrument having a long hard member, such as, the diathermic knife 220 having the long treating member 222 is employed, a region to be treated such as the lesion H1 will not be displaced from a proper focal point at which the lesion can be observed distinctly through the observation window 263 of the endoscope 261. Thus, the treatment instrument having a long hard member can be used effectively.

Furthermore, the endoscope 261 of the present embodiment has the inclined surface 262a formed as the distal face of the insertion unit 262. Therefore, although the diameter of the distal part is relatively large, the distal part can be inserted into a body cavity smoothly.

Moreover, according to the present embodiment, no built-in component is present in a direction of raising in which the upward/downward raising stand 274 included in the first treatment instrument swinging mechanism 273 is raised and in a direction of swinging in which the rightward/leftward swing stand 284 included in the second treatment instrument swinging mechanism 283 is swung. A rising-enabled range in which the upward/downward raising stand 274 can be raised and a swingable range in which the rightward/leftward swing stand 284 can be swung can be made wider than they conventionally are. Consequently, the mucosa of the lesion H1 of the living tissue H can be resected over a wide range. This means that the mucosa of the lesion H1 of the living tissue H can be resected efficiently.

Furthermore, in the endoscope 261 of the present embodiment, the longitudinal section of the insertion unit 262 in the axial direction thereof is as shown in FIG. 73B. In this state, the centerline of a field of view spread ahead of the observation window 263 crosses the direction of jutting in which the diathermic knife 220 is jutted by the rightward/leftward swing stand 284. Part of the lesion H1 or the like to be resected with the treating member 222 of the diathermic knife 220 can be caught in the center of the field of view spread ahead of the observation window 263 of the endoscope 261. Therefore, part of the lesion H1 or the like to be resected with the treating member 222 of the diathermic knife 220 can be observed easily.

Next, referring to FIG. 74 to FIG. 86, a fourteenth embodiment of the present invention will be described below.

Figure 74:
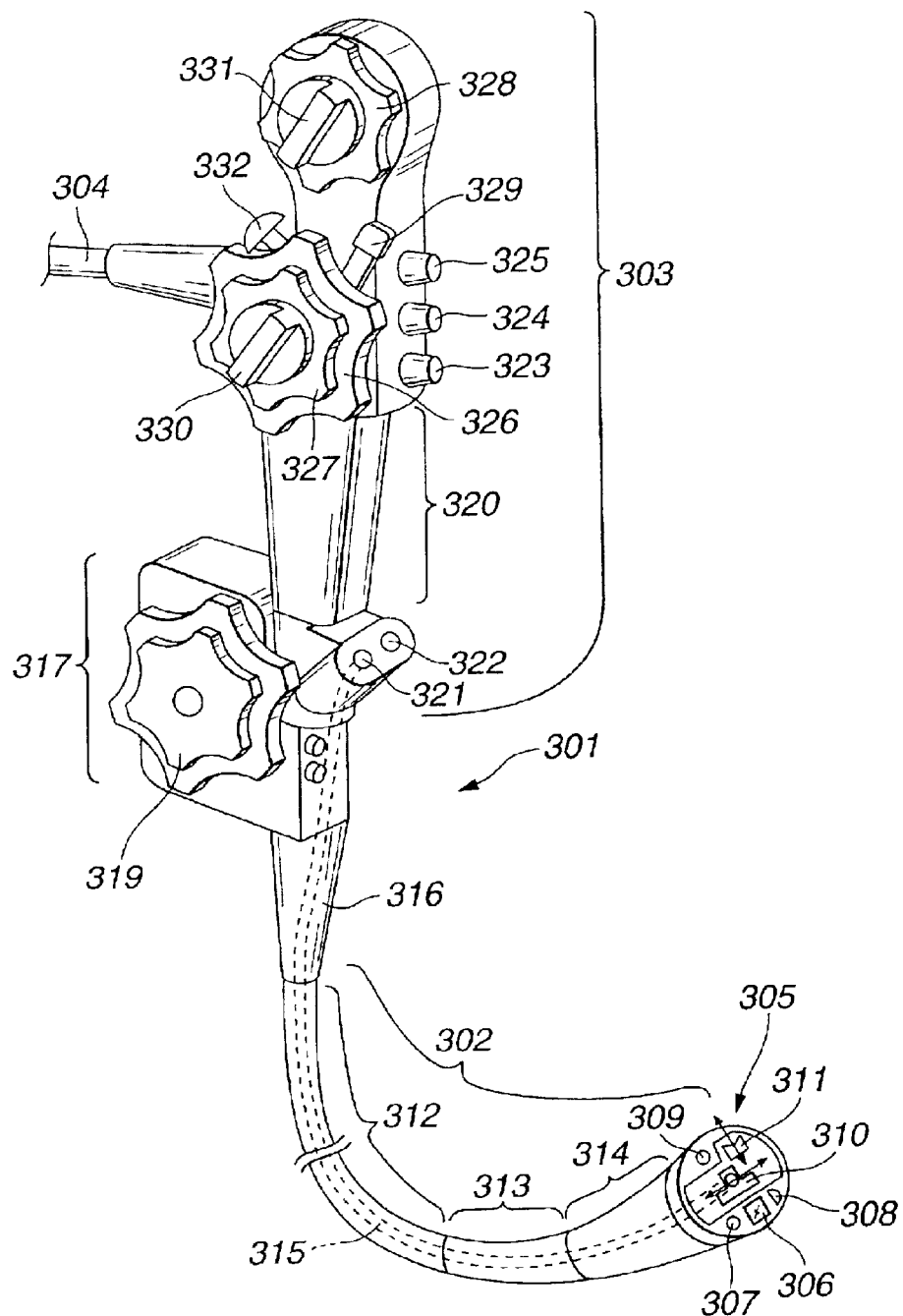

As shown in FIG. 74, an endoscope 301 of the fourteenth embodiment of the present invention includes an insertion unit 302 and an operation unit 303. A universal cord 304 containing a light guide and others is routed to the operation unit 303.

A distal component assembly 305 included in the insertion unit 302 includes an observation window 306, an illumination window 307, an air/water supply nozzle 308, a forward water outlet 309, a first treatment instrument swing stand 310, and a second treatment instrument swing stand 311. In the present embodiment, the first treatment instrument swing stand 310 moves in the rightward and leftward directions of the endoscope, while the second treatment instrument swing stand 311 moves in the upward and downward directions thereof.

The insertion unit 302 has a flexible tube 312, a second bending section 313, and a first bending section 314 joined in that order from the end thereof adjacent to the operation unit 303. The second bending section 313 can bend in two directions of the upward and downward directions or rightward and leftward directions, while the first bending section 314 can bend in four directions of the upward, downward, rightward, and leftward directions. Furthermore, a first treatment instrument passage channel 315 and a second treatment instrument passage channel (not shown) lie through the insertion unit 302.

Figure 85A:
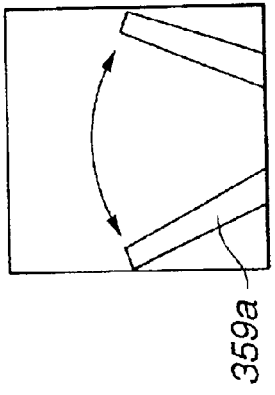

The distal opening of the first treatment instrument passage channel 315 communicates with the first treatment instrument swing stand 310, while the distal opening of the second treatment passage channel (not shown) communicates with the second treatment instrument swing stand 311. In this case, on a monitor, as shown in FIG. 85A, an image of a treatment instrument 359a is moved due to the first treatment instrument swing stand 310, and an image of a treatment instrument 359b is moved due to the second treatment instrument swing stand 311.

An anti-breakage member 316 is mounted on the periphery of a joint joining the operation unit 303 and insertion unit 302. A swing stand manipulator 317 with which the first treatment instrument swing stand 310 is remotely manipulated is disposed near the distal end of the operation unit 303.

Figure 75:
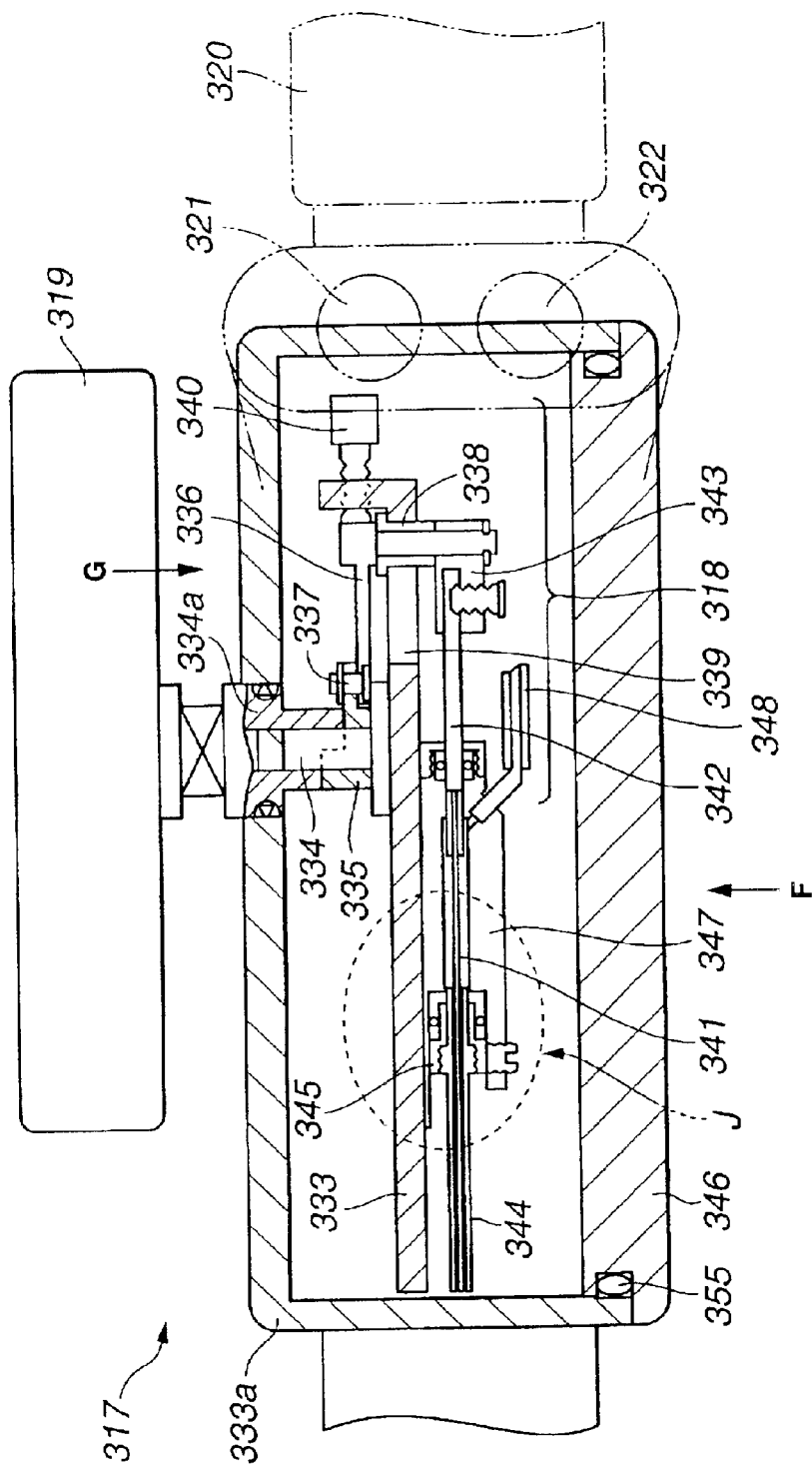

A first treatment instrument swing stand manipulating mechanism 318 is, as shown in FIG. 75, included in the swing stand manipulator 317. A first swing stand manipulation knob 319 that is part of the first treatment instrument swing stand manipulating mechanism 318 is disposed on the external surface of the swing stand manipulator 317.

As shown in FIG. 74, the operation unit 303 includes a grip 320. A first operation unit-side opening 321 of a first treatment instrument passage channel 315 and a second operation unit-side opening 322 of a second treatment instrument passage channel (not shown) are disposed ahead of the grip 320.

The first operation unit-side opening 321 is linked to the first treatment instrument swing stand 310 by the first treatment instrument passage channel 315. Likewise, the second operation unit-side opening 322 is linked to the second treatment instrument swing stand 311 by the second treatment instrument passage channel (not shown). Incidentally, the first operation unit-side opening 321 is disposed on the side of the endoscope on which the first swing stand manipulation knob 319 is disposed.

An air/water supply control button 323, a suction control button 324, an image record button 325, first bending section manipulation knobs 326 and 327, and a second bending section manipulation knob 328 are disposed behind the grip 320. The first bending section manipulation knob 326 is used to bend the first bending section in the upward or downward direction of the endoscope, while the first bending section manipulation knob 327 is used to bend it in the rightward or leftward direction thereof. Moreover, the second bending section manipulation knob 328 is used to bend the second bending section in the upward or downward direction, or in the rightward or leftward direction.

Furthermore, the turn and lock of the first bending section manipulation knob 326 are switched using a first turn/lock lever 329. The turn and lock of the first bending section manipulation knob 327 are switched using a first turn/lock knob 330. Moreover, the turn and lock of the second bending section manipulation knob 328 are switched using a second turn/lock knob 331.

A second treatment instrument swing stand manipulating mechanism (not shown) for remotely manipulating the second treatment instrument swing stand 311 is incorporated in the operation unit 303. A second swing stand manipulation knob 332 that is part of the second treatment instrument swing stand manipulating mechanism is disposed on the external surface of the manipulation unit 303.

Figure 80:
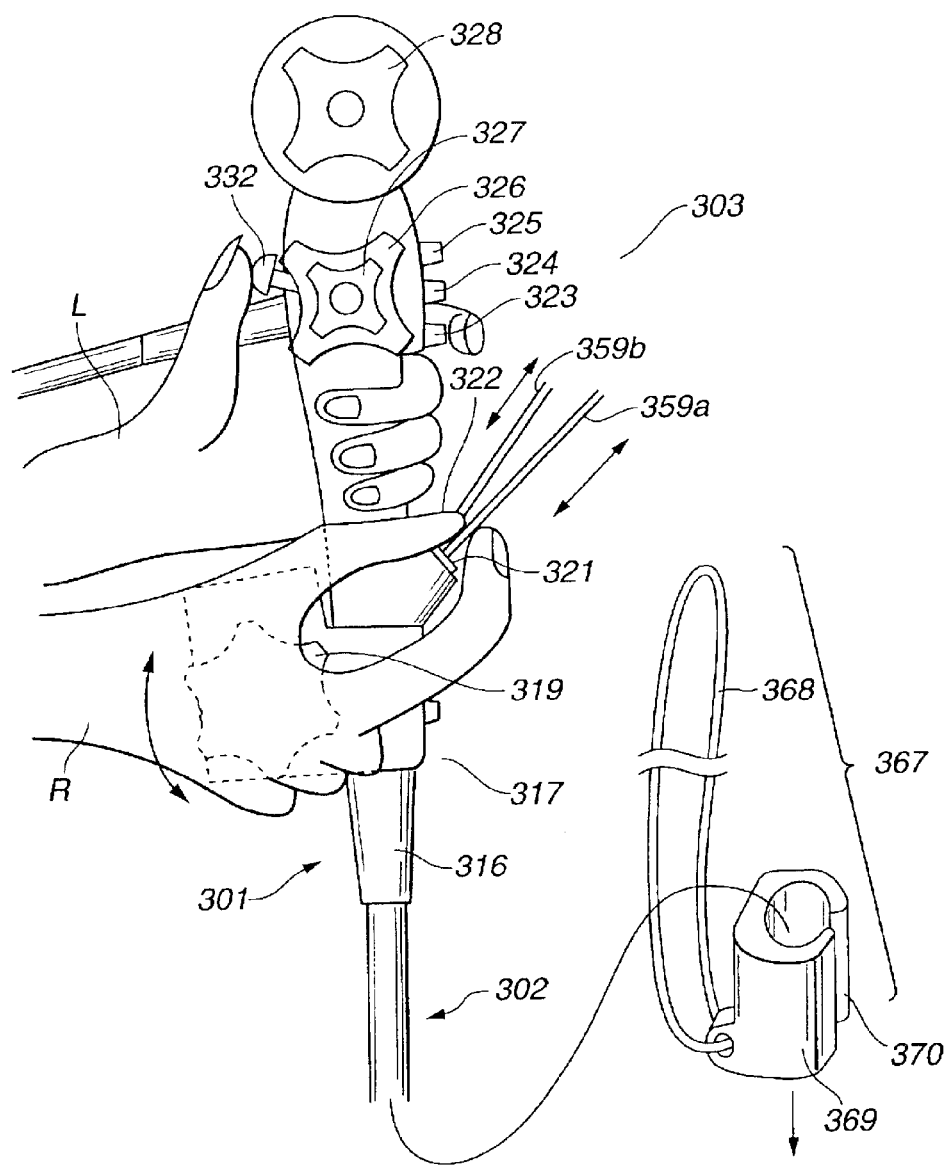

As shown in FIG. 80, an operator normally holds the grip 320 with his/her left hand. The first bending section manipulation knobs 326 and 327 located above the grip are handled with the left hand, whereby the endoscope is angled.

Therefore, the swing stand manipulator 317 located below the grip 320 is handled with the right hand. In the present embodiment, the first swing stand manipulation knob 319 of the swing stand manipulator 317 is disposed on the right side of the operation unit 303 so that the first swing stand manipulation knob 319 can easily be handled with the right hand. In this case, the first bending section manipulation knobs 326 and 327 are present on the face of the operation unit 303, and the first swing stand manipulation knob 319 is present on the right side of the operation unit 303.

In other words, the first swing stand manipulation knob 319 is disposed on one side of the operation unit 303 on which the first swing stand manipulation knob 319 can be easily handled with the right hand other than the hand with which an operator holds the operation unit 303. This helps the operator handle the first swing stand manipulation knob 319.

FIG. 75 to FIG. 79 show the internal structure of the swing stand manipulator 317.

As shown in FIG. 75, a lock shaft 334 is fixed to a swing stand manipulator body 333. A manipulation knob rotation cylinder 334a fixed to the first swing stand manipulation knob 319 is engaged with the periphery of the lock shaft 334. The manipulation knob rotation cylinder 334a can rotate freely with the lock shaft 334 left intact. A turntable 335 is engaged with the tip of the manipulation knob rotation cylinder 334a. The turntable 335 can rotate freely with the lock shaft 334 left intact.

When the first swing stand manipulation knob 319 is turned, the rotation is conveyed to the turntable 335 via the manipulation knob rotation cylinder 334a. Two rods 336 are fixed to the turntable 335 with rotary pins 337 so that they can rotate freely.

The rods 336 are passed through guide holes 339 bored in the swing stand manipulator body 333 and fixed to brackets 343 located on the opposite side of the swing stand manipulator body 333. The guide holes 339 are shaped like linear slits, and the rods 336 move within the guide holes 339 with friction reduction members 338 between them.

Consequently, the rotation of the first swing stand manipulation knob 319 is converted into a rectilinear movement by the guide holes 339. Moreover, rectilinear movement members that make a rectilinear movement are arranged in letter U on the back of a fixing member of the lock shaft 334. This enables reduction in the overall length of the first treatment instrument swing stand manipulating mechanism 318.

The rods 336 have the movable range thereof restricted by two stoppers 340 whose positions can be freely adjusted relative to the swing stand manipulator body 333. Wire coupling members 342 are freely detachably attached to the brackets 343 using screws.

On the other hand, two angling wires 341 serving as a manipulation conveying member are extended from the first treatment instrument swing stand 310. The angling wires 341 are sheathed with angling wire guide tubes 344. The angling wires 341 are each made by twisting a plurality of conductors. Incidentally, the distal parts of the angling wire guide tubes 344 are secured to open upon the distal component assembly 305 of the insertion unit 2 in which the first treatment instrument swing stand 310 is secured while being permitted to swing freely.

The proximal parts of the angling wires 341 and the wire coupling members 342 are joined firmly by performing soldering or brazing. The angling wire guide tubes 344 are freely detachably attached to the distal ends of cylinders 347 with guide tube holding members 345 between them so that the cylinders 347 will be kept watertight.

The wire coupling members 342 rectilinearly moves within the cylinders 347 fixed to the swing stand manipulator body 331. A joint joining each wire coupling member 342 and each bracket 343 is disposed in a space other than the space linking the insertion unit 302 and operation unit 303.

Figure 76:
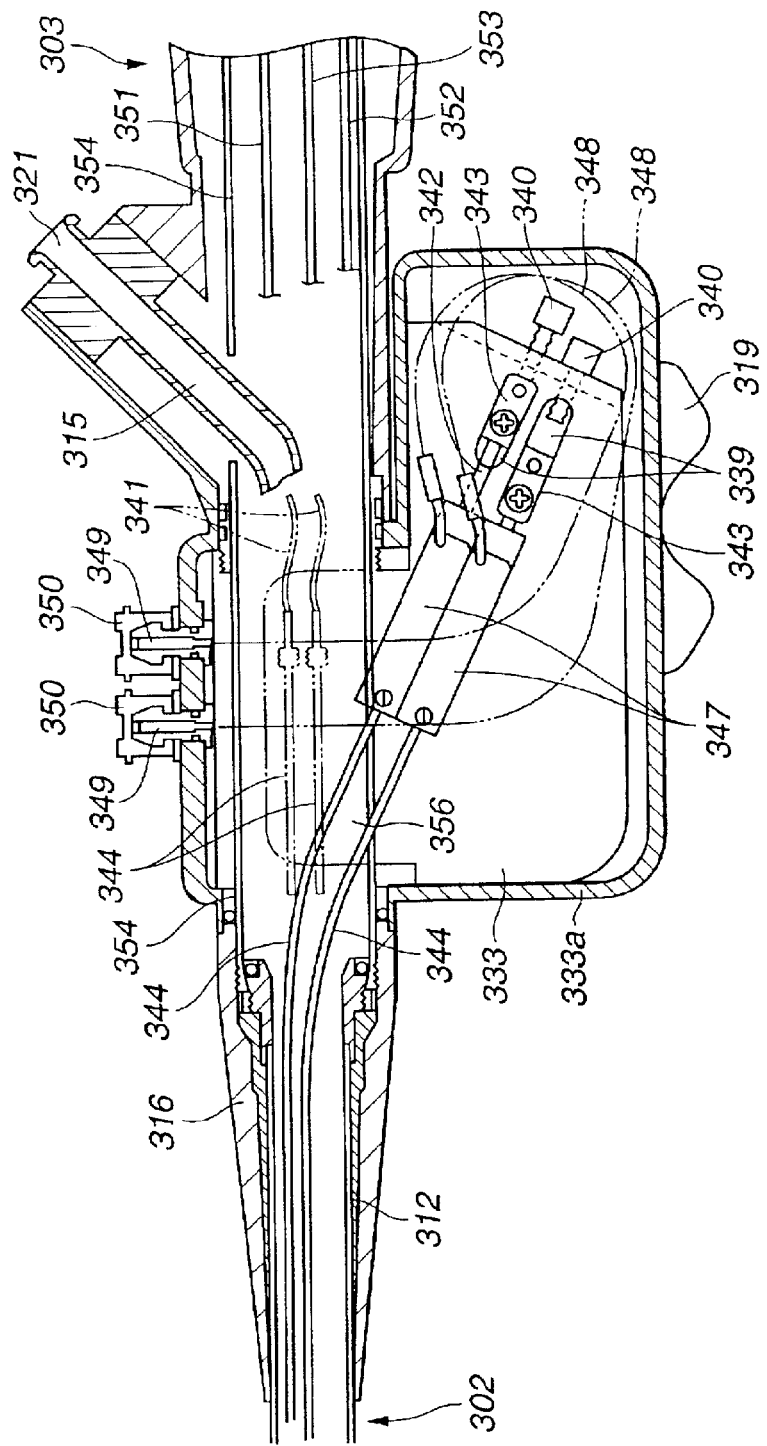
Figure 77:
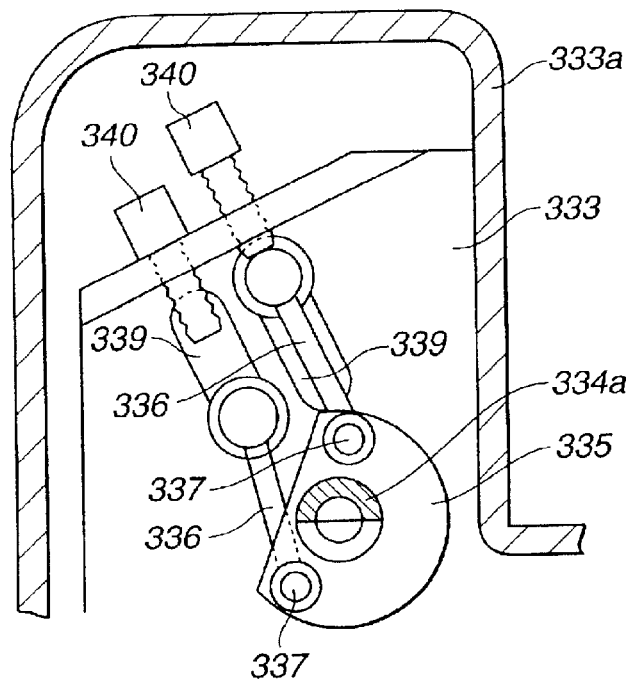
Figure 78:
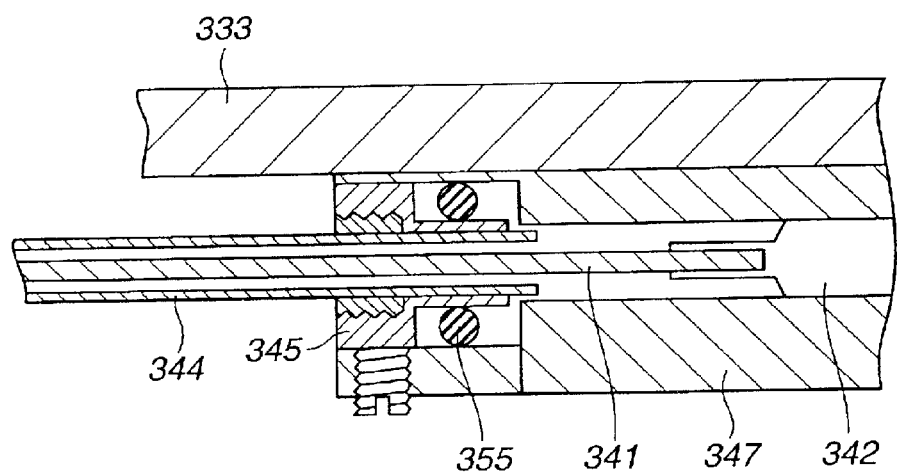

The proximal parts of the angling wire guide tubes 344 are, as indicated with an alternate long and two short dashes line in FIG. 76, led out of a notch window 356 formed in an operation unit cylindrical structure 354 (or a joint member joining the insertion unit 302 and operation unit 303). The proximal parts are then coupled to the first treatment instrument swing stand manipulating mechanism 318 that includes the wire coupling members 342 and brackets 343.

In other words, in the space linking the insertion unit 302 and operation unit 303, a light guide fiber bundle 351, a signal cable 352, an air/water supply tube 353, and other built-in components are placed. However, the first treatment instrument swing stand manipulating mechanism 318 is absent from the placement space. Moreover, the angling wires 341 are coupled to the first treatment instrument swing stand manipulating mechanism 318 while being tensed. The angling wires 341 therefore excellently respond to a manipulation. Furthermore, since the angling wires 341 are each made by twisting a plurality of conductors. Compared with a wire made by twisting a single conductor, the wire is strong to a bend or compression. The angling wires 341 can therefore be rather highly tensed.

Cleansing solution supply tubes 348 each used to cleanse the gap between the angling wire guide tube 344 and angling wire 341 are coupled to the cylinders 347 respectively. One ends of the cleansing solution supply tubes 348 are fitted into cleansing ports 349 formed in a swing stand manipulator armor member 333a fixed to the swing stand manipulator body 333.

Syringes (not shown) are fitted into the cleansing ports 349, whereby a cleansing solution can be supplied to the tubes. The cleansing ports 349 have cleansing port caps 350 formed with electrically insulating members and can thus be capped when they are unused.

Furthermore, a cover 346 is freely detachably attached to the swing stand manipulator armor member 333a with a watertight member 355 between them so that the swing stand manipulator armor member 333a will be kept watertight. When the cover 346 is opened, the stoppers 340 can be adjusted. Thereby, the swingable range of the first treatment instrument swing stand 310 can be adjusted easily.

The proximal opening end of a tube led to the forward water outlet 309 (see FIG. 74) may be disposed in the swing stand manipulator armor member 333a.

Figure 79A:
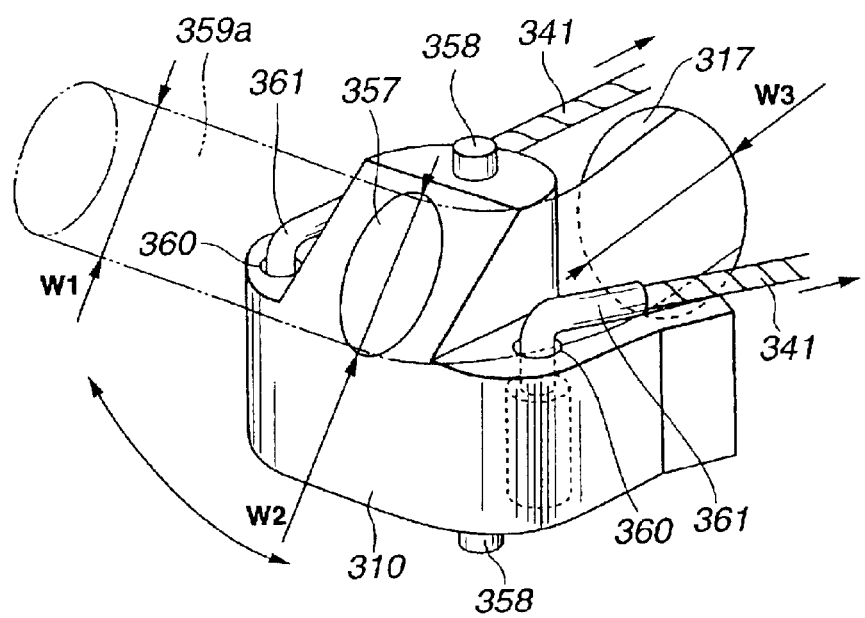
FIG. 79A is a perspective view showing a first treatment instrument swing stand.

FIG. 79A is a perspective view of the first treatment instrument swing stand 310. The first treatment instrument swing stand 310 has a treatment instrument passage hole 357 through which a treatment instrument 359 is passed, and has two angling wire lock holes 360 bored in both the sides thereof with the rotation shafts 358 between them.

Figure 79B:
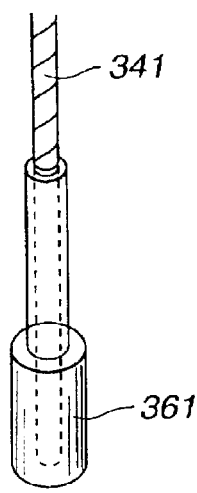
FIG. 79B is a perspective view showing an angling wire.

Referring to FIG. 79B, after the wire holding member 361 is soldered or brazed to the terminal end of the angling wire 341, the angling wire 341 is inserted into the opening of the angling wire lock hole 360 contained in the bottom of the first treatment instrument swing stand 310, and then bent. The two angling wires 341 are thus fixed to the first treatment instrument swing stand 310 in such a manner that they can rotate freely.

Figure 79C:
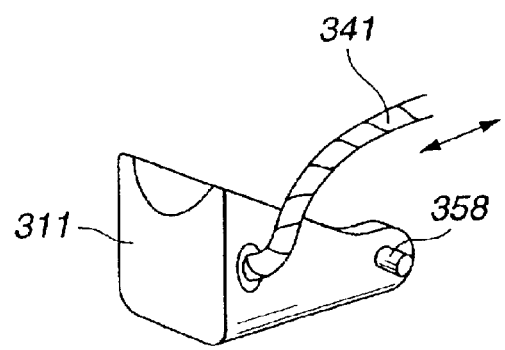
FIG. 79C is a perspective view showing a second treatment instrument swing stand.

By pulling the two angling wires 341 secured with the rotation shafts 358 between them, the first treatment instrument swing stand 310 can swing in both the directions with the rotation shafts 358 as a center of rotation. FIG. 79C shows the second treatment instrument swing stand 311 that is supported by the rotation shafts 358 while being permitted to freely swing in the upward and downward directions. The angling wire 341 is coupled to the second treatment instrument swing stand 311.

Referring to FIG. 79A, W1 denotes the outer diameter of the treatment instrument 359, W2 denotes the diameter of the opening portion of the first treatment instrument swing stand 310, and W3 denotes the inner diameter of the distal opening portion of the first treatment instrument passage channel 315. The diameters W1, W2, and W3 have the relationships that W1 equals approximately W2 and that W1 is smaller than W3. Since W1 equals approximately W2, when the first treatment instrument swing stand 310 is swung, the treatment instrument 359 will not deflect. Moreover, since W1 is smaller than W3, the treatment instrument 359 can be inserted into the first treatment instrument passage channel 315 smoothly.

Next, operations to be exerted by the fourteenth embodiment will be described below.

FIG. 80 is a perspective view showing a way of holding the operation unit 303 and handling the swing stand manipulator 317.

With an operator's left hand L, the operation unit is held, and the second swing stand manipulation knob 332, air/water supply control button 323, suction control button 324, image record button 325, and first bending section manipulation knobs 326 and 327 are handled. With the operator's right hand R, the treatment instruments 359a and 359b are advanced or withdrawn, the second swing stand manipulation knob 319 is handled, and the insertion unit 2 is advanced, withdrawn, or twisted.

Referring to FIG. 80, a neckwear-type scope holder 367 is composed of a holder body 369 and a strap 368. A slit 370 is formed in one side of the holder body 369. The insertion unit 302 is inserted through the slit 370 so that the antibreakage member 316 will be held in the holder body.

An operator hangs the strap 368 on his/her neck, whereby the overall weight of the operation unit 303 including the swing stand manipulator 317 can be borne by the left hand L and the neck. The load to be imposed on the operator during a long-term treatment can be thus reduced.

Incidentally, operations concerning treatment have been described in conjunction with FIG. 8 to FIG. 10 and FIG. 31, and the description of the operations will be omitted.

In the present embodiment, the operation unit 303 and swing stand manipulator 317 may not be a combination of independent units but may be integrated into one unit. The second bending section manipulation knob 328 is disposed independently of the first bending section manipulation knobs 326 and 327 and included in an independent mechanism. Alternatively, the first bending section manipulation knobs 326 and 327 and the second bending section manipulation knob 328 may be disposed at the same position and included in the same mechanism.

Furthermore, the directions of swing in which the first treatment instrument swing stand 310 and second treatment instrument swing stand 311 can swing may be such that the first treatment instrument swing stand 310 can swing in the upward and downward directions and the second treatment instrument swing stand 311 can swing in the rightward and leftward directions.

Figure 81:
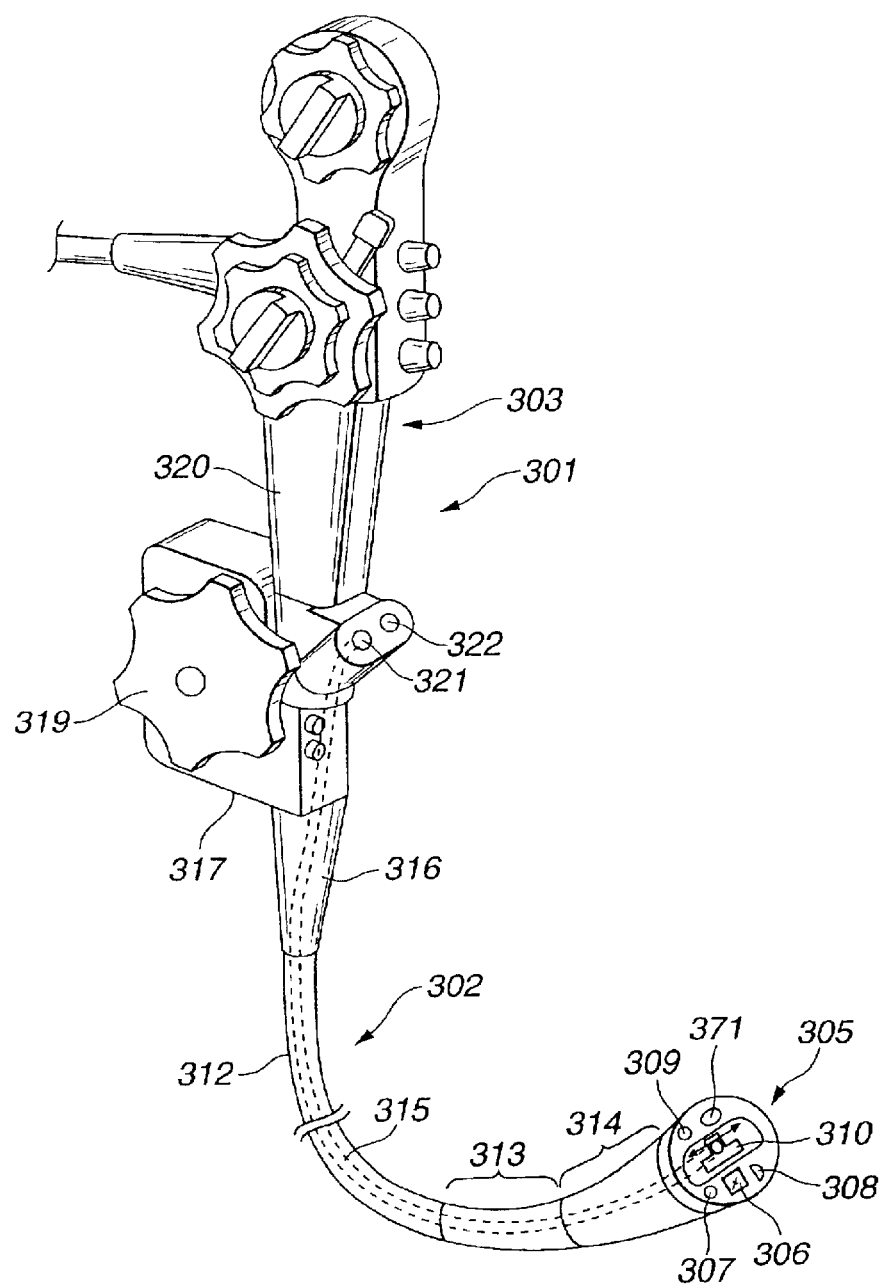
Figure 85B:
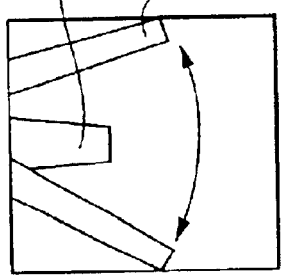

Like a first variant shown in FIG. 81, an endoscope may be devoid of the second treatment instrument swing stand 311 and the second swing stand manipulation knob 332. Therefore, without the second treatment instrument swing stand 311, the second treatment instrument passage channel opening portion 371 linked to the second operation unit-side opening 322 may not open upon the distal component assembly 305. In this case, images of treatment instruments 359a and 359b are displayed on the monitor as shown in FIG. 85B.

Figure 82A:
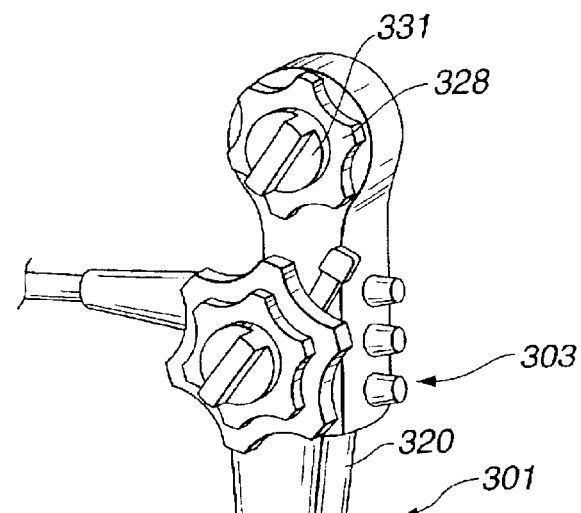
FIG. 82A is a perspective view showing an endoscope in accordance with a second variant.
Figure 82B:
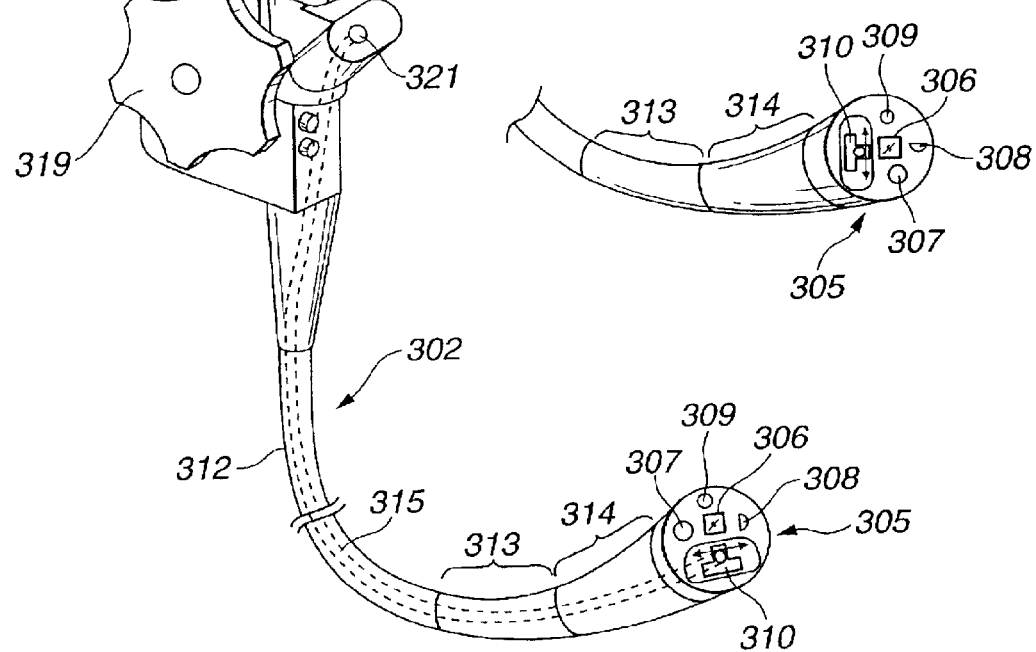
FIG. 82B is a perspective view showing a distal portion of an endoscope in accordance with a third variant.

Moreover, like second and third variants shown in FIG. 82A and FIG. 82B, an endoscope may be devoid of the second treatment instrument passage channel (not shown) shown in FIG. 74, second treatment instrument swing stand 311, second operation unit-side opening 322, and second swing stand manipulation knob 332.

Figure 85D:
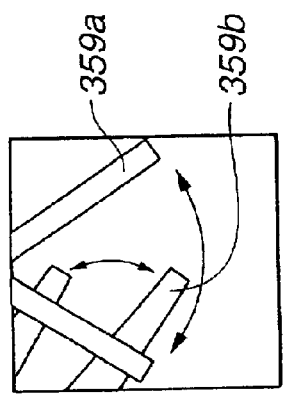
Figure 85C:
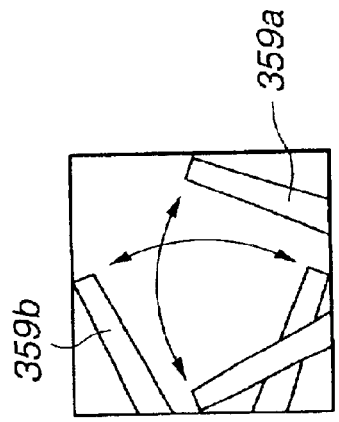

FIG. 82A and FIG. 82B are different from each other in the position of the first treatment instrument swing stand 310 relative to the observation window 303. In the case of FIG. 82A, an image of the treatment instrument 359a is displayed on the monitor as shown in FIG. 85C. In the case of FIG. 82B, an image of the treatment instrument moves as shown in FIG. 85D. Incidentally, the second bending section 313, second bending section manipulation knob 328, and second turn/lock knob 331 may be excluded.

Figure 83:
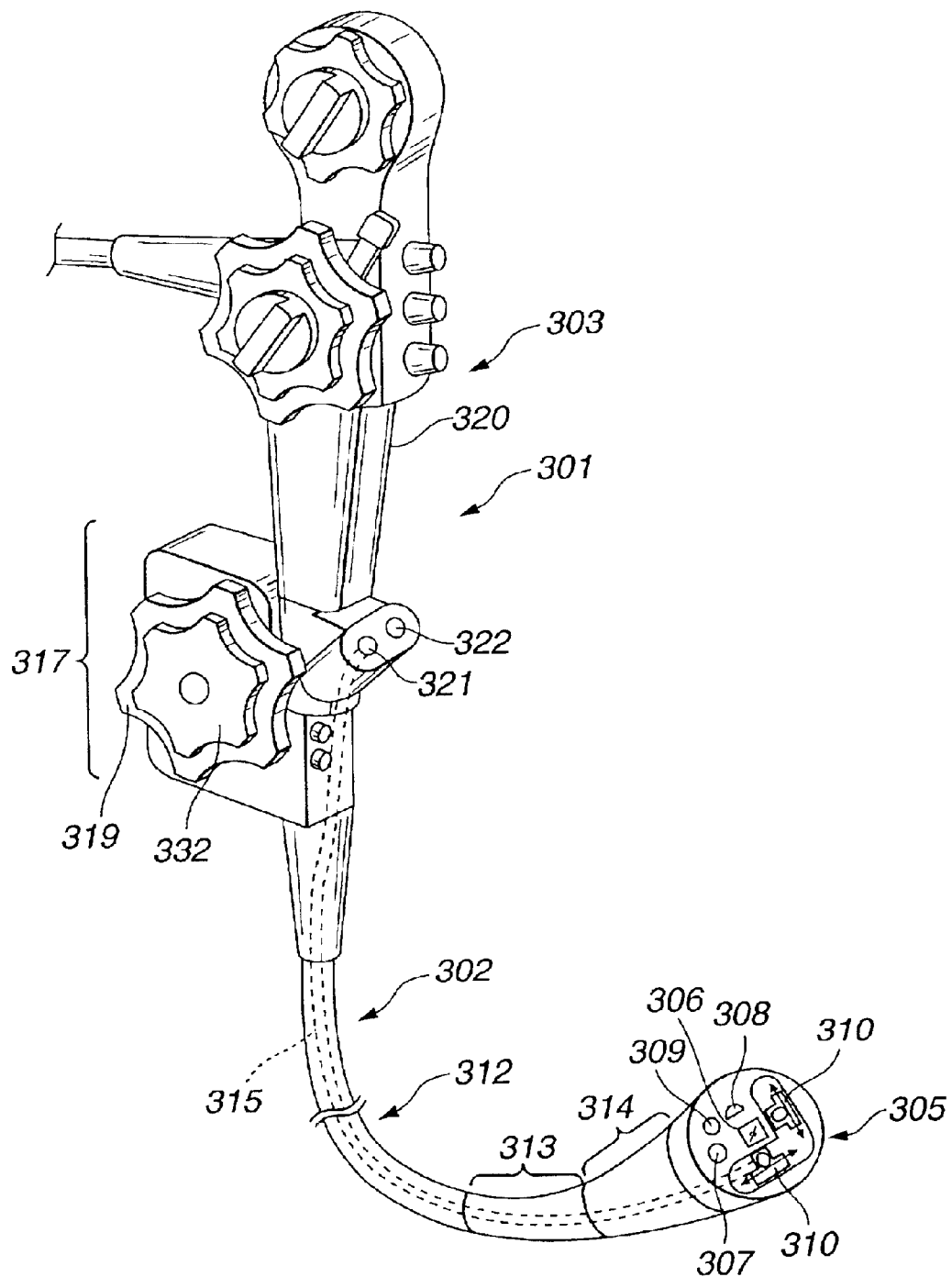

Like a fourth variant shown in FIG. 83, the second treatment instrument swing stand 311 may be changed to the first treatment instrument swing stand 310, and the second swing stand manipulation knob 332 may be positioned in the swing stand manipulator 317. (Namely, a plurality of first treatment instrument swing stands 310 each of which is remotely manipulated using at least two angling wires may be mounted in the distal component assembly 305. The first treatment instrument swing stands 310 may be manipulated using the first swing stand manipulation knob 319 and second swing stand manipulation knob 332 formed on the swing stand manipulator 317.)

Figure 85E:
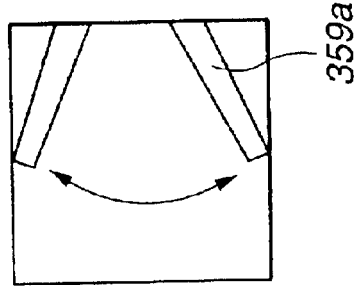

However, in this case, two first treatment instrument swing stand manipulating mechanisms 318 are incorporated in the swing stand manipulator 317. In the case of FIG. 83, the images of the treatment instruments 359a and 359b move on the monitor as shown in FIG. 85E.

Figure 84:
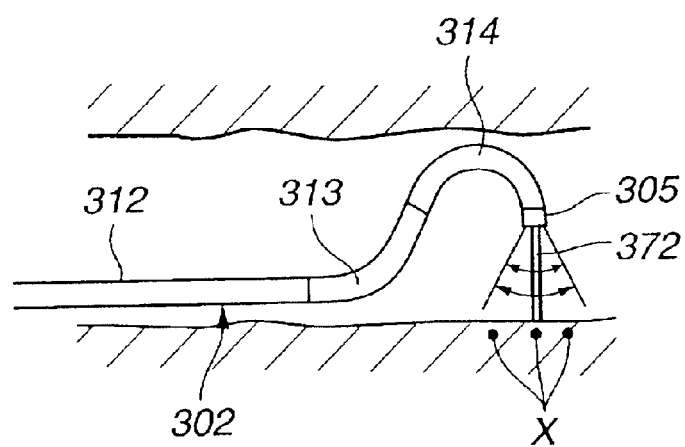

FIG. 84 shows a scene where bleeding is arrested using, for example, the endoscope 301 shown in FIG. 82B but the mucosa is not resected. Since a hemostatic probe 372 can be swung, bleeding points X scattered over a wide range can be arrested effectively. Moreover, since the second bending section 313 is included, a target region can be viewed in front of it at a proper distance, and hemostasis can be achieved accurately. The first swing stand manipulation knob 319 is disposed on the same side of the operation unit on which the first bending section manipulation knobs 326 and 327 and the second bending section manipulation knob 328 are present. The first swing stand manipulation knob 319 can therefore be handled easily with the right hand. The hemostatic probe 372 is advanced or withdrawn with the right hand. This is advantageous because the right and left hands can be used in combination.

Figure 86:
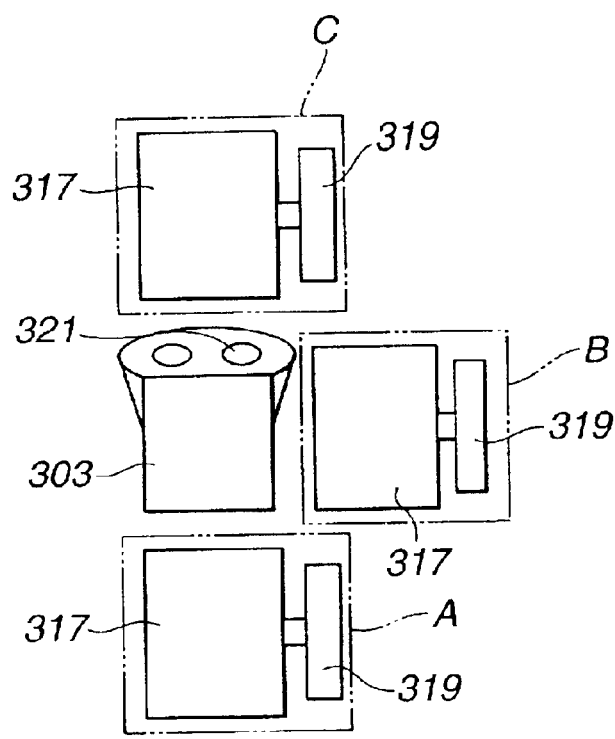
FIG. 86 shows an example of the position of a swing stand manipulator relative to an operation unit included in a fifteenth embodiment of the present invention.

FIG. 86 is concerned with a fifteenth embodiment, showing an example of the positioning of the swing stand manipulator 317 relative to the operation unit 303.

The case where the positioning of the swing stand manipulator 317 relative to the operation unit 303 is positioning A refers to the aforesaid fourteenth embodiment. The positioning of the swing stand manipulator 317 relative to the operation unit 303 may be positioning B or positioning C. The other features are identical to those of the fourteenth embodiment, and the description will be omitted.

The preferred embodiments of the present invention have been by referring to the accompanying drawings. I will be understood that the present invention is not limited to those precise embodiments but various changes and modifications thereof can be made by one skilled in the art without a departure from the spirit or scope of the invention described in the appended claims.

What is claimed is:

1. An endoscope comprising:
   an elongated insertion unit to be inserted into an object;
   an observation window included in the distal part of said insertion unit and having an objective optical system, which offers a predetermined field of view that defines a view image, mounted thereon;
   a treatment instrument passage channel which lies through said insertion unit and through which a treatment instrument is passed; and
   a treatment instrument swing stand located near the distal opening portion of said treatment instrument passage channel, and permitting the distal part of the treatment instrument to move into a first area and a second area defined by a centerline, which bisects the field of view in the rightward and leftward directions.

2. An endoscope according to claim 1, wherein the positional relationship between said treatment instrument swing stand and said objective optical system is determined so that when the distal part of a treatment instrument led out of the distal opening portion of said treatment instrument passage channel enters the field of view, the distal part of the treatment instrument will be observed to project substantially from the upper edge or lower edge of the field of view.

3. An endoscope according to claim 1, wherein when said treatment instrument swing stand is swung in order to project the distal part of a treatment instrument from the distal part of said insertion unit, if the distal part of the treatment instrument is observed near the centerline that bisects the field of view in the rightward and leftward directions, the tip of the treatment instrument is located farthest from the distal face of the distal part of said insertion unit.

4. An endoscope according to claim 1, wherein said treatment instrument swing stand introduces the tip of a treatment instrument, which is led out of the distal opening portion of said treatment instrument passage channel, to a position near a centerline, which bisects the field of view in the upward and downward directions, within a depth of field offered by said objective optical system.

5. An endoscope according to claim 1, wherein when said treatment instrument swing stand is held neutral, the treatment instrument led out of said distal opening portion by way of said treatment instrument swing stand is located near the centerline of the field of view.

6. An endoscope according to claim 1 comprising:
   an elongated insertion unit to be inserted into a body cavity or the like;

an observation window included in the distal part of said insertion unit and having an objective optical system, which offers a predetermined field of view that defines a view image, mounted thereon;

a treatment instrument passage channel which lies through said insertion unit and through which a treatment instrument is passed, wherein said distal opening portion of said treatment instrument passage channel is disposed behind said observation window in the axial direction of said insertion unit; and a treatment instrument swing stand located near the distal opening portion of said treatment instrument passage channel, and permitting the distal part of the treatment instrument to move in both the rightward and leftward directions of said endoscope with a centerline, which bisects the field of view in the rightward and leftward directions, as a border.

7. An endoscope according to claim 6, wherein:

a notched inclined surface that is inclined with respect to a direction orthogonal to the axial direction of said insertion unit is formed near one edge of a portion of said distal part that contains said observation window; and an opening of said distal opening portion of said treatment instrument passage channel is contained in said inclined surface.

8. An endoscope according to claim 1, further comprising:

a second treatment instrument passage channel independent of said treatment instrument passage channel; and a second treatment instrument swing stand that is located near a second opening portion which is formed as the distal member of said second treatment instrument channel, and that swings the distal part of a second treatment instrument, which is passed through said second treatment instrument passage channel, in the second directions of swing different from the directions of swing in which the distal part of a treatment instrument is swung by said treatment instrument swing stand.

9. An endoscope according to claim 1, wherein an imaging device for photoelectrically converting an optical image is disposed at the position of the image plane of said objective optical system.

10. An endoscope comprising:

an elongated insertion unit to be inserted into a body cavity or the like;

an observation window included in the distal part of said insertion unit and having an objective optical system, which offers a predetermined field of view that defines a view image, mounted thereon;

a treatment instrument passage channel which lies through said insertion unit and through which a treatment instrument is passed; and a treatment instrument swing stand located near the distal opening portion of said treatment instrument passage channel, and permitting the distal part of the treatment instrument to move in both the rightward and leftward directions of said endoscope with a centerline, which bisects the field of view in the rightward and leftward directions, as a border, wherein when said treatment instrument swing stand is swung, if the distal part of a treatment instrument moves from a position near the center of the field of view to the right or left edge thereof, a trajectory traced by the tip of the treatment instrument is displaced upwards within the field of view.

11. An endoscope comprising:

an elongated insertion unit to be inserted into a body cavity or the like;

an observation window included in the distal part of said insertion unit and having an objective optical system, which offers a predetermined field of view that defines a view image, mounted thereon;

a treatment instrument passage channel which lies through said insertion unit and through which a treatment instrument is passed; and a treatment instrument swing stand located near the distal opening portion of said treatment instrument passage channel, and permitting the distal part of the treatment instrument to move in both the rightward and leftward directions of said endoscope with a centerline, which bisects the field of view in the rightward and leftward directions, as a border, wherein said treatment instrument swing stand is disposed above said observation window.

12. An endoscope comprising:

an elongated insertion unit to be inserted into a body cavity or the like;

an observation window included in the distal part of said insertion unit and having an objective optical system, which offers a predetermined field of view that defines a view image, mounted thereon;

a treatment instrument passage channel which lies through said insertion unit and through which a treatment instrument is passed; and a treatment instrument swing stand located near the distal opening portion of said treatment instrument passage channel, and permitting the distal part of the treatment instrument to move in both the rightward and leftward directions of said endoscope with a centerline, which bisects the field of view in the rightward and leftward directions, as a border, wherein said treatment instrument swing stand further comprises a swinging mechanism that permits said treatment instrument swing stand to swing in four directions.

13. An endoscope comprising:

an elongated insertion unit to be inserted into a body cavity or the like;

an observation window included in the distal part of said insertion unit and having an objective optical system, which offers a predetermined field of view that defines a view image, mounted thereon;

a treatment instrument passage channel which lies through said insertion unit and through which a treatment instrument is passed; and a treatment instrument swing stand located near the distal opening portion of said treatment instrument passage channel, and permitting the distal part of the treatment instrument to move in both the rightward and leftward directions of said endoscope with a centerline, which bisects the field of view in the rightward and leftward directions, as a border, wherein:

an operation unit formed proximally to said insertion unit includes a treatment instrument swing stand manipulating mechanism that is disposed near the proximal opening portion of said treatment instrument passage channel and that is used to remotely manipulate said treatment instrument swing stand using a manipulation conveyance member coupled to said treatment instrument swing stand;

said treatment instrument swing stand can be swung using said manipulation conveyance member; and the proximal end of said manipulation conveyance member is coupled to said treatment instrument swing stand manipulating mechanism outside a space linking said insertion unit and said operation unit.

14. An endoscope according to claim 13, wherein a manipulation knob included in said treatment instrument swing stand manipulating mechanism is disposed on the right side of said operation unit.

15. An endoscope according to claim 13, wherein a first bending section is disposed proximally to said distal part of said insertion unit, and a second bending section is disposed proximally to said first bending section.

16. An endoscope comprising:
an elongated insertion unit to be inserted into an object;
an observation window included in the distal part of said insertion unit and having an objective optical system, which offers a predetermined field of view that defines a view image, mounted thereon;
first and second treatment instrument passage channels which lie through the insertion unit and through which first and second treatment instruments are passed;
a treatment instrument swing stand located near the distal opening portion of the first treatment instrument passage channel, and permitting the distal part of the first treatment instrument to swing into a first area and a second area defined by a centerline, which bisects the field of view in the upward and downward directions or in the rightward and leftward directions.

17. An endoscope according to claim 16, further comprising a second treatment instrument swing stand that is located near the distal opening portion of said second treatment instrument passage channel and that permits the distal part of a second treatment instrument to swing substantially in the upward and downward directions of said endoscope within the field of view.

18. An endoscope according to claim 16, wherein the positional relationship between said first treatment instrument swing stand and said objective optical system is determined so that: when the distal part of the first treatment instrument led out of said distal opening portion enters the field of view, the distal part of the first treatment instrument will be observed to project substantially from the upper or lower edge of the field of view.

19. An endoscope according to claim 16, wherein when said first treatment instrument swing stand is swung, the distal part of said first treatment instrument is swung from a neutral position, at which said first treatment instrument is not swung, in both the rightward and leftward directions by a nearly equal magnitude.

20. An endoscope according to claim 16, wherein said first treatment instrument swing stand is disposed to introduce the distal part of the first treatment instrument, which is led out of the distal opening portion, to a position near a centerline, which bisects the field of view in the upward and downward directions, within a depth of field offered by said objective optical system.

21. An endoscope comprising:
an elongated insertion unit to be inserted into a body cavity;
an observation window included in the distal part of said insertion unit and having an objective optical system, which offers a predetermined field of view that defines a view image, mounted thereon;
first and second treatment instrument passage channels which lie through said insertion unit and through which first and second treatment instruments are passed; and
a treatment instrument swing stand located near the distal opening portion of said first treatment instrument passage channel, and permitting the distal part of a first treatment instrument to swing in both the rightward and leftward directions of said endoscope with a centerline, which bisects the field of view in the rightward and leftward directions, as a border, wherein when said treatment instrument swing stand is swung, if the distal part of the first treatment instrument moves from a position near the center of the field of view to the right or left edge thereof, a trajectory traced by the tip of said first treatment instrument curves upwards within the field of view.

22. An endoscope comprising:
an elongated insertion unit to be inserted into a body cavity;
an observation window included in the distal part of said insertion unit and having an objective optical system, which offers a predetermined field of view that defines a view image, mounted thereon;
first and second treatment instrument massage channels which lie through said insertion unit and through which first and second treatment instruments are passed; and
a treatment instrument swing stand located near the distal opening portion of said first treatment instrument passage channel, and permitting the distal part of a first treatment instrument to swing in both the rightward and leftward directions of said endoscope with a centerline, which bisects the field of view in the rightward and leftward directions, as a border, wherein said first treatment instrument swing stand is disposed above said observation window.

23. An endoscope comprising:
an elongated insertion unit to be inserted into a body cavity;
an observation window included in the distal part of said insertion unit and having an objective optical system, which offers a predetermined field of view that defines a view image, mounted thereon;
first and second treatment instrument passage channels which lie through said insertion unit and through which first and second treatment instruments are passed; and
a treatment instrument swing stand located near the distal opening portion of said first treatment instrument passage channel, and permitting the distal part of a first treatment instrument to swing in both the rightward and leftward directions of said endoscope with a centerline, which bisects the field of view in the rightward and leftward directions, as a border, wherein said first treatment instrument stand swing further comprises a swinging mechanism that permits said first treatment instrument swing stand to swing in four directions.

24. An endoscope comprising:
an elongated insertion unit to be inserted into a body cavity;
an observation window included in the distal part of said insertion unit and having an objective optical system, which offers a predetermined field of view that defines a view image, mounted thereon, wherein said distal opening portion is disposed behind said observation window in the axial direction of said insertion unit;
first and second treatment instrument passage channels which lie through said insertion unit and through which first and second treatment instruments are passed; and
a treatment instrument swing stand located near the distal opening portion of said first treatment instrument passage channel, and permitting the distal part of a first treatment instrument to swing in both the rightward and leftward directions of said endoscope with a centerline, which bisects the field of view in the rightward and leftward directions, as a border.

25. An endoscope, comprising:

an elongated insertion unit to be inserted into an object;

an observation window included in the distal part of the insertion unit for defining a view image of an object;

a treatment instrument passage channel which lies through the insertion unit and through which a treatment instrument is passed; and a treatment instrument swing stand located near the distal opening portion of the treatment instrument passage channel, and permitting the distal part of the treatment instrument to swing in one direction and in the other direction that is substantially opposite to the one direction with respect to the distal opening portion of the treatment instrument passage channel, wherein the treatment instrument swing stand permits the distal part of the treatment instrument to swing into a first area arid a second area defined by a centerline, which bisects the filed of view in the upward and downward directions or in the rightward and leftward directions.

26. An endoscope according to claim 25, wherein the treatment instrument swing stand permits the distal part of the treatment instrument to swing in the rightward and leftward directions of a view image observed by a user.

27. An endoscope according to claim 26, wherein the distal opening portion of the treatment instrument passage channel is located substantially at the center of the view image in the rightward and leftward directions.

28. An endoscope according to claim 27, wherein the treatment instrument, which is led out of the distal opening portion of the treatment instrument passage channel, is observed such as to be projected from the lower side of the view image.

29. An endoscope according to claim 25, wherein when the treatment instrument swing stand is swung in order to project the distal part of a treatment instrument from the distal part of the insertion unit, if the distal part of the treatment instrument is observed near the centerline that bisects the field of view in the rightward and leftward directions, the tip of the treatment instrument is located farthest from the distal face of the distal part of the insertion unit.

30. An endoscope according to claim 25, wherein when the treatment instrument swing stand is swung, if the distal part of a treatment instrument moves from a position near the center of the field of view to the right or left edge thereof, a trajectory traced by the tip of the treatment instrument is displaced upwards within the field of view.

31. An endoscope according to claim 25, wherein the distal opening portion of the treatment instrument passage channel is disposed behind the observation window in the axial direction of the insertion unit.

32. An endoscope according to claim 31, wherein:

a notched inclined surface that is inclined with respect to a direction orthogonal to the axial direction of the insertion unit is formed near one edge of a portion of the distal part that contains the observation window; and an opening of the distal opening portion of the treatment instrument passage channel is contained in the inclined surface.

33. An endoscope according to claim 25, further comprising:

a second treatment instrument passage channel independent of said treatment instrument passage channel; and a second treatment instrument swing stand that is located near a second opening portion which is formed as the distal member of said second treatment instrument channel, and that swings the distal part of a second treatment instrument, which is passed through said second treatment instrument passage channel, in the second directions of swing different from the directions of swing in which the distal part of a treatment instrument is swung by said treatment instrument swing stand.

* * * * *